United States Patent [19]

Himmelsbach et al.

[11] Patent Number: 5,977,102
[45] Date of Patent: Nov. 2, 1999

[54] PYRIMIDO [5, 4-D] PYRIMIDINES, PHARMACEUTICALS CONTAINING THESE COMPOUNDS, THEIR USE AND PROCESSES FOR THEIR PREPARATION

[75] Inventors: Frank Himmelsbach, Mittelbiberach; Georg Dahmann, Ummendorf, both of Germany; Thomas von Ruden, Baden; Thomas Metz, Vienna, both of Austria

[73] Assignee: Dr. Karl Thomae GmbH, Biberach, Germany

[*] Notice: This patent is subject to a terminal disclaimer.

[21] Appl. No.: 08/812,002

[22] Filed: Mar. 5, 1997

[30] Foreign Application Priority Data

Mar. 6, 1996 [DE] Germany ............................ 196 08 653

[51] Int. Cl.⁶ ........................ A61K 31/495; C07D 487/04
[52] U.S. Cl. ...................... 514/234.2; 514/258; 544/118; 544/256
[58] Field of Search .................................... 544/256, 118; 514/258, 234.2

[56] References Cited

U.S. PATENT DOCUMENTS

| 3,031,450 | 4/1962 | Fischer et al. | 514/258 |
| 4,478,833 | 10/1984 | Roch et al. | 514/258 |
| 4,518,596 | 5/1985 | Roch et al. | 514/232 |
| 4,714,698 | 12/1987 | Roch et al. | 514/212 |
| 5,350,749 | 9/1994 | Hackler et al. | 514/248 |
| 5,618,814 | 4/1997 | Heckel et al. | 514/234.2 |
| 5,707,989 | 1/1998 | Himmelsbach et al. | 514/228.2 |

FOREIGN PATENT DOCUMENTS

| 0 55 444 | 7/1982 | European Pat. Off. . |
| 44 31 867 | 3/1996 | Germany . |
| WO95/19774 A1 | 7/1995 | WIPO . |

OTHER PUBLICATIONS von Ruden, Thomas; Expression of functional human EGF receptor on murine bone marrow cells; The EMBO Journal vol. 7 No. 9. pp. 2749–2756, 1988.
Pierce, Jacalyn H.,; Signal Transduction Through the EGF Receptor Transfected in IL–3–Dependent Hematopoietic Cells; Science, vol. 239, pp. 628–631, 1988.
Dexter, T.M., Growth of Factor Dependent Hemopoietic Precursor Cell Lines, J. of Exp. Med.. The Rockefeller University Press, vol. 152, Oct. 1980, pp. 1036–1047.
Shibuya, Hiroshi, IL–2 and EGF Receptors Stimulate the Hematopoietic Cell Cycle via Different Signaling Pathways Demonstration of a Novel Role for C–myc, Cell, vol. 70, 57–67 Jul. 10, 1992.
Alexander, Warren S.; Expression of function c–kit receptors rescues the genetic defect of W mutant mast cells, The EMBO Journal, vol. 20, No. 23, pp. 3683–3691, 1991.

Ullrich, A; Human epidermal growth factor receptor cDNA sequence and aberrant expression of the amplified gene in A431 epidermoid carcinoma cells; Nature, vol. 309, May 31, 1984, pp. 418–425.
Miller, A. Dusty; Improved Retroviral Vectors for Gene Transfer and Expression; BioTechniques, The Journal of Laboratory Technology for Bio–research, vol. 7, No. 9 Oct. 1989 pp. 980–989.
Markowitz, Dina; A Safe Packaging Line for Gene Transfer; Separating Viral Genes on Two Different Plasmids, Journal of Virology, Apr. 1988 pp. 1120–1124.
Karasuyama, Hajime, Establishment of mouse cell lines which constitutively secrete large quantities of interleukin 2,3,4, or 5 using modified cDNA expression vectors, Eur. J. Immunol. 1988. 18 97–104.
Aboud–Pirak, Esther, Efficacy of Antibodies to Epidermal Growth Factor Receptor Against KB Carcinoma In Vitro and in Nude Mice; J. Natl. Cancer Inst. vol. 80 No. 20, pp. 1605–1611, 1988.

*Primary Examiner*—Richard L. Raymond
*Attorney, Agent, or Firm*—Robert P. Raymond; Alan R. Stempel; Mary-Ellen M. Devlin

[57] ABSTRACT

Pyrimido[5,4-d]pyrimidines of the general formula (I)

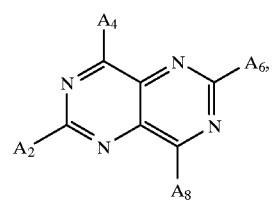

which have an inhibitory effect on signal transduction mediated by tyrosine kinases, their use for the treatment of oncoses, and their preparation. Exemplary compounds are:

(a) 4-(5-indolylamino)-6-morpholinopyrimido[5,4-d]pyrimidine;

(b) 4-(5-indolylamino)-6-[trans-(4-hydroxycyclohexyl)amino]pyrimido[5,4-d]pyrimidine;

(c) 4-[(3-chloro-4-fluorophenyl)amino]-6-[4-(morpholinocarbonylmethyl)-1-piperazinyl]pyrimido[5,4-d]pyrimidine;

(d) 4-[(3-chloro-4-fluorophenyl)amino]-6-[(4-morpholinyl)amino]pyrimido[5,4-d]pyrimidine;

(e) 4-[(3-chloro-4-fluorophenyl)amino]-6-(4-picolylamino)pyrimido[5,4-d]pyrimidine;

(f) 4-[(3-chloro-4-fluorophenyl)amino]-6-[1-trifluoroacetyl-4-piperidinylamino]pyrimido[5,4-d]pyrimidine;

(g) 4-[(3-chloro-4-fluorophenyl)amino]-6-(endo-tropinylamino)pyrimido[5,4-d]pyrimidine; and, (h) 4-[(3-chloro-4-fluorophenyl)amino]-6-(exo-tropinylamino)pyrimido[5,4-d]pyrimidine.

13 Claims, No Drawings

PYRIMIDO [5, 4-D] PYRIMIDINES, PHARMACEUTICALS CONTAINING THESE COMPOUNDS, THEIR USE AND PROCESSES FOR THEIR PREPARATION

The present invention relates to pyrimido[5,4-d] pyrimidines of the general formula

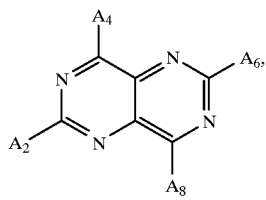

their tautomers, their stereoisomers and their salts, in particular their physiologically tolerated salts with inorganic or organic acids or bases, which have valuable pharmacological properties, in particular an inhibitory effect on signal transduction mediated by tyrosine kinases, their use for the treatment of diseases, in particular of oncoses, and their preparation.

In the above general formula I, with the proviso that at least (i) $A_2$ represents an alkyl group,
(ii) $A_8$ represents an alkyl group,
(iii) $A_4$ represents an $R_a NR_e$ group or
(iv) $A_6$ represents an $R_g$ group, $A_2$ and $A_8$, which can be identical or different, each denote a hydrogen atom or an alkyl group, $A_4$ denotes an $R_a NR_b$ group or an $R_d NR_e$ group and
$A_6$ denotes an $R_c$ group or an $R_g$ group in which
$R_a$ denotes a hydrogen atom or an alkyl group,
$R_b$ denotes a phenyl group substituted by the radicals $R_1$ to $R_3$, where
  $R_1$ denotes a hydrogen, fluorine, chlorine, bromine or iodine atom,
  an alkyl, hydroxyl, alkoxy or $C_{3-6}$-cycloalkyl group,
  a $C_{2-5}$-alkenyl or $C_{2-5}$-alkynyl group,
  a phenyl, phenoxy, phenylalkyl, phenylalkoxy, alkoxyalkyl, phenoxyalkyl, carboxyalkyl, cyanoalkyl, alkylsulphenyl, alkylsulphinyl, nitro, 1-pyrrolidinyl, 1-piperidinyl, morpholino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino or cyano group,
  a methyl or methoxy group which is substituted by 1 to 3 fluorine atoms,
  an ethyl or ethoxy group which is substituted by 1 to 5 fluorine atoms,
  $R_2$ denotes a hydrogen, fluorine, chlorine or bromine atom, an alkyl, trifluoromethyl, amino, alkylamino, dialkylamino, alkylcarbonylamino, alkylsulphonylamino, trifluoromethylsulphonylamino, hydroxyl or alkoxy group,
  $R_3$ denotes a hydrogen, fluorine, chlorine or bromine atom or an alkyl group, or
  $R_2$ together with $R_3$, when these are bonded to adjacent carbon atoms, also represent a methylenedioxy or n-$C_{3-6}$-alkylene group or a 1,3-butadiene-1,4-diyl group which is optionally substituted by a fluorine, chlorine or bromine atom, by an alkyl, alkoxy or trifluoromethyl group, and
$R_c$ denotes a 1-azetidinyl group,
  a 1-pyrrolidinyl group which can be substituted by 1 to 2 alkyl groups, by one phenyl, carboxyl, hydroxyalkyl, aminoalkyl, alkylaminoalkyl, dialkylaminoalkyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group,
  a 1-piperidinyl group which can be substituted by 1 to 2 alkyl groups, by one phenyl, hydroxyalkyl, aminoalkyl, alkylaminoalkyl, dialkylaminoalkyl, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 or 4 also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group,
  a 1-piperidinyl group which is optionally substituted by 1 or 2 alkyl groups and in which the methylene group in position 4 is replaced by an oxygen or sulphur atom, by a carbonyl, sulphinyl, sulphonyl, imino, alkylimino, hydroxy-$C_{2-4}$-alkylimino, alkoxy-$C_{2-4}$-alkylimino, aminocarbonylalkylimino, alkylaminocarbonylalkylimino, dialkylaminocarbonylalkylimino, amino-$C_{2-4}$-alkylimino, alkylamino-$C_{2-4}$-alkylimino, dialkylamino-$C_{2-4}$-alkylimino, phenylimino, phenylalkylimino, alkylcarbonylimino, alkylsulphonylimino, phenylcarbonylimino or phenylsulphonylimino group,
  a 1-azacyclohept-1-yl group which is optionally substituted by 1 or 2 alkyl groups and in which in each case the methylene group in position 4 can be replaced by an oxygen atom, by an imino, N-alkylimino, N-phenylimino, N-phenylalkylimino, N-alkylcarbonylimino, N-alkylsulphonylimino, N-phenylcarbonylimino or N-phenylsulphonylimino group, or
  a 5- to 7-membered alkyleneimino group which is optionally substituted by 1 or 2 alkyl groups and which is linked via a carbon atom to a carbon atom of a 5- to 7-membered alkyleneimino group in which the nitrogen atom can be substituted by an alkyl group,
  an ($R_4 NR_5$) group in which
    $R_4$ denotes a hydrogen atom or a $C_{1-6}$-alkyl group which can be substituted by a hydroxyl or alkoxy group, and
    $R_5$ denotes a hydrogen atom,
    a $C_{1-8}$-alkyl group which can be substituted by a phenyl, $C_{3-6}$-cycloalkyl, hydroxyl, alkoxy, cyano, carboxyl, alkoxycarbonyl, aminocarbonyl, alkylaminocarbonyl, dialkylaminocarbonyl, (2-hydroxyethyl)aminocarbonyl, 1-pyrrolidinylcarbonyl, 1-piperidinylcarbonyl, morpholinocarbonyl, 1-piperazinylcarbonyl, 4-alkyl-1-piperazinylcarbonyl, amino, formylamino, alkylamino, dialkylamino, alkylcarbonylamino, N-alkyl-alkylcarbonylamino, alkoxycarbonylamino, N-alkylalkoxycarbonylamino, alkylsulphonylamino, N-alkylalkylsulphonylamino, phenylcarbonylamino, N-alkyl-phenylcarbonylamino, phenylsulphonylamino, N-alkyl-phenylsulphonylamino, alkylsulphenyl, alkylsulphinyl, alkylsulphonyl, 1-pyrrolidinyl, 2-oxo-1-pyrrolidinyl, 1-piperidinyl, 2-oxo-1-piperidinyl, morpholino, 1-piperazinyl, 4-alkyl- 1-piperazinyl, 4-alkylcarbonyl-1-piperazinyl, 4-alkylsulphonyl-1-piperazinyl, 4-alkoxycarbonyl-1-piperazinyl, 4-cyano-1-piperazinyl, 4-formyl-1-piperazinyl, 4-aminocarbonyl-1-piperazinyl, 4-alkylaminocarbonyl-1-piperazinyl or 4-dialkylaminocarbonyl-1-piperazinyl or an $(R_8NR_7)$—CO—$NR_6$ group, where $R_6$, $R_7$ and $R_8$, which can be identical or different, each represent a hydrogen atom or an alkyl group or $R_6$ and $R_7$ together represent an n-$C_{2-4}$-alkylene group and $R_8$ represents a hydrogen atom or an alkyl group, a 2,2,2-trifluoroethyl group, a $C_{3-10}$-alkyl group substituted by 2 to 5 hydroxyl groups, a $C_{3-5}$-alkyl group substituted by one hydroxyl and additionally by one amino group, an alkenyl or alkynyl group which is optionally substituted by a phenyl group and has in each case 3 to 6 carbon atoms, it not being possible for the vinyl or ethynyl moiety to be linked to the nitrogen atom, a $C_{2-4}$-alkyl group which is substituted by a $C_{2-4}$-alkoxy group which is substituted in the ω position by a hydroxyl or alkoxy group, a phenyl group, a phenyl group which is substituted by an alkylcarbonylamino, N-alkyl-alkylcarbonylamino, (2-hydroxyethyl)amino, di-(2-hydroxyethyl)amino, N-alkyl-(2-hydroxyethyl)amino, amino, alkylamino or dialkylamino group or by an $(R_8NR_7)$—CO—$NR_6$ group, where $R_6$ to $R_8$ are defined as mentioned above, a phenyl group which is substituted by a 1-pyrrolidinyl, 1-piperidinyl, 2-oxo-1-pyrrolidinyl, 2-oxo-1-piperidinyl, morpholino, 1-piperazinyl or 4-alkyl-1-piperazinyl group, where the abovementioned heterocyclic moieties can be substituted on the carbon framework in each case by 1 or 2 alkyl groups or by one hydroxyalkyl group, a $C_{3-7}$-cycloalkyl group which can be substituted by 1 or 2 alkyl groups, by one phenyl, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, a $C_{5-7}$-cycloalkyl group which is optionally substituted by 1 or 2 methyl groups and which is substituted by a hydroxymethyl, cyano, hydroxyl, alkoxy, amino, alkylamino, dialkylamino, 2-hydroxyethylamino, di-(2-hydroxyethyl) amino, N-alkyl-2-hydroxyethylamino, alkoxycarbonylamino, N-alkylalkoxycarbonylamino, alkylcarbonylamino, N-alkylalkylcarbonylamino, alkylsulphonylamino, N-alkylalkylsulphonylamino, phenylcarbonylamino, N-alkylphenylcarbonylamino, phenylsulphonylamino, N-alkylphenylsulphonylamino or by an $(R_8NR_7)$—CO—$NR_6$ group, where $R_6$ to $R_8$ are defined as mentioned above, a $C_{5-7}$-cycloalkyl group which is optionally substituted by 1 or 2 methyl groups and which is substituted by a 1-pyrrolidinyl, 1-piperidinyl, 2-oxo-1-pyrrolidinyl, 2-oxo-1-piperidinyl, morpholino, 1-piperazinyl, 4-alkyl-1-piperazinyl or 4-alkylcarbonyl-1-piperazinyl group, it being possible for the abovementioned heterocyclic moieties to be substituted on the carbon framework in each case by 1 or 2 alkyl groups, a $C_{5-7}$-cycloalkenyl group which is optionally substituted by 1 or 2 alkyl groups, where the vinyl moiety cannot be bonded to the nitrogen atom of the $(R_4NR_5)$ group, a tetrahydrofurfuryl group, a cyclopentyl group in which the methylene group in position 3 is replaced by an oxygen atom, an imino, alkylimino, alkylcarbonylimino, formylimino, aminocarbonylimino, alkylaminocarbonylimino, alkoxycarbonylimino, alkylsulphonylimino, dialkylaminocarbonylimino or cyanoimino group, a cyclohexyl group in which the methylene group in position 3 is replaced by an imino, alkylimino, alkylcarbonylimino, alkoxycarbonylimino or alkylsulphonylimino group, a cyclohexyl group in which the methylene group in position 4 is replaced by an oxygen atom, an imino, N-alkylimino-, N-phenylimino, N-phenylalkylimino, N-formylimino, N-alkylcarbonylimino, N-phenylcarbonylimino, N-alkoxycarbonylimino, N-cyanoimino-, N-aminocarbonylimino-, N-alkylaminocarbonylimino, N,N-dialkylaminocarbonylimino, N-alkylsulphonylimino or N-phenylsulphonylimino group, a cyclohexyl group in which one methylene group is replaced by a carbonyl group, a cyclopentyl or cyclohexyl group which is optionally substituted by 1 to 2 methyl groups and which is substituted by a carboxyalkoxy, alkoxycarbonylalkoxy, aminocarbonylalkoxy, alkylaminocarbonylalkoxy, dialkylaminocarbonylalkoxy, 1-pyrrolidinylcarbonylalkoxy, 1-piperidinylcarbonylalkoxy, morpholinocarbonylalkoxy, carboxyalkyl, alkoxycarbonylalkyl, aminocarbonylalkyl, alkylaminocarbonylalkyl, dialkylaminocarbonylalkyl, 1-pyrrolidinylcarbonylalkyl, 1-piperidinylcarbonylalkyl or morpholinocarbonylalkyl group, a cyclohexylmethyl group, where the cyclohexyl moiety is substituted by a carboxyl, aminocarbonyl, alkylaminocarbonyl, dialkylaminocarbonyl, 1-pyrrolidinylcarbonyl, 1-piperidinylcarbonyl, morpholinocarbonyl, alkoxycarbonyl or hydroxymethyl group, a 3- or 4-quinuclidinyl group, $R_d$ denotes a hydrogen atom or an alkyl group, $R_e$ represents a group of the formulae

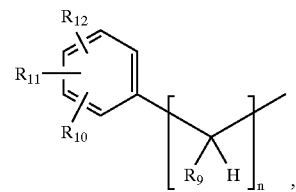

,

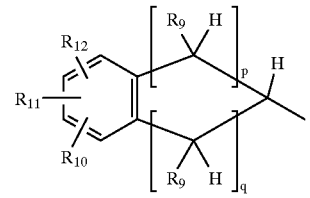

or

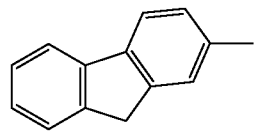

in which n represents the number 1, 2, 3 or 4, p represents the number 0, 1 or 2 q represents the number 0, 1 or 2, but where p and q must together result in at least the number 2, $R_9$ represents a hydrogen atom or a methyl group, it being possible for a plurality of $R_9$ radicals in a formula to be identical or different, $R_{10}$ represents a hydrogen, fluorine, chlorine, bromine or iodine atom, an alkyl, trifluoromethyl, ethynyl, alkoxy, cyclopropyl, trifluoromethoxy, cyano, alkoxycarbonyl or nitro group, $R_{11}$ represents a hydrogen, fluorine or chlorine atom, an amino, methyl or trifluoromethyl group and $R_{12}$ represents a hydrogen, chlorine or bromine atom, or $R_e$ denotes a 5-membered heteroaromatic ring which contains an imino group, an oxygen or sulphur atom or a nitrogen atom and an oxygen or sulphur atom or a nitrogen atom and an imino group or a sulphur atom and two nitrogen atoms, or a 6-membered heteroaromatic ring which contains 1, 2 or 3 nitrogen atoms, where the abovementioned 5- or 6-membered heteroaromatic rings can be substituted in the carbon framework by an alkyl group and, in addition, an n-butylene or 1,3-butadiene-1,4-diyl group can be attached both to the 5-membered and to the 6-membered abovementioned heteroaromatic rings via two adjacent carbon atoms, it additionally being possible for the abovementioned fused-on rings to be monosubstituted in the carbon framework by a fluorine, chlorine or bromine atom, by an alkyl, alkoxy, hydroxyl, phenyl, nitro, amino, alkylamino, dialkylamino, alkylcarbonylamino, cyano, carboxyl, alkoxycarbonyl, aminocarbonyl, alkylaminocarbonyl, dialkylaminocarbonyl, fluoromethyl, difluoromethyl, trifluoromethyl, alkylcarbonyl, aminosulphonyl, alkylaminosulphonyl or dialkylaminosulphonyl group or disubstituted by fluorine or chlorine atoms, by methyl, methoxy or hydroxyl groups, and it being possible for the abovementioned fused heterocyclic systems to be bonded both via a carbon atom or via an imino group of the heterocyclic moiety and via a carbon atom of the alicyclic aromatic moiety to the nitrogen atom of the $R_dNR_e$ group, $R_g$ denotes a 1-azetidinyl group which is optionally substituted by an alkyl group and in which the two hydrogen atoms of a methylene group are replaced by a straight-chain $C_{4-6}$-alkylene bridge, with in each case a methylene group in the $C_{4-6}$-alkylene bridge being replaced by an $R_{13}N$ group, where $R_{13}$ represents a hydrogen atom, an alkyl, hydroxy-$C_{2-4}$-alkyl, alkoxy-$C_{2-4}$-alkyl, amino-$C_{2-4}$-alkyl, alkylamino-$C_{2-4}$-alkyl, dialkylamino-$C_{2-4}$-alkyl, aminocarbonylalkyl, alkylaminocarbonylalkyl, dialkylaminocarbonylalkyl, aryl, aralkyl, formyl, alkylcarbonyl, alkylsulphonyl, arylcarbonyl, arylsulphonyl, aralkylcarbonyl, aralkylsulphonyl, alkoxycarbonyl, cyano, aminocarbonyl, alkylaminocarbonyl or dialkylaminocarbonyl group or an (alkyleneimino)carbonyl group with, in each case, 4 to 7 ring atoms in the alkyleneimino moiety, it being possible for a methylene group in position 4 in a 6- to 7-membered alkyleneimino moiety to be replaced by an oxygen or sulphur atom, by a sulphinyl, sulphonyl, imino or N-alkylimino group, or the bicyclic ring formed in this way is substituted by the radical $R_{14}$, where $R_{14}$ represents a hydroxyl, alkoxy, amino, alkylamino, dialkylamino, cyano, alkylcarbonylamino, alkylsulphonylamino, alkoxycarbonylamino, arylcarbonyl, carboxyl, alkoxycarbonyl, aminocarbonyl, alkylaminocarbonyl or dialkylaminocarbonyl group, $R_g$ denotes a 1-pyrrolidinyl, 1-piperidinyl or 1-azacyclohept-1-yl group which is optionally substituted by 1 to 2 alkyl groups and in which the two hydrogen atoms of a methylene group are replaced by a straight-chain $C_{3-6}$-alkylene bridge where, in each case, a methylene group in the $C_{3-6}$-alkylene bridge is replaced by an $R_{13}N$ group where $R_{13}$ is defined as mentioned above, or the bicyclic ring formed in this way is substituted by the radical $R_{14}$ where $R_{14}$ is defined as mentioned above, a 5- to 7-membered alkyleneimino group which is optionally substituted by 1 to 2 alkyl groups and which is linked via a carbon atom to a carbon atom of a 5- to 7-membered alkyleneimino group in which the nitrogen atom is substituted by an alkylcarbonyl, arylcarbonyl, alkylsulphonyl, alkoxycarbonyl, aminocarbonyl, alkylaminocarbonyl, dialkylaminocarbonyl or (alkyleneimino)carbonyl group with, in each case, 5 to 7 ring atoms in the alkyleneimino moiety, it being possible for a methylene group in position 4 in a 6- to 7-membered alkyleneimino moiety to be replaced by an oxygen or sulphur atom or by an imino or N-alkylimino group, a 5- to 7-membered alkyleneimino group which is optionally substituted by 1 to 2 alkyl groups and is substituted by a 3-oxo-1-piperazinylcarbonyl group which is optionally substituted in position 4 by an alkyl group, a 5- to 7-membered alkyleneimino group which is substituted by a pyridyl group and optionally in addition by 1 to 2 alkyl groups, an $(R_8NR_7)$—CO—$NR_6$ group where $R_6$ to $R_8$ are defined as mentioned above, a 3-oxo-1-piperazinyl group which is optionally substituted in position 1 by an alkyl group and optionally in addition by 1 to 2 alkyl groups, a 1-imidazolyl group which is optionally substituted by 1 to 2 alkyl groups, a 1-piperazinyl or 1-homopiperazinyl group which is optionally substituted by 1 to 2 alkyl groups and is in each case substituted in position 4 by an (alkyleneimino) carbonylalkyl group with, in each case, 5 to 7 ring atoms in the alkyleneimino moiety, it being possible for a methylene group in position 4 in a 6- to 7-membered alkyleneimino moiety to be replaced by an oxygen or sulphur atom or by an imino, N-alkylimino, N-arylimino, N-aralkylimino, N-formylimino, N-alkylcarbonylimino, N-alkylsulphonylimino, N-arylcarbonylimino, N-arylsulphonylimino, N-aralkylcarbonylimino, N-alkoxycarbonylimino, N-cyanoimino, N-aminocarbonylimino, N-alkylaminocarbonylimino or N-dialkylaminocarbonylimino group, a 1-piperazinyl group which is optionally substituted by 1 to 2 alkyl groups and is substituted in position 4 by a pyridyl group, a 1-piperazinyl or 1-homopiperazinyl group which is optionally substituted by 1 to 2 alkyl groups and is in each case substituted on the 4-nitrogen atom by a $B_{11}$ $B_2$, $B_1$-alkyl, $B_2$-alkyl, $B_3$-alkyl, $B_4$-alkyl, $B_1$-carbonyl, $B_2$-carbonyl, $B_4$-carbonyl, $B_1$-aminocarbonyl, $B_2$-aminocarbonyl, N-($B_1$)-N-alkylaminocarbonyl, N-($B_2$)-N-alkylaminocarbonyl group in which $B_1$ represents a $C_{5-7}$-cycloalkyl group in which one methylene group is replaced by an oxygen or sulphur atom, by a sulphinyl, sulphonyl, imino, N-alkylimino, N-arylimino, N-alkylcarbonylimino, N-alkylsulphonylimino, N-arylcarbonylimino, N-formylimino, N-alkoxycarbonylimino or N-cyanoimino group, $B_2$ represents a $C_{5-7}$-cycloalkyl group which is substituted by the radical $R_{14}$ where $R_{14}$ is defined as mentioned above, $B_3$ is a 6- to 7-membered 1-alkyleneimino group in which the methylene group in position 4 is replaced by an oxygen or sulphur atom, by a sulphinyl, sulphonyl, imino, N-alkylimino, N-arylimino, N-alkylcarbonylimino, N-alkylsulphonylimino, N-arylcarbonylimino, N-formylimino, N-alkoxycarbonylimino or N-cyanoimino group, and $B_4$ represents a 5-7-membered 1-alkyleneimino group which is substituted by the radical $R_{14}$ where $R_{14}$ is defined as mentioned above, a 1-pyrrolidinyl group which is optionally substituted by 1 to 2 alkyl groups and is substituted in position 3 by a $B_1$-alkyl, $B_2$-alkyl, $B_4$-alkyl, $B_1$-oxy, $B_2$-oxy, $B_1$-amino, $B_2$-amino, N-($B_1$)-N-alkylamino, N-($B_2$)-N-alkylamino, $B_4$-carbonyl, $B_1$-aminocarbonyl, $B_2$-aminocarbonyl, N-($B_1$)-N-alkylaminocarbonyl, N-($B_2$)-N-alkylaminocarbonyl, $B_1$-carbonylamino, $B_2$-carbonylamino, $B_3$-carbonylamino, $B_4$-carbonylamino, N-($B_1$-carbonyl)-N-alkylamino, N-($B_2$-carbonyl)-N-alkylamino, N-($B_3$-carbonyl)-N-alkylamino, N-($B_4$-carbonyl)-N-alkylamino, $B_2$-aminoalkyl, N-($B_2$)-N-alkylaminoalkyl group, where $B_1$ to $B_4$ are defined as mentioned above, a 1-piperidinyl or 1-azacycloheptyl group which is optionally substituted by 1 to 2 alkyl groups and is substituted in position 3 or 4 by a $B_1$-alkyl, $B_2$-alkyl, $B_4$-alkyl, $B_1$-oxy, $B_2$-oxy, $B_1$-amino, $B_2$-amino, N-($B_1$)-N-alkylamino, N-($B_2$)-N-alkylamino, $B_4$-carbonyl, $B_1$-aminocarbonyl, $B_2$-aminocarbonyl, N-($B_1$)-N-alkylaminocarbonyl, N-($B_2$)-N-alkylaminocarbonyl, $B_1$-carbonylamino, $B_2$-carbonylamino, $B_3$-carbonylamino, $B_4$-carbonylamino, N-($B_1$-carbonyl)-N-alkylamino, N-($B_2$-carbonyl)-N-alkylamino, N-($B_3$-carbonyl)-N-alkylamino, N-($B_4$-carbonyl)-N-alkylamino, $B_2$-aminoalkyl, N-($B_2$)-N-alkylaminoalkyl group, where $B_1$ to $B_4$ are defined as mentioned above, an ($R_{15}NR_{16}$) group in which $R_{15}$ denotes a hydrogen atom or an alkyl group, $R_{16}$ denotes a 3-pyrrolidinyl, 3- or 4-piperidinyl or 3- or 4-azacycloheptyl group which is optionally substituted by 1 to 2 alkyl groups and is substituted in position 1 by a $B_1$, $B_2$, $B_1$-alkyl, $B_2$-alkyl, $B_3$-alkyl, $B_4$-alkyl, $B_1$-carbonyl, $B_2$-carbonyl, $B_4$-carbonyl, $B_1$-aminocarbonyl, $B_2$-aminocarbonyl, N-($B_1$)-N-alkylaminocarbonyl, N-($B_2$)-N-alkylaminocarbonyl group, where $B_1$ to $B_4$ are defined as mentioned above, a $C_{5-7}$-cycloalkyl group which is optionally substituted by 1 to 2 methyl groups and is substituted by a $B_1$-alkyl, $B_2$-alkyl, $B_4$-alkyl, $B_1$-oxy, $B_2$-oxy, $B_1$-amino, $B_2$-amino, N-($B_1$)-N-alkylamino, N-($B_2$)-N-alkylamino, $B_4$-carbonyl, $B_1$-aminocarbonyl, $B_2$-aminocarbonyl, N-($B_1$)-N-alkylaminocarbonyl, N-($B_2$)-N-alkylaminocarbonyl, $B_1$-carbonylamino, $B_2$-carbonylamino, $B_3$-carbonylamino, $B_4$-carbonylamino, N-($B_1$-carbonyl)-N-alkylamino, N-($B_2$-carbonyl)-N-alkylamino, N-($B_3$-carbonyl)-N-alkylamino, N-($B_4$-carbonyl)-N-alkylamino, $B_2$-aminoalkyl, N-($B_2$)-N-alkylaminoalkyl group, where $B_1$ to $B_4$ are defined as mentioned above, a $C_{2-4}$-alkyl group which is substituted by a 1-azetidinyl group which is optionally substituted by an alkyl group and in which two hydrogen atoms of a methylene group are replaced by a straight-chain $C_{4-6}$-alkylene bridge, where in each case one methylene group in the bicyclic ring formed in this way is replaced by an $R_{13}N$ group where $R_{13}$ is defined as mentioned above, the bicyclic ring formed in this way is substituted by the radical $R_{14}$ where $R_{14}$ is defined as mentioned above, a $C_{2-4}$-alkyl group which is substituted by a 1-pyrrolidinyl, 1-piperidinyl or 1-Azacyclohept-1-yl group which is optionally substituted by 1 to 2 alkyl groups and in which two hydrogen atoms of a methylene group are replaced by a straight-chain $C_{3-6}$-alkylene bridge, where in each case one methylene group in the bicyclic rings formed in this way is replaced by an $R_{13}N$ group, where $R_{13}$ is defined as mentioned above, or the bicyclic rings formed in this way are substituted by the radical $R_{14}$ where $R_{14}$ is defined as mentioned above, an alkylamino group whose alkyl moiety can optionally be substituted by a hydroxyl group, a 1-piperidinyl group whose 4-methylene group is replaced by an oxygen atom or by an imino or N-alkylimino group, an alkyl group which is substituted by a pyridyl group or a phenyl group which is substituted by an aminomethyl group, a $C_{2-4}$-alkyl group which is substituted by a 5- to 7-membered 1-alkyleneimino group which is substituted by the radical $R_{14}$, a 1-piperazinylcarbonylalkyl group which is substituted in position 4 of the piperazinyl moiety by a formyl or alkoxycarbonyl group, an alkylcarbonyl, alkoxycarbonyl or arylcarbonyl group, an (alkyleneimino)carbonyl group with, in each case, 5 to 7 ring atoms in the alkyleneimino moiety, it being possible in each of the abovementioned 6- to 7-membered alkyleneimino moieties for one methylene group in position 4 to be replaced by an oxygen or sulphur atom, by a sulphinyl, sulphonyl, imino, N-alkylimino, N-alkylcarbonylimino, N-formylimino, N-alkoxycarbonylimino, N-alkylsulphonylimino, N-arylimino or N-aralkylimino group, a 3-pyrrolidinyl, 3- or 4-piperidinyl or 3- or 4-azacycloheptyl group which is substituted in position 1 by a trifluoroacetyl group, a $C_{5-7}$-cycloalkyl group which is optionally substituted by 1 to 2 methyl groups and is substituted by an alkoxycarbonylaminoalkyl, N-(alkoxycarbonyl)-N-alkylamino-alkyl, (2-hydroxyethyl)aminocarbonyl, (2-alkoxyethyl)aminocarbonyl, (2-amino-5ethyl) aminocarbonyl, carboxyalkylamino or alkoxycarbonylalkylamino group, a $C_{5-7}$-cycloalkyl group which is optionally substituted by 1 to 2 methyl groups and in which one methylene group is replaced by an imino, N-alkylimino, N-arylimino, N-alkylcarbonylimino, N-alkylsulphonylimino, N-arylcarbonylimino or N-alkoxycarbonylimino group, and where in each case two hydrogen atoms in the cycloalkyl moiety are replaced by a straight-chain alkylene bridge, where this bridge contains 2 to 6 carbon atoms when the two hydrogen atoms are located on the same carbon atom, or contains 1 to 5 carbon atoms when the two hydrogen atoms are located on adjacent carbon atoms, or contains 2 to 4 carbon atoms when the two hydrogen atoms are located on carbon atoms separated by one atom, a phenyl group which is substituted by an (alkyleneimino) carbonyl group with, in each case, 5 to 7 ring atoms in the alkyleneimino moiety, it being possible in each of the abovementioned 6- to 7-membered alkyleneimino moieties for one methylene group in position 4 to be replaced by an oxygen or sulphur atom, by a sulphinyl, sulphonyl, imino, N-alkylimino, N-alkylcarbonylimino, N-formylimino, N-alkoxycarbonylimino, N-alkylsulphonylimino, N-arylimino or N-aralkylimino group, a phenyl group which is substituted by a 3-oxo-1-piperazinyl group which is optionally substituted in position 1 by an alkyl group and optionally in addition substituted by 1 to 2 alkyl groups, where the abovementioned phenyl radicals can in each case be substituted by a fluorine, chlorine or bromine atom, by a nitro, alkyl, alkoxy, trifluoromethyl or hydroxyl group and, unless otherwise mentioned, the abovementioned alkyl, alkylene and alkoxy moieties each contain 1 to 4 carbon atoms, and, unless otherwise mentioned, each carbon atom in the abovementioned alkyleneimino, alkylene or cycloalkylene moieties which is bonded to a nitrogen, oxygen or sulphur atom cannot be bonded to another halogen, nitrogen, oxygen or sulphur atom.

Preferred compounds of the above general formula I are, with the proviso that at least (i) $A_2$ represents a methyl group,
(ii) $A_8$ represents a methyl group,
(iii) $A_4$ represents an $R_dNR_e$ group or
(iv) $A_6$ represents an $R_g$ group, those in which $A_2$ and $A_8$, which can be identical or different, each denote a hydrogen atom or an alkyl group, $A_4$ denotes an $R_aNR_b$ group or an $R_dNR_e$ group and
$A_6$ denotes an $R_c$ group or an $R_g$ group in which
$R_a$ denotes a hydrogen atom,
$R_b$ denotes a phenyl group which is substituted by the radicals $R_1$ to $R_3$ where
$R_1$ denotes a hydrogen, fluorine, chlorine, bromine or iodine atom,
an ethynyl, alkyl, hydroxyl or methoxy group,
a phenyl, phenoxy, phenylalkyl, phenylalkoxy, nitro or cyano group,
a methyl or methoxy group which is substituted by 1 to 3 fluorine atoms,
an ethyl or ethoxy group which is substituted by 1 to 5 fluorine atoms,
$R_2$ denotes a hydrogen, fluorine, chlorine or bromine atom, a methyl, trifluoromethyl, amino, methylamino, dimethylamino, acetylamino or methoxy group,
$R_3$ denotes a hydrogen, fluorine, chlorine or bromine atom, and
$R_c$ a 1-pyrrolidinyl group which can be substituted by 1 to 2 methyl groups, by one carboxyl, hydroxyalkyl, aminoalkyl, alkylaminoalkyl, dialkylaminoalkyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 by a hydroxyl, alkoxy, amino, alkylamino, dialkylamino, alkylcarbonylamino, alkoxycarbonylamino, formylamino, cyanamino, alkylsulphonylamino, dialkylaminocarbonylamino, N-alkyldialkylaminocarbonylamino or cyano group, a 1-piperidinyl group which can be substituted by 1 to 2 methyl groups, by one hydroxyalkyl, aminoalkyl, alkylaminoalkyl, dialkylaminoalkyl, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 or 4 also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyldialkylaminocarbonylamino or cyano group, a 1-piperidinyl group which is optionally substituted by 1 or 2 methyl groups and in which the methylene group in position 4 is replaced by an oxygen or sulphur atom, by a carbonyl, sulphinyl, sulphonyl, imino, alkylimino, amino-$C_{2-4}$-alkylimino, alkylamino-$C_{2-4}$-alkylimino, dialkylamino-$C_{2-4}$-alkylimino, alkylcarbonylimino or alkylsulphonylimino group, a 1-azacyclohept-1-yl group which is optionally substituted by 1 or 2 methyl groups and in which in each case the methylene group in position 4 can be replaced by an oxygen atom, by an imino, N-alkylimino, N-alkylcarbonylimino or N-alkylsulphonylimino group, or a 5- to 7-membered alkyleneimino group which is optionally substituted by 1 or 2 methyl groups and is linked via a carbon atom to a carbon atom of a 5- to 7-membered alkyleneimino group in which the nitrogen atom can be substituted by a methyl group, an ($R_4NR_5$) group, in which
$R_4$ denotes a hydrogen atom or an alkyl group and
$R_5$ denotes a hydrogen atom, a $C_{1-6}$-alkyl group which can be substituted by a hydroxyl, alkoxy, cyano, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl, 4-alkyl-1-piperazinylcarbonyl, amino, formylamino, alkylamino, dialkylamino, alkylcarbonylamino, N-alkylalkylcarbonylamino, alkoxycarbonylamino, N-alkylalkoxycarbonylamino, alkylsulphonylamino, N-alkyl-alkylsulphonylamino, 1-pyrrolidinyl, 2-oxo-1-pyrrolidinyl, 1-piperidinyl, 2-oxo-1-piperidinyl, morpholino, 1-piperazinyl, 4-alkyl-1-piperazinyl, 4-alkylcarbonyl-1-piperazinyl, 4-alkylsulphonyl-1-piperazinyl, 4-alkoxycarbonyl-1-piperazinyl, 4-cyano-1-piperazinyl, 4-formyl-1-piperazinyl, 4-aminocarbonyl-1-piperazinyl, 4-alkylaminocarbonyl-1-piperazinyl or 4-dialkylaminocarbonyl-1-piperazinyl or an ($R_8NR_7$)—CO—$NR_6$ group where
$R_6$, $R_7$ and $R_8$, which can be identical or different, each represent a hydrogen atom or an alkyl group or
$R_6$ and $R_7$ together represent an n-$C_{2-4}$-alkylene group and
$R_8$ represents a hydrogen atom or an alkyl group, a $C_{3-6}$-alkyl group which is substituted by 2 to 5 hydroxyl groups, a phenyl group which is substituted in position 4 by an alkylcarbonylamino, N-alkyl-alkylcarbonylamino or by an ($R_8NR_7$)—CO—$NR_6$— group where $R_6$ to $R_8$ are defined as mentioned above, a phenyl group which is substituted in position 4 by a 1-pyrrolidinyl, 1-piperidinyl, 2-oxo-1-pyrrolidinyl, 2-oxo-1-piperidinyl, morpholino, 1-piperazinyl or 4-alkyl-1-piperazinyl group, a $C_{3-7}$-cycloalkyl group which can be substituted by a carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, a $C_{5-7}$-cycloalkyl group which is optionally substituted by 1 or 2 methyl groups and is substituted by one hydroxymethyl, cyano, hydroxyl, alkoxy, amino, alkylamino, dialkylamino, alkoxycarbonylamino, N-alkyl-alkoxycarbonylamino, alkylcarbonylamino, N-alkyl-alkylcarbonylamino, alkylsulphonylamino, N-alkylalkylsulphonylamino or by an ($R_8NR_7$)—CO—$NR_6$— group where $R_6$ to $R_8$ are defined as mentioned above, a $C_{5-7}$-cycloalkyl group which is optionally substituted by 1 or 2 methyl groups and is substituted by a 1-pyrrolidinyl, 1-piperidinyl, 2-oxo-1-pyrrolidinyl, 2-oxo-1-piperidinyl, morpholino, 1-piperazinyl, 4-alkyl-1-piperazinyl or 4-alkylcarbonyl-1-piperazinyl group, a tetrahydrofurfuryl group, a cyclopentyl group in which the methylene group in position 3 is replaced by an oxygen atom, an imino, alkylimino, alkylcarbonylimino, formylimino, aminocarbonylimino, alkylaminocarbonylimino, alkoxycarbonylimino, alkylsulphonylimino, dialkylaminocarbonylimino or cyanoimino group, a cyclohexyl group in which the methylene group in position 3 is replaced by an imino, alkylimino, alkylcarbonylimino, alkoxycarbonylimino or alkylsulphonylimino group, a cyclohexyl group in which the methylene group in position 4 is replaced by an oxygen atom, an imino, N-alkylimino, N-formylimino, N-alkylcarbonylimino, N-alkoxycarbonylimino, N-cyanoimino, N-aminocarbonylimino, N-alkylaminocarbonylimino, N,N-dialkylaminocarbonylimino or N-alkylsulphonylimino group, a cyclohexyl group which is optionally substituted by 1 to 2 methyl groups and is substituted in position 4 by a carboxymethoxy, methoxycarbonylmethoxy, aminocarbonylmethoxy, alkylaminocarbonylmethoxy, dialkylaminocarbonylmethoxy, 1-pyrrolidinylcarbonylmethoxy, 1-piperidinylcarbonylmethoxy, morpholinocarbonylmethoxy, carboxyalkyl, alkoxycarbonylalkyl, aminocarbonylalkyl, alkylaminocarbonylalkyl, dialkylaminocarbonylalkyl, 1-pyrrolidinylcarbonylalkyl, 1-piperidinylcarbonylalkyl or morpholinocarbonylalkyl group, a cyclohexylmethyl group where the cyclohexyl moiety is substituted by a carboxyl, aminocarbonyl, alkylaminocarbonyl, dialkylaminocarbonyl, 1-pyrrolidinylcarbonyl, 1-piperidinylcarbonyl, morpholinocarbonyl or alkoxycarbonyl group, a 3- or 4-quinuclidinyl group, $R_d$ denotes a hydrogen atom, $R_e$ denotes a fluorenyl group, a phenyl-$C_{1-4}$-alkyl, 1,2,3,4-tetrahydro-1-naphthyl or 1,2,3,4-tetrahydro-2-naphthyl group in which the aromatic moieties can each be monosubstituted by a fluorine, chlorine, bromine or iodine atom or an amino, alkyl, trifluoromethyl, ethynyl, methoxy, cyclopropyl, trifluoromethoxy, cyano, methoxycarbonyl or nitro group or disubstituted by fluorine, chlorine or bromine atoms, an indolyl, indazolyl, quinolyl, isoquinolyl, 2,1,3-benzothiadiazolyl, thiazolyl, benzothiazolyl or pyridyl group which can be substituted in the carbon framework by an alkyl group and additionally by a fluorine, chlorine or bromine atom, by a methyl, methoxy, hydroxyl, phenyl, nitro, amino, alkylamino, dialkylamino, alkylcarbonylamino, cyano, carboxyl, alkoxycarbonyl, aminocarbonyl, alkylaminocarbonyl, dialkylaminocarbonyl, trifluoromethyl, alkylcarbonyl, aminosulphonyl, alkylaminosulphonyl or dialkylaminosulphonyl group and where the abovementioned heterocyclic systems are bonded via a carbon atom to the nitrogen atom of the $R_dNR_e$ group, $R_g$ denotes a 1-azetidinyl group which is optionally substituted by a methyl group and in which the two hydrogen atoms of a methylene group are replaced by a straight-chain $C_{4-6}$-alkylene bridge, where in each case one methylene group in this $C_{4-6}$-alkylene bridge is replaced by an $R_{13}N$ group, where $R_{13}$ is a hydrogen atom or an alkyl, formyl, alkylcarbonyl, alkylsulphonyl, alkoxycarbonyl, cyano, aminocarbonyl, alkylaminocarbonyl or dialkylaminocarbonyl group, or where this $C_{4-6}$-alkylene bridge is substituted by a hydroxyl, alkoxy, amino, alkylamino or dialkylamino group, $R_g$ denotes a 1-pyrrolidinyl, 1-piperidinyl or 1-azacyclohept-1-yl group which is optionally substituted by 1 to 2 methyl groups and in which the two hydrogen atoms of a methylene group are replaced by a straight-chain $C_{3-6}$-alkylene bridge, where in each case one methylene group in this $C_{3-6}$-alkylene bridge is replaced by an $R_{13}N$ group, where $R_{13}$ is defined as mentioned above, or this $C_{3-6}$-alkylene bridge is substituted by a hydroxyl, alkoxy, amino, alkylamino or dialkylamino group, a 5- to 7-membered alkyleneimino group which is optionally substituted by 1 to 2 methyl groups and is linked via a carbon atom to a carbon atom of a 5- to 7-membered alkyleneimino group in which the nitrogen atom is substituted by an alkylcarbonyl, alkylsulphonyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, a 1-piperidinyl group which is linked in position 4 via a straight-chain $C_{2-4}$-alkylene bridge to a 4-piperidinyl or 1-methyl-4-piperidinyl group, a 1-piperidinyl group which is optionally substituted by 1 to 2 methyl groups and is substituted by a 3-oxo-1-piperazinylcarbonyl group which is optionally substituted in position 4 by an alkyl group, a 5- to 7-membered alkyleneimino group which is substituted by a pyridyl group and optionally in addition by 1 to 2 methyl groups, a 3-oxo-1-piperazinyl group which is optionally substituted in position 1 by an alkyl group and optionally in addition by 1 to 2 methyl groups, a 1-imidazolyl group which is optionally substituted by 1 to 2 methyl groups, a 1-piperazinyl group which is optionally substituted by 1 to 2 methyl groups and is substituted in position 4 by a pyridyl group, a 1-piperazinyl or 1-homopiperazinyl group which is optionally substituted by 1 to 2 methyl groups and is in each case substituted in position 4 by an (alkyleneimino)carbonylalkyl group with, in each case, 5 to 7 ring atoms in the alkyleneimino moiety, it being possible for a methylene group in position 4 in a 6- to 7-membered alkyleneimino moiety to be replaced by an oxygen atom or by an imino, N-alkylimino, N-formylimino, N-alkylcarbonylimino, N-alkylsulphonylimino, N-alkoxycarbonylimino, N-cyanoimino, N-aminocarbonylimino, N-alkylaminocarbonylimino or N-dialkylaminocarbonylimino group, a 1-piperazinyl or 1-homopiperazinyl group which is optionally substituted by 1 to 2 methyl groups and is substituted in each case on the 4-nitrogen atom by a cyclopentyl group in which the 3-methylene group is replaced by an oxygen atom or an $R_{13}N$ group where $R_{13}$ is defined as mentioned above, a 1-piperazinyl or 1-homopiperazinyl group which is optionally substituted by 1 to 2 methyl groups and is in each case substituted on the 4-nitrogen atom by a cyclohexyl group in which the 4-methylene group is replaced by an oxygen atom or an $R_{13}N$ group where $R_{13}$ is defined as mentioned above, a 1-piperazinyl or 1-homopiperazinyl group which is optionally substituted by 1 to 2 methyl groups and is in each case substituted on the 4-nitrogen atom by a cyclohexyl group which is substituted in position 4 by the radical $R_{14}$ where $R_{14}$ represents a hydroxyl, alkoxy, amino, alkylamino, dialkylamino, alkylcarbonylamino, alkylsulphonylamino, alkoxycarbonylamino, carboxyl, alkoxycarbonyl, aminocarbonyl, alkylaminocarbonyl or dialkylaminocarbonyl group, a 1-pyrrolidinyl group which is optionally substituted by 1 to 2 methyl groups and is substituted in position 3 by a cyclohexylamino group whose 4-methylene group is replaced by an oxygen atom or an $R_{13}N$ group where $R_{13}$ is defined as mentioned above, or which is substituted in position 4 by the radical $R_{14}$ where $R_{14}$ is defined as mentioned above, a 1-pyrrolidinyl group which is optionally substituted by 1 to 2 methyl groups and is substituted in position 3 by a 1-piperidinylcarbonylamino group whose 4-methylene group is replaced by an oxygen atom or an $R_{13}N$ group where $R_{13}$ is defined as mentioned above, a 1-piperidinyl group which is optionally substituted by 1 to 2 methyl groups and is substituted in position 4 by a cyclohexylmethyl group whose 4-methylene group is replaced by an oxygen atom or an $R_{13}N$ group where $R_{13}$ is defined as mentioned above, or by a cyclohexylamino group whose 4-methylene group is replaced by an oxygen atom or an $R_{13}N$ group where $R_{13}$ is defined as mentioned above, or by a cyclohexylamino or cyclohexylaminomethyl group which is substituted in position 4 by the radical $R_{14}$ where $R_{14}$ is defined as mentioned above, a 1-piperidinyl group which is optionally substituted by 1 to 2 methyl groups and is substituted in position 4 by a 1-piperidinylcarbonylamino group whose 4-methylene group is replaced by an oxygen atom or an $R_{13}N$ group where $R_{13}$ is defined as mentioned above, a 1-piperidinyl group which is optionally substituted by 1 to 2 methyl groups and is substituted in position 4 by a 1-piperidinylmethyl or 1-piperidinylcarbonyl group which is substituted in position 4 by the radical $R_{14}$ where $R_{14}$ is defined as mentioned above, an $(R_{15}NR_{16})$ group in which $R_{15}$ denotes a hydrogen atom or an alkyl group, $R_{16}$ denotes a 3-pyrrolidinyl or 4-piperidinyl group which is optionally substituted by 1 to 2 methyl groups and is substituted in position 1 by a cyclopentyl group whose 3-methylene group is replaced by an oxygen atom or an $R_{13}N$ group or by a cyclohexyl group whose 4-methylene group is replaced by an oxygen atom or an $R_{13}N$ group, or which is substituted in position 4 by the radical $R_{14}$ where $R_{13}$ and $R_{14}$ are defined as mentioned above, a cyclopentyl group which is optionally substituted by 1 to 2 methyl groups and is substituted in position 3 by a 1-piperidinylcarbonylamino group whose 4-methylene group is replaced by an oxygen atom or an $R_{13}N$ group where $R_{13}$ is defined as mentioned above, a cyclohexyl group which is optionally substituted by 1 to 2 methyl groups and is substituted in position 3 or 4 by a 1-piperidinylcarbonylamino group whose 4-methylene group is replaced by an oxygen atom or an $R_{13}N$ group where $R_{13}$ is defined as mentioned above, a cyclohexyl group which is optionally substituted by 1 to 2 methyl groups and is substituted in position 4 by a cyclohexylmethyl, cyclohexylamino, cyclohexylaminocarbonyl or N-(cyclohexyl)-N-alkylaminocarbonyl group whose 4-methylene group is replaced by an oxygen atom or an $R_{13}N$ group where $R_{13}$ is defined as mentioned above, a cyclohexyl group which is optionally substituted by 1 to 2 methyl groups and is substituted in position 4 by a cyclohexylmethyl, cyclohexylamino or cyclohexylaminocarbonyl group which is substituted in position 4 by the radical $R_{14}$ where $R_{14}$ is defined as mentioned above, a cyclohexyl group which is optionally substituted by 1 to 2 methyl groups and is substituted in position 4 by a 1-piperidinylmethyl or 1-piperidinylcarbonyl group which is substituted in position 4 by the radical $R_{14}$ where $R_{14}$ is defined as mentioned above, a cyclohexyl group which is optionally substituted by 1 to 2 methyl groups and is substituted in position 4 by a cyclohexylaminomethyl group which is substituted in position 4 by the radical $R_{14}$ where $R_{14}$ is defined as mentioned above, an ethyl group which is substituted in position 2 by a 1-azetidinyl group which is optionally substituted by an alkyl group and in which two hydrogen atoms of a methylene group are replaced by a straight-chain $C_{4-6}$-alkylene bridge, where in each case a methylene group in this $C_{4-6}$-alkylene bridge is replaced by an $R_{13}N$ group where $R_{13}$ is defined as mentioned above, an ethyl group which is substituted in position 2 by a 1-pyrrolidinyl, 1-piperidinyl or 1-azacyclohept-1-yl group which is optionally substituted by 1 to 2 alkyl groups and in which two hydrogen atoms of a methylene group are replaced by a straight-chain $C_{3-6}$-alkylene bridge, where in each case a methylene group in this $C_{3-6}$-alkylene bridge is replaced by an $R_{13}N$ group where $R_{13}$ is defined as mentioned above, a 4-morpholinyl group, an alkyl group which is substituted by a pyridyl group or by a phenyl group which is substituted by an aminomethyl group, a $C_{2-4}$-alkyl group which is substituted by a 1-piperidinyl group which is substituted by the radical $R_{14}$, a 1-piperazinylcarbonylalkyl group which is substituted in position 4 of the piperazinyl moiety by a formyl or alkoxycarbonyl group, an alkylcarbonyl group, an (alkyleneimino)carbonyl group with, in each case, 5 to 7 ring atoms in the alkyleneimino moiety, it being possible for the methylene group in position 4 in each of the abovementioned 1-piperidinyl moieties to be replaced by an oxygen atom or by an imino or N-alkylimino group, a 3-pyrrolidinyl, 3- or 4-piperidinyl or 3- or 4-azacycloheptyl group which is substituted in position 1 by a trifluoroacetyl group, a cyclohexyl group which is optionally substituted by 1 to 2 methyl groups and is substituted by a $C_{1-4}$-alkoxycarbonylaminoalkyl, N-($C_{1-4}$-alkoxycarbonyl)-N-alkylaminoalkyl, (2-hydroxyethyl)aminocarbonyl, (2-alkoxyethyl)aminocarbonyl, (2-aminoethyl)aminocarbonyl, carboxy-$C_{1-4}$-alkylamino or alkoxycarbonyl-$C_{1-4}$-alkylamino group, a cyclohexyl group which is optionally substituted by 1 to 2 methyl groups and in which one methylene group is replaced by an imino, N-alkylimino, N-arylimino, N-alkylcarbonylimino, N-alkylsulphonylimino, N-arylcarbonylimino or N-alkoxycarbonylimino group and where in each case two hydrogen atoms in the cycloalkyl moiety are replaced by a straight-chain alkylene bridge, where this bridge contains 2 to 4 carbon atoms and the two hydrogen atoms are located on carbon atoms separated by one atom, a phenyl group which is substituted by an (alkyleneimino) carbonyl group with in each case 5 to 7 ring atoms in the alkyleneimino moiety, it being possible for the methylene group in position 4 of each of the abovementioned 1-piperidinyl moieties to be replaced by an oxygen atom or by an imino or N-alkylimino group, a phenyl group which is substituted in position 4 by a 3-oxo-1-piperazinyl group which is optionally substituted in position 4 by a methyl group and optionally additionally by 1 to 2 methyl groups, their tautomers, their stereoisomers and their salts, where, unless otherwise mentioned, the abovementioned alkyl, alkylene and alkoxy moieties each contain 1 to 2 carbon atoms, and, unless otherwise mentioned, each carbon atom in the abovementioned alkylene or cycloalkylene moieties which is bonded to a nitrogen, oxygen or sulphur atom cannot be bonded to another halogen, nitrogen, oxygen or sulphur atom.

Particularly preferred compounds of the above general formula I are, with the proviso that at least (i) $A_2$ represents a methyl group,
(ii) $A_8$ represents a methyl group,
(iii) $A_4$ represents an $R_dNR_e$ group or
(iv) $A_6$ represents an $R_g$ group, those in which $A_2$ and $A_8$, which can be identical or different, each denote a hydrogen atom or an alkyl group, $A_4$ denotes an $R_aNR_b$ group or an $R_dNR_e$ group and
$A_6$ denotes an $R_c$ group or an $R_g$ group in which
$R_a$ denotes a hydrogen atom,
$R_b$ b denotes a phenyl group substituted by the radicals $R_1$ to $R_3$, where
$R_1$ denotes a hydrogen, fluorine, chlorine, bromine or iodine atom,
an ethynyl, alkyl, phenoxy or methoxy group,
a nitro or cyano group,
a methyl or methoxy group which is substituted by 1 to 3 fluorine atoms,
$R_2$ denotes a hydrogen, fluorine, chlorine or bromine atom or an amino group,
$R_3$ denotes a hydrogen, fluorine, chlorine or bromine atom, and $R_c$ denotes a 1-pyrrolidinyl group which can be substituted in position 3 by an aminomethyl, methylaminomethyl, dimethylaminomethyl, hydroxyl, methoxy, amino, methylamino, dimethylamino, methylcarbonylamino, methoxycarbonylamino, formylamino, cyanoamino, methylsulphonylamino, dimethylaminocarbonylamino, N-methyl-dimethylaminocarbonylamino or cyano group, a 1-piperidinyl group which can be substituted in position 3 or 4 by an aminomethyl, methylaminomethyl, dimethylaminomethyl, carboxyl, methoxycarbonyl, aminocarbonyl, methylaminocarbonyl, dimethylaminocarbonyl, 1-pyrrolidinylcarbonyl, 1-piperidinylcarbonyl, morpholinocarbonyl, 1-piperazinylcarbonyl, 4-methyl-1-piperazinylcarbonyl, hydroxyl, methoxy, amino, methylamino, dimethylamino, alkylcarbonylamino, methoxycarbonylamino, formylamino, cyanoamino, methylsulphonylamino, dimethylaminocarbonylamino, N-methyl-dimethylaminocarbonylamino or cyano group, a 1-piperidinyl group in which the methylene group in position 4 is replaced by an oxygen or sulphur atom, by an imino, N-alkylimino, N-amino-$C_{2-4}$-alkylimino, alkylamino-$C_{2-4}$-alkylimino, dialkylamino-$C_{2-4}$-alkylimino, alkylcarbonylimino or alkylsulphonylimino group, a 1-piperidinyl group which is linked via a carbon atom to a carbon atom of a 5- to 7-membered alkyleneimino group in which the nitrogen atom can be substituted by a methyl group, an ($R_4NR_5$) group in which
$R_4$ denotes a hydrogen atom or an alkyl group, and
$R_5$ denotes a hydrogen atom, a $C_{1-4}$-alkyl group, which can be substituted by a hydroxyl, methoxy, cyano, carboxyl, methoxycarbonyl, aminocarbonyl, methylaminocarbonyl, dimethylaminocarbonyl, 1-pyrrolidinylcarbonyl, 1-piperidinylcarbonyl, morpholinocarbonyl, 1-piperazinylcarbonyl, 4-methyl-1-piperazinylcarbonyl, amino, formylamino, methylamino, dimethylamino, acetylamino, methoxycarbonylamino, methylsulphonylamino, 1-pyrrolidinyl, 2-oxo-1-pyrrolidinyl, 1-piperidinyl, 2-oxo-1-piperidinyl, morpholino, 1-piperazinyl or 4-methyl-1-piperazinyl group, a phenyl group which is substituted in position 4 by an acetylamino or by an ($R_8NR_7$)—CO—$NR_6$ group where $R_6$ to $R_8$ are defined as mentioned above, a cyclopropyl group, a cyclohexyl group which is substituted by a carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl, 4-alkyl-1-piperazinylcarbonyl, hydroxyl, alkoxy, amino, alkylamino, dialkylamino, alkoxycarbonylamino, alkylcarbonylamino, N-alkylalkylcarbonylamino, alkylsulphonylamino, 1-pyrrolidinyl, 1-piperidinyl, 2-oxo-1-pyrrolidinyl, 2-oxo-1-piperidinyl, morpholino, 1-piperazinyl, 4-methyl-1-piperazinyl or 4-acetyl-1-piperazinyl group, a cyclopentyl group in which the methylene group in position 3 is replaced by an imino or N-alkylimino group, a cyclohexyl group in which the methylene group in position 3 or 4 is replaced by an imino or N-alkylimino group, a 3-quinuclidinyl group, $R_d$ denotes a hydrogen atom,,
$R_e$ denotes a fluorenyl group, a phenyl-$C_{1-2}$-alkyl or 1,2,3,4-tetrahydro-2-naphthyl group in which the aromatic moieties can each be mono-substituted by a fluorine, chlorine, bromine or iodine atom or an amino, methyl, trifluoromethyl, methoxy, trifluoromethoxy, cyano, methoxycarbonyl or nitro group, an indolyl, indazolyl, quinolyl, isoquinolyl, 2,1,3-benzothiadiazolyl, thiazolyl, benzothiazolyl or pyridyl group which can be substituted in the carbon framework by a fluorine, chlorine or bromine atom, by a methyl, methoxy, hydroxyl, nitro, amino, methylamino, dimethylamino, cyano or trifluoromethyl group, and where the abovementioned heterocyclic systems are bonded via a carbon atom to the nitrogen atom of the $R_dNR_e$ group, $R_g$ denotes a 1-azetidinyl group which is optionally substituted by a methyl group and in which the two hydrogen atoms of the 3-methylene group are replaced by a straight-chain $C_{4-5}$-alkylene bridge, where, in each case, a methylene group in this $C_{4-5}$-alkylene bridge is replaced by an $R_{13}N$ group, where
$R_{13}$ represents a hydrogen atom or an alkyl, acetyl or methoxycarbonyl group, or where this $C_{4-5}$-alkylene bridge is substituted by a hydroxyl or amino group, $R_g$ denotes a 1-pyrrolidinyl or 1-piperidinyl group which is optionally substituted by 1 to 2 methyl groups and in which the two hydrogen atoms of a methylene group are replaced by a straight-chain $C_{3-6}$-alkylene bridge, where, in each case, a methylene group in this $C_{3-6}$-alkylene bridge is replaced by an $R_{13}N$ group where $R_{13}$ is defined as mentioned above, or where this $C_{3-6}$-alkylene bridge is substituted by a hydroxyl or amino group, a 1-piperidinyl group which is linked via a carbon atom to a carbon atom of a piperidinyl group in which the nitrogen atom is substituted by an alkylcarbonyl, alkylsulphonyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, a 1-piperidinyl group which is linked in position 4 via a straight-chain $C_{2-3}$-alkylene bridge to a 4-piperidinyl or 1-methyl-4-piperidinyl group, a 1-piperidinyl group which is substituted by a 3-oxo-1-piperazinylcarbonyl group which is optionally substituted in position 4 by an alkyl group, a 1-piperidinyl group which is substituted in position 4 by a pyridyl group a 3-oxo-1-piperazinyl group which is optionally substituted in position 1 by an alkyl group, a 1-imidazolyl group, a 1-piperazinyl group which is substituted in position 4 by a pyridyl group, a 1-piperazinyl or 1-homopiperazinyl group which is substituted in each case in position 4 by an (alkyleneimino) carbonylalkyl group with, in each case, 5 to 7 ring atoms in the alkyleneimino moiety, it being possible for a methylene group in position 4 of a 6- to 7-membered alkyleneimino moiety to be replaced by an oxygen atom or by an imino, N-alkylimino, N-alkylcarbonylimino or N-alkoxycarbonylimino group, a 1-piperazinyl or 1-homopiperazinyl group which is substituted in each case on the 4-nitrogen atom by a cyclopentyl group in which the 3-methylene group is replaced by an oxygen atom or an $R_{13}N$ group where $R_{13}$ is defined as mentioned above, a 1-piperazinyl or 1-homopiperazinyl group which is substituted in each case on the 4-nitrogen atom by a cyclohexyl group in which the 4-methylene group is replaced by an oxygen atom or an $R_{13}N$ group where $R_{13}$ is defined as mentioned above, a 1-piperazinyl or 1-homopiperazinyl group which is substituted in each case on the 4-nitrogen atom by a cyclohexyl group which is substituted in position 4 by the radical $R_{14}$, where $R_{14}$ represents a hydroxyl, alkoxy, amino, alkylamino, dialkylamino, alkylcarbonylamino, alkylsulphonylamino or alkoxycarbonylamino group, a 1-pyrrolidinyl group which is substituted in position 3 by a cyclohexylamino group whose 4-methylene group is replaced by an oxygen atom or an $R_{13}N$ group where $R_{13}$ is defined as mentioned above, or in position 4 by the radical $R_{14}$ where $R_{14}$ is defined as mentioned above, a 1-pyrrolidinyl group which is substituted in position 3 by a 1-piperidinylcarbonylamino group whose 4-methylene group is replaced by an oxygen atom or an $R_{13}N$ group where $R_{13}$ is defined as mentioned above, a 1-piperidinyl group which is substituted in position 4 by a cyclohexylmethyl group whose 4-methylene group is replaced by an oxygen atom or an $R_{13}N$ group, or by a cyclohexylamino group whose 4-methylene group is replaced by an oxygen atom or an $R_{13}N$ group, or by a cyclohexylamino or cyclohexylaminomethyl group which is substituted in position 4 by the radical $R_{14}$ where $R_{13}$ and $R_{14}$ are defined as mentioned above, a 1-piperidinyl group which is substituted in position 4 by a 1-piperidinylcarbonylamino group whose 4-methylene group is replaced by an oxygen atom or an $R_{13}N$ group where $R_{13}$ is defined as mentioned above, a 1-piperidinyl group which is substituted in position 4 by a 1-piperidinylmethyl or 1-piperidinylcarbonyl group which is substituted in position 4 by the radical $R_{14}$ where $R_{14}$ is defined as mentioned above, an ($R_{15}NR_{16}$) group in which $R_{15}$ denotes a hydrogen atom, $R_{16}$ denotes a 3-pyrrolidinyl or 4-piperidinyl group which is substituted in position 1 by a cyclopentyl group whose 3-methylene group is replaced by an oxygen atom or an $R_{13}N$ group, or by a cyclohexyl group whose 4-methylene group is replaced by an oxygen atom or an $R_{13}N$ group, or which is substituted in position 4 by the radical $R_{14}$, where $R_{13}$ and $R_{14}$ are defined as mentioned above, a cyclopentyl group which is substituted in position 3 by a 1-piperidinylcarbonylamino group whose 4-methylene group is replaced by an oxygen atom or an $R_{13}N$ group where $R_{13}$ is defined as mentioned above, a cyclohexyl group which is substituted in position 3 or 4 by a 1-piperidinylcarbonylamino group whose 4-methylene group is replaced by an oxygen atom or an $R_{13}N$ group where $R_{13}$ is defined as mentioned above, a cyclohexyl group which is substituted in position 4 by a cyclohexylmethyl, cyclohexylamino, cyclohexylaminocarbonyl or N-(cyclohexyl)-N-methylaminocarbonyl group whose 4-methylene group is replaced by an oxygen atom or an $R_{13}N$ group where $R_{13}$ is defined as mentioned above, a cyclohexyl group which is substituted in position 4 by a cyclohexylmethyl, cyclohexylamino or cyclohexylaminocarbonyl group which is substituted in position 4 by the radical $R_{14}$ where $R_{14}$ is defined as mentioned above, a cyclohexyl group which is substituted in position 4 by a 1-piperidinylmethyl or 1-piperidinylcarbonyl group which is substituted in position 4 by the radical $R_{14}$ where $R_{14}$ is defined as mentioned above, a cyclohexyl group which is substituted in position 4 by a cyclohexylaminomethyl group which is substituted in position 4 by the radical $R_{14}$ where $R_{14}$ is defined as mentioned above, an ethyl group which is substituted in position 2 by a 1-azetidinyl group in which two hydrogen atoms of a methylene group are replaced by a straight-chain $C_{4-6}$-alkylene bridge, where one methylene group in this $C_{4-6}$-alkylene bridge is replaced by an $R_{13}N$ group where $R_{13}$ is defined as mentioned above, an ethyl group which is substituted in position 2 by a 1-pyrrolidinyl or 1-piperidinyl group in which two hydrogen atoms of a methylene group are replaced by a straight-chain $C_{3-6}$-alkylene bridge, where in each case a methylene group in this $C_{3-6}$-alkylene bridge is replaced by an $R_{13}N$ group where $R_{13}$ is defined as mentioned above, a 4-morpholinyl group, an alkyl group which is substituted by a pyridyl group or by a phenyl group which is substituted by an aminomethyl group, an ethyl group which is substituted by a 1-piperidinyl group which is substituted by the radical $R_{14}$, a 1-piperazinylcarbonylalkyl group which is substituted in position 4 of the piperazinyl moiety by a formyl or methoxycarbonyl group, an alkylcarbonyl group, a 3-pyrrolidinyl or 3- or 4-piperidinyl group which is substituted in position 1 by a trifluoroacetyl group, or a cyclohexyl group which is substituted by a $C_{1-4}$-alkoxycarbonylaminoalkyl, (2-hydroxyethyl)

aminocarbonyl, (2-methoxyethyl)aminocarbonyl, carboxy-$C_{1-4}$-alkylamino or alkoxycarbonyl-$C_{1-4}$-alkylamino group, a cyclohexyl group in which a methylene group is replaced by an imino, N-alkylimino, N-alkylcarbonylimino or N-alkoxycarbonylimino group and where two hydrogen atoms in positions 3 and 5 of the cycloalkyl moiety are replaced by an ethylene bridge, a phenyl group which is substituted in position 4 by a 1-pyrrolidinylcarbonyl, 1-piperidinylcarbonyl or morpholinocarbonyl group, a phenyl group which is substituted in position 4 by a 3-oxo-1-piperazinyl group which is optionally substituted in position 4 by a methyl group, their tautomers, their stereoisomers and their salts, where, unless otherwise mentioned, the abovementioned alkyl, alkylene and alkoxy moieties each contain 1 to 2 carbon atoms, and, unless otherwise mentioned, each carbon atom in the abovementioned alkylene or cycloalkylene moieties which is bonded to a nitrogen, oxygen or sulphur atom cannot be bonded to another halogen, nitrogen, oxygen or sulphur atom.

Very particularly preferred compounds of the above general formula I are, with the proviso that at least (i) $A_2$ represents a methyl group,
(ii) $A_8$ represents a methyl group,
(iii) $A_4$ represents an $R_dNR_e$ group or
(iv) $A_6$ represents an $R_g$ group, those in which $A_2$ and $A_8$, which can be identical or different, each denote a hydrogen atom or a methyl group, $A_4$ denotes an $R_aNR_b$ group or an $R_dNR_e$ group and
$A_6$ denotes an $R_c$ group or an $R_g$ group in which
$R_a$ denotes a hydrogen atom
$R_b$ denotes a 3-methylphenyl, 4-amino-3,5-dibromophenyl, 4-phenoxyphenyl or 3-chloro-4-fluorophenyl group, $R_c$ denotes a morpholino, cyclopropylamino, trans-(4-hydroxycyclohexyl)amino, 4-amino-1-piperidinyl, 4-(4-piperidinyl)-1-piperidinyl, 4-(1-methyl-4-piperidinyl)-1-piperidinyl, 2-amino-2-methyl-1-propylamino, 4-piperidinylamino, 1-methyl-4-piperidinylamino, N-methyl-N-(1-methyl-4-piperidinyl)amino or trans-4-(morpholinocarbonyl)cyclohexylamino group, $R_d$ denotes a hydrogen atom, $R_e$ denotes a 5-indolyl, 5-quinolyl, 6-quinolyl, 8-quinolyl, 5-indazolyl, 6-indazolyl, 4-(2,1,3-benzothiadiazolyl), 2-thiazolyl, 2-methyl-5-benzothiazolyl, 2-pyridyl, 3-pyridyl, 4-pyridyl, 2-benzothiazolyl, 5-isoquinolyl, 6-isoquinolyl, 3-chlorobenzyl, 1,2,3,4-tetrahydro-2-naphthyl or 2-fluorenyl group, $R_g$ denotes 7-methyl-2,7-diazaspiro[3.5]-1-nonyl, 1,8-diazaspiro[4.5]-8-decyl, 3,9-diazaspiro[5.5]-3-undecyl, 2,7-diazaspiro[3.5]-2-nonyl, 2,7-diazaspiro[3.5]-7-nonyl, 2-methyl- 2,7-diazaspiro[4.4]-7-nonyl, 6-methyl-2,6-diazaspiro[3.4]-2-octyl or 2-methyl-2,6-diazaspiro[3.4]-6-octyl group, a 1-imidazolyl, 3-oxo-1-piperazinyl or 4-methyl-3-oxo-1-piperazinyl group, a 1-piperazinyl group which is substituted in position 4 by a 2-pyridyl, 4-pyridyl, 1-pyrrolidinylcarbonylmethyl, morpholinocarbonylmethyl, 4-piperidinyl, 1-methyl-4-piperidinyl, 1-acetyl-4-piperidinyl or 1-methoxycarbonyl-4-piperidinyl group, a 3-(morpholinocarbonylamino)-1-pyrrolidinyl group, a 1-piperidinyl group which is substituted in position 4 by a 1-acetyl-4-piperidinyl, 1-methoxycarbonyl-4-piperidinyl, 1-methylsulphonyl-4-piperidinyl, 1-(morpholinocarbonyl)-4-piperidinyl, 1-dimethylaminocarbonyl-4-piperidinyl, 3-oxo-1-piperazinylcarbonyl, 4-methyl-3-oxo-1-piperazinylcarbonyl, 4-pyridyl, trans-4-hydroxycyclohexylamino, 4-piperidinylamino, 4-piperidinylmethyl, morpholinocarbonylamino, (trans-4-hydroxycyclohexylamino)methyl, 4-amino-i-piperidinylmethyl, 4-methylamino-1-piperidinylmethyl, 4-dimethylamino-1-piperidinylmethyl or 4-ethylamino-1-piperidinylmethyl group, a 1-piperidinyl group which is linked in position 4 via a straight-chain $C_{2-3}$-alkylene bridge to a 4-piperidinyl or 1-methyl-4-piperidinyl group, a 1-piperidinyl group which is substituted in position 4 by a 1-methyl-4-piperidinylamino group, a 1-(4-aminocyclohexyl)-4-piperidinylamino group, a cyclopentylamino group which is substituted in position 3 by a morpholinocarbonylamino group, a cyclohexylamino group which is substituted in position 3 by a morpholinocarbonylamino group, a cyclohexylamino group which is substituted in position 4 by a 3-methoxycarbonyl-1-propylamino, trans-4-hydroxycyclohexylamino, 4-aminocyclohexylmethyl, morpholinocarbonylamino, (4-tetrahydropyranylamino) carbonyl, trans-4-hydroxycyclohexylaminocarbonyl, (4-amino-1-piperidinyl)carbonyl, (4-dimethylamino-1-piperidinyl)carbonyl, (4-piperidinylamino)carbonyl, N-(1-methyl-4-piperidinyl)-N-methylamino)carbonyl, (1-methyl-4-piperidinylamino)carbonyl, (4-dimethylamino-1-piperidinyl)methyl, (4-amino-1-piperidinyl)methyl, tert-butyloxycarbonylaminomethyl, (4-hydroxycyclohexylamino)methyl, 3-carboxypropylamino, 2-hydroxyethylaminocarbonyl or 2-methoxyethylaminocarbonyl group, a 4-piperidinylamino group which is substituted in position 1 by a 1-methyl-4-piperidinyl group, a (4-morpholinyl)amino group, a 2-(7-methyl-2,7-diazaspiro[4.4]-2-nonyl)ethylamino, 2-picolylamino, 4-picolylamino, 3-(aminomethyl)benzylamino or 4-(aminomethyl)benzylamino group, a 2-(4-amino-1-piperidinyl)ethylamino, 4-formyl-1-piperazinylcarbonylmethylamino, 4-methoxycarbonyl-1-piperazinylcarbonylmethylamino, 1-(4-formyl-1-piperazinylcarbonyl)ethylamino or 1-(4-methoxycarbonyl-1-piperazinylcarbonyl)ethylamino group, an acetylamino, 1-trifluoroacetyl-4-piperidinylamino or tropinylamino group, a 9-amino-3-azaspiro[5.5]-3-undecyl or 8-amino-2-azaspiro[4.5]-2-decyl group, a phenylamino group which is substituted in position 4 by a morpholinocarbonyl, 1-pyrrolidinylcarbonyl, 3-oxo-1-piperazinyl- or 4-methyl-3-oxo-1-piperazinyl group, especially those in which (i) $A_2$ represents a methyl group,
(ii) $A_8$ represents a methyl group,
(iii) $A_4$ represents an $R_dNR_e$ group or
(iv) $A_6$ represents an $R_g$ group, $A_2$ and $A_8$, which can be identical or different, each denote a hydrogen atom or a methyl group, $A_4$ denotes an $R_aNR_b$ group or an $R_dNR_e$ group and
$A_6$ denotes an $R_c$ group or an $R_g$ group, in which
$R_a$ denotes a hydrogen atom
$R_b$ denotes a 3-methylphenyl, 4-amino-3,5-dibromophenyl, 4-phenoxyphenyl or 3-chloro-4-fluorophenyl group, $R_c$ denotes a morpholino, cyclopropylamino, trans-(4-hydroxycyclohexyl)amino or 4-amino-1-piperidinyl group, R_d denotes a hydrogen atom, R_e denotes a 5-indolyl, 5-quinolyl, 6-quinolyl, 8-quinolyl, 5-indazolyl, 6-indazolyl, 4-(2,1,3-benzothiadiazolyl), 2-thiazolyl, 2-methyl-5-benzothiazolyl, 2-pyridyl, 3-pyridyl, 4-pyridyl, 2-benzothiazolyl, 5-isoquinolyl, 6-isoquinolyl, 3-chlorobenzyl, 1,2,3,4-tetrahydro-2-naphthyl or 2-fluorenyl group, R_g denotes a 7-methyl-2,7-diazaspiro[3,5]-1-nonyl, 2-methyl-2,7-diazaspiro[4.4]-7-nonyl, 6-methyl-2,6-diazaspiro[3.4]-2-octyl or 2-methyl-2,6-diazaspiro[3.4]-6-octyl group, a 4-(2-pyridyl)-1-piperazinyl, 4-(4-pyridyl)-1-piperazinyl, 3-oxo-1-piperazinyl, 1-imidazolyl, 4-(1-pyrrolidinylcarbonylmethyl)-1-piperazinyl, 4-(morpholinocarbonylmethyl)-1-piperazinyl, 4-(trans-4-hydroxycyclohexylamino)cyclohexylamino, 4-(4-aminocyclohexylmethyl)cyclohexylamino, 2-(7-methyl-2,7-diazaspiro[4.4]-2-nonyl)ethylamino, (4-morpholinyl)amino, 2-picolylamino, 4-picolylamino, 3-(aminomethyl)benzylamino, 4-(aminomethyl)benzylamino, acetylamino, 1-trifluoroacetyl-4-piperidinylamino or tropinylamino group, a 1-pyrrolidinyl group which is substituted in position 3 by a morpholinocarbonylamino group, a 4-piperidinylamino group which is substituted in position 1 by a 1-methyl-4-piperidinyl group, a 1-piperidinyl group which is substituted in position 4 by a 4-pyridyl, morpholinocarbonylamino, 1-methyl-4-piperidinylamino, 4-piperidinylamino, 1-acetyl-4-piperidinyl or 1-methoxycarbonyl-4-piperidinyl group, a 1-piperidinyl group which is linked in position 4 via a straight-chain C_{2-3}-alkylene bridge to a 4-piperidinyl or 1-methyl-4-piperidinyl group, a cyclohexylamino group which is substituted in position 4 by a 2-methoxyethylaminocarbonyl, (4-tetrahydropyranylamino)carbonyl, trans-4-hydroxycyclohexylaminocarbonyl, tert-butyloxycarbonylaminomethyl or 3-methoxycarbonyl-1-propylamino group, or a 1-piperazinyl group which is substituted in position 4 by a 4-piperidinyl, 1-methyl-4-piperidinyl or 1-acetyl-4-piperidinyl group, their tautomers, their stereoisomers and their salts.

The following particularly valuable compounds may be mentioned as examples:

(1) 4-(5-indolylamino)-6-morpholinopyrimido[5,4-d]pyrimidine,
(2) 4-(5-indolylamino)-6-[trans-(4-hydroxycyclohexyl)amino]pyrimido[5,4-d]pyrimidine,
(3) 4-[(3-chloro-4-fluorophenyl)amino]-6-[4-(morpholinocarbonylmethyl)-1-piperazinyl]pyrimido[5,4-d]pyrimidine,
(4) 4-[(3-chloro-4-fluorophenyl)amino]-6-[(4-morpholinyl)amino]pyrimido[5,4-d]pyrimidine,
(5) 4-[(3-chloro-4-fluorophenyl)amino]-6-(4-picolylamino)pyrimido[5,4-d]pyrimidine,
(6) 4-[(3-chloro-4-fluorophenyl)amino]-6-[1-trifluoroacetyl-4-piperidinylamino]pyrimido[5,4-d]pyrimidine,
(7) 4-[(3-chloro-4-fluorophenyl)amino]-6-(endo-tropinylamino)pyrimido[5,4-d]pyrimidine,
(8) 4-[(3-chloro-4-fluorophenyl)amino]-6-(exo-tropinylamino)pyrimido[5,4-d]pyrimidine and their salts.

The compounds of the general formula I can be prepared, for example, by the following processes:

a) reaction of a compound of the general formula

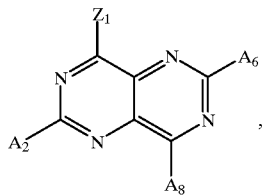

(II)

in which

A_2, A_6 and A_8 are as defined at the outset, and

Z_1 is a leaving group such as a halogen atom, for example a chlorine or bromine atom or a methylsulphonyl or a hydroxyl group, with an amine of the general formula

H-A_4,   (III)

in which

A_4 is as defined at the outset.

The reaction is expediently carried out in a solvent such as isopropanol, butanol, tetrahydrofuran, dioxane, toluene, chlorobenzene, dimethylformamide, dimethyl sulphoxide, ethylene glycol monomethyl ether, ethylene glycol diethyl ether or sulpholane, where appropriate in the presence of an inorganic base, for example sodium carbonate or potassium hydroxide, or of a tertiary organic base, for example triethylamine or pyridine, it also being possible for the latter simultaneously to act as solvent, and where appropriate in the presence of a reaction promoter such as a copper salt, a corresponding amine hydrohalide or alkali metal halide at temperatures between 0 and 200° C., but preferably at temperatures between 60 and 150° C. The reaction can, however, also be carried out without solvent or in an excess of the compound of the general formula III employed.

If Z_1 denotes a hydroxyl group, the reaction is expediently carried out in the presence of hexamethyldisilazane, preferably without other solvents and, where appropriate, in the presence of a reaction promoter such as an organic acid such as, for example, toluenesulphonic acid at temperatures between 0 and 200° C., but preferably at temperatures between 60 and 180° C.

b) To prepare compounds of the general formula I in which A_6 represents one of the radicals mentioned for A_6 at the outset and linked via a nitrogen atom to the pyrimido[5,4-d]pyrimidine:

Reaction of a compound of the general formula

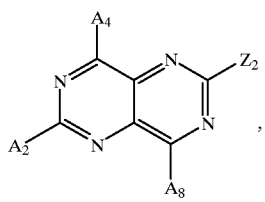

(IV)

in which

A_2, A_4 and A_8 are as defined at the outset, and

Z_2 represents a leaving group such as a halogen atom, a substituted hydroxyl, mercapto, sulphinyl or sulphonyl group such as a chlorine or bromine atom, a methoxy, ethoxy, phenoxy, methylsulphinyl, ethylsulphinyl, methylsulphonyl or ethylsulphonyl group, with a compound of the general formula $$H-A_6, \quad (V)$$

in which

A$_6$ represents the radicals mentioned for A$_6$ at the outset and linked via a nitrogen atom to the pyrimido[5,4-d]pyrimidine.

The reaction is expediently carried out in a solvent such as isopropanol, butanol, tetrahydrofuran, dioxane, toluene, chlorobenzene, dimethylformamide, dimethyl sulphoxide, ethylene glycol monomethyl ether, ethylene glycol diethyl ether or sulpholane, where appropriate in the presence of an inorganic base, for example sodium carbonate or potassium hydroxide, or of a tertiary organic base, for example triethylamine or pyridine, it also being possible for the latter simultaneously to act as solvent, and where appropriate in the presence of a reaction promoter such as a copper salt, an appropriate amine hydrohalide or alkali metal halide at temperatures between 0 and 150° C., but preferably at temperatures between 20 and 120° C. However, the reaction can also be carried out without solvent or in an excess of the compound of the general formula V employed.

If the result according to the invention is a compound of the general formula I containing an amino, alkylamino or imino group, the latter can be converted by acylation or sulphonylation into a corresponding acyl or sulphonyl compound of the general formula I, or a compound of the general formula I containing an amino, alkylamino or imino group, the latter can be converted by alkylation or reductive alkylation into a corresponding alkyl compound of the general formula I, or a compound of the general formula I containing a carboxyl group, the latter can be converted by esterification into a corresponding ester of the general formula I, or a compound of the general formula I containing a carboxyl or ester group, the latter can be converted by amidation into a corresponding amide of the general formula I, or a compound of the general formula I containing a primary or secondary hydroxyl group, the latter can be converted by oxidation into a corresponding carbonyl compound of the general formula I.

Subsequent esterification is carried out where appropriate in a solvent or solvent mixture such as methylene chloride, dimethylformamide, benzene, toluene, chlorobenzene, tetrahydrofuran, benzene/tetrahydrofuran or dioxane or, particularly advantageously, in a corresponding alcohol, where appropriate in the presence of an acid such as hydrochloric acid or in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and, where appropriate, additionally in the presence of 4-dimethylaminopyridine, N,N'-carbonyldiimidazole or triphenylphosphine/tetrachloromethane, expediently at temperatures between 0 and 150° C., preferably at temperatures between 0 and 80° C.

Subsequent acylation or sulphonylation is, where appropriate, carried out in a solvent or solvent mixture such as methylene chloride, dimethylformamide, benzene, toluene, chlorobenzene, tetrahydrofuran, benzene/tetrahydrofuran or dioxane with an appropriate acyl or sulphonyl derivative, where appropriate in the presence of a tertiary organic base or in the presence of an inorganic base or in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and, where appropriate, additionally in the presence of 4-dimethylaminopyridine, N,N'-carbonyldiimidazole or triphenylphosphine/tetrachloromethane, expediently at temperatures between 0 and 150° C., preferably at temperatures between 0 and 80° C.

Subsequent alkylation is carried out, where appropriate, in a solvent or solvent mixture such as methylene chloride, dimethylformamide, benzene, toluene, chlorobenzene, tetrahydrofuran, benzene/tetrahydrofuran or dioxane with an alkylating agent such as an appropriate halide or sulphonic ester, for example with methyl iodide, ethyl bromide, dimethyl sulphate or benzyl chloride, where appropriate in the presence of a tertiary organic base or in the presence of an inorganic base, expediently at temperatures between 0 and 150° C., preferably at temperatures between 0 and 100° C.

Subsequent reductive alkylation is carried out with an appropriate carbonyl compound such as formaldehyde, acetaldehyde, propionaldehyde, acetone or butyraldehyde in the presence of a complex metal hydride such as sodium borohydride, lithium borohydride or sodium cyanoborohydride, expediently at a pH of 6–7 and at room temperature or in the presence of a hydrogenation catalyst, for example with hydrogen in the presence of palladium/carbon, under a pressure of 1 to 5 bar of hydrogen. The methylation is, however, preferably carried out in the presence of formic acid as reducing agent at elevated temperatures, for example at temperatures between 60 and 120° C.

Subsequent amidation is carried out by reacting an appropriate reactive carboxylic acid derivative with an appropriate amine, where appropriate in a solvent or solvent mixture such as methylene chloride, dimethylformamide, benzene, toluene, chlorobenzene, tetrahydrofuran, benzene/tetrahydrofuran or dioxane, it being possible for the amine employed simultaneously to act as solvent, where appropriate in the presence of a tertiary organic base or in the presence of an inorganic base or with an appropriate carboxylic acid in the presence of a dehydrating agent, for example in the presence of isobutyl chloroformate, thionyl chloride, trimethylchlorosilane, sulphuric acid, methanesulphonic acid, p-toluenesulphonic acid, phosphorus trichloride, phosphorus pentoxide, O-(benzotriazol-1-yl)-N,N,N',N'-tetramethyluronium tetrafluoroborate, N,N'-dicyclohexylcarbodiimide, N,N'-dicyclohexylcarbodiimide/N-hydroxysuccinimide or 1-hydroxybenzotriazole and, where appropriate, additionally in the presence of 4-dimethylaminopyridine, N,N'-carbonyldiimidazole or triphenylphosphine/tetrachloromethane, expediently at temperatures between 0 and 150° C., preferably at temperatures between 0 and 80° C.

Subsequent oxidation is carried out, where appropriate, in a solvent such as methylene chloride, water, dimethylformamide, benzene, chlorobenzene, tetrahydrofuran or dioxane with an oxidizing agent such as chromic acid, chromium trioxide and pyridine, pyridinium dichromate, pyridinium chlorochromate, oxalyl chloride/dimethyl sulphoxide/triethylamine, tetra-n-propyl perruthenate/N-methylmorpholine N-oxide, ruthenium trichloride/sodium metaperiodate or Dess-Martin reagent, expediently at temperatures between −80 and 100° C., preferably at temperatures between −80° C. and room temperature.

During the reactions described above, reactive groups which are present where appropriate, such as hydroxyl, carboxyl, amino, alkylamino or imino groups, can be protected during the reaction by conventional protective groups which are eliminated again after the reaction.

For example, a suitable protective radical for a hydroxyl group is the trimethylsilyl, acetyl, benzoyl, methyl, ethyl, tert-butyl, trityl, benzyl or tetrahydropyranyl group, suitable protective radicals for a carboxyl group are the trimethylsilyl, methyl, ethyl, tert-butyl, benzyl or tetrahydropyranyl group, suitable protective radicals for a phosphono group are an alkyl group such as the methyl, ethyl, isopropyl or n-butyl group, the phenyl or benzyl group, suitable protective radicals for an amino, alkylamino or imino group are the formyl, acetyl, trifluoroacetyl, ethoxycarbonyl, tert-butoxycarbonyl, benzyloxycarbonyl, benzyl, methoxybenzyl or 2,4-dimethoxybenzyl group and for the amino group in addition the phthalyl group and suitable protective radicals for the nitrogen atom in a 1-azabicycloalkyl group such as the quinuclidinyl group are the benzyl group or borane.

The subsequent elimination, where appropriate, of a protective radical which has been used takes place, for example, by hydrolysis in an aqueous solvent, for example in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, for example in the presence of iodotrimethylsilane, at temperatures between 0 and 120° C., preferably at temperatures between 10 and 100° C.

However, a benzyl, methoxybenzyl or benzyloxycarbonyl radical is eliminated, for example, by hydrogenolysis, for example with hydrogen in the presence of a catalyst such as palladium/carbon in a suitable solvent such as methanol, ethanol, ethyl acetate or glacial acetic acid, where appropriate with the addition of an acid such as hydrochloric acid at temperatures between 0 and 100° C., but preferably at temperatures between 20 and 60° C., and under a pressure of 1 to 7 bar, but preferably of 3 to 5 bar, of hydrogen. However, a 2,4-dimethoxybenzyl radical is preferably eliminated in trifluoroacetic acid in the presence of anisole.

A tert-butyl or tert-butyloxycarbonyl radical is preferably eliminated by treatment with an acid such as trifluoroacetic acid or hydrochloric acid or by treatment with iodotrimethylsilane, where appropriate using a solvent such as methylene chloride, dioxane, methanol or diethyl ether.

A trifluoroacetyl radical is preferably eliminated by treatment with an acid such as hydrochloric acid, where appropriate in the presence of a solvent such as acetic acid, at temperatures between 50 and 120° C. or by treatment with sodium hydroxide solution, where appropriate in the presence of a solvent such as tetrahydrofuran at temperatures between 0 and 50° C.

A phthalyl radical is preferably eliminated in the presence of hydrazine or of a primary amine such as methylamine, ethylamine or n-butylamine in a solvent such as methanol, ethanol, isopropanol, toluene/water or dioxane at temperatures between 20 and 50° C.

Cleavage of the complex of a 1-azabicycloalkyl group such as the quinuclidinyl group with borane preferably takes place by treatment with an acid such as hydrochloric acid and, where appropriate, in the presence of a solvent such as methanol, ethanol, acetic acid or dioxane at temperatures between 0° C. and the boiling point of the reaction mixture. It is possible in this reaction for an ester group which is present where appropriate simultaneously to be converted into the corresponding carboxyl group.

It is furthermore possible for the resulting compounds of the general formula I to be, as has already been mentioned at the outset, fractionated into their enantiomers and/or diastereomers. Thus, for example, cis/trans mixtures can be fractionated into their cis and trans isomers, and compounds with at least one optically active carbon atom can be fractionated into their enantiomers.

Thus, for example, the resulting cis/trans mixtures can be fractionated by chromatography into their cis and trans isomers, the resulting compounds of the general formula I which occur in racemates can be fractionated by methods known per se (see Allinger N. L. and Eliel E. L. in "Topics in Stereochemistry", Vol. 6, Wiley Interscience, 1971) into their optical antipodes and compounds of the general formula I with at least 2 asymmetric carbon atoms can be fractionated on the basis of their physicochemical differences by methods known per se, for example by chromatography and/or fractional crystallization, into their diastereomers which, if they result in racemic form, can subsequently be separated into the enantiomers as mentioned above.

Enantiomers are preferably separated by column separation on chiral phases or by recrystallization from an optically active solvent or by reaction with an optically active substance which forms salts or derivatives such as, for example, esters or amides with the racemic compound, in particular acids and their activated derivatives or alcohols, and separation of the diastereomeric salt mixture or derivative obtained in this way, for example on the basis of different solubilities, it being possible to liberate the free antipodes from the pure diastereomeric salts or derivatives by the action of suitable agents. Examples of particularly useful optically active acids are the D and L forms of tartaric acid or dibenzoyltartaric acid, di-o-tolyltartaric acid, malic acid, mandelic acid, camphorsulphonic acid, glutamic acid, aspartic acid or quinic acid. An example of a suitable optically active alcohol is or (−)-menthol and of an optically active acyl radical in amides is (+)- or (−)-menthyloxycarbonyl.

It is furthermore possible for the resulting compounds of the formula I to be converted into their salts, in particular for pharmaceutical use into their physiologically tolerated salts with inorganic or organic acids. Examples of acids suitable for this purpose are hydrochloric acid, hydrobromic acid, sulphuric acid, phosphoric acid, fumaric acid, succinic acid, lactic acid, citric acid, tartaric acid or maleic acid.

In addition, the novel compounds of the formula I obtained in this way can, if they contain a carboxyl, phosphono, o-alkylphosphono, sulpho or 5-tetrazolyl group, subsequently be converted if required into their salts with inorganic or organic bases, in particular for pharmaceutical use into their physiologically tolerated salts. Examples of bases suitable in this connection are sodium hydroxide, potassium hydroxide, arginine, cyclohexylamine, ethanolamine, diethanolamine and triethanolamine.

Some of the compounds of the general formulae II to V used as starting materials are known from the literature, or they are obtained by processes known per se from the literature (see Examples I to XVIII).

As already mentioned at the outset, the compounds of the general formula I according to the invention, and their physiologically tolerated salts, have valuable pharmacological properties, in particular a specific inhibitory effect on signal transduction mediated by epidermal growth factor receptor (EGF-R), this possibly being brought about, for example, by inhibition of ligand binding, of receptor dimerization or of tyrosine kinase itself. It is additionally possible that the signal transmission is blocked at components located further downstream.

The biological properties of the novel compounds were tested as follows:

The inhibition of signal transmission mediated by EGF-R can be demonstrated, for example, using cells which express human EGF-R and whose survival and proliferation depends on stimulation by EGF or TGF-alpha. In this case, an interleukin-3 (IL-3)-dependent cell line of murine origin was used and was genetically modified in such a way that it expresses functional human EGF-R. Proliferation of these cells, which are called F/L-HERc, can therefore be stimulated either by murine IL-3 or by EGF (see von Rüden, T. et al. in EMBO J. 7, 2749–2756 (1988) and Pierce, J. H. et al. in Science 239, 628–631 (1988)).

The starting material for the F/L-HERc cells was the cell line FDC-$P_1$, whose preparation has been described by Dexter, T. M. et al. in J. Exp. Med. 152, 1036–1047 (1980). However, it is also possible as an alternative to use other growth factor-dependent cells (see, for example, Pierce, J. H. et al. in Science 239, 628–631 (1988), Shibuya, H. et al. in Cell 70, 57–67 (1992) and Alexander, W. S. et al. in EMBO J. 10, 3683–3691 (1991)). Recombinant retroviruses as described in von Rüden, T. et al., EMBO J. 7, 2749–2756 (1988) were used for expression of the human EGF-R cDNA (see Ullrich, A. et al. in Nature 309, 418–425 (1984)) with the difference that the retroviral vector LXSN (see Miller, A. D. et al. in BioTechniques 7, 980–990 (1989)) was employed for expression of the EGF-R cDNA, and the line GP+E86 (see Markowitz, D. et al. in J. Virol. 62, 1120–1124 (1988)) was used as packaging cell.

The test was carried out as follows:

F/L-HERc cells were cultivated in RPMI/1640 medium (BioWhittaker), supplemented with 10% fetal calf serum (FCS, Boehringer Mannheim), 2 mM glutamine (BioWhittaker), standard antibiotics and 20 ng/ml human EGF (Promega), at 37° C. and 5% $CO_2$. To investigate the inhibitory activity of the compounds according to the invention, $1.5 \times 10^4$ cells were cultivated in the above medium (200 µl) per well in triplicates in 96-well plates, stimulating proliferation of the cells either with EGF (20 ng/ml) or with murine IL-3. The source used for IL-3 was culture supernatants from the cell line X63/0 mIL-3 (see Karasuyama, H. et al. in Eur. J. Immunol. 18, 97–104 (1988)). The compounds according to the invention were dissolved in 100% dimethyl sulphoxide (DMSO) and added in various dilutions to the cultures, with the maximum DMSO concentration being 1%. The cultures were incubated at 37° C. for 48 hours.

To determine the inhibitory activity of the compounds according to the invention, the relative cell count was measured in O.D. units using the Cell Titre 96™ AQueous Non-Radioactive Cell Proliferation Assay (Promega). The relative cell count was calculated as a per cent of the control (F/L-HERc cells without inhibitor), and the concentration of active substance which inhibits the proliferation of the cells by 50% ($IC_{50}$) was inferred. The following results were obtained in this:

| Compound (Example No.) | Inhibition of EGF-dependent proliferation $IC_{50}$ [nM] | Inhibition of IL-3-dependent proliferation $IC_{50}$ [µM] |
|---|---|---|
| 1 | 21 | 10 |
| 1(1) | 2000 | 10 |
| 1(2) | 1000 | not tested |
| 1(3) | 800 | not tested |
| 1(4) | 125 | not tested |
| 1(5) | 1000 | not tested |
| 1(9) | 6000 | not tested |
| 1(13) | 10000 | 9 |
| 1(14) | 2300 | 2.2 |
| 1(15) | 1 | >10 |
| 1(16) | 200 | not tested |
| 2 | 50 | >1 |
| 2(1) | 1 | >10 |
| 2(2) | 400 | not tested |
| 2(3) | 138 | >10 |
| 2(4) | 200 | >10 |
| 2(5) | 40 | >10 |
| 2(6) | 3 | >10 |
| 2(7) | 175 | >1 |
| 2(8) | 15 | >20 |
| 2(9) | 225 | >20 |
| 2(10) | 275 | >20 |
| 2(11) | 190 | not tested |
| 2(12) | 98 | not tested |
| 2(15) | >10000 | not tested |
| 2(18) | 138 | >10 |
| 2(19) | 28 | >10 |

The compounds according to the invention also inhibit EGF-stimulated proliferation of the human tumour cell line KB which originates from an oral epidermoid carcinoma and overexpresses the EGF receptor (for example Aboud-Pirak, E. et al, J. Natl. Cancer. Inst. 80, 1605–11 (1988). KB cells (purchased from ATCC) were passaged in DMEM (BioWhittaker) in the presence of 10% FCS (Boehringer Mannheim), 50 µM beta-mercaptoethanol and standard antibiotics. The EGF-induced DNA synthesis was determined by measuring the incorporation of radioactively labelled thymidine as indicator of EGF/TGF-alpha-stimulated cell proliferation. To do this, the cells were washed twice and 1500 cells per well were plated out in a 96-well plate in 200 µl of IMDM (BioWhittaker) without serum in the presence of 50 µM mercaptoethanol, standard antibiotics, TGF-alpha [10 ng/ml] or EGF [20 ng/ml] and of various concentrations of the substances according to the invention (triplicates, maximum DMSO concentration 1%, see proliferation test with F/L-HERc cells). After 60 hours, [$^3$H]-thymidine (0.1 µCi in 10 µl) was added for about 16–18 h. Subsequent measurement of thymidine incorporation revealed an $IC_{50}$ of 400 nM for the compound of Example 2, and one of 100 nM for the compound of Example 2(6) for the inhibition of EGF/TGF-alpha-stimulated KB cell proliferation.

The compounds of the general formula I according to the invention thus inhibit signal transduction by tyrosine kinases, as has been shown by the example of the human EGF receptor, and can therefore be used to treat pathophysiological processes caused by hyperactivity of tyrosine kinases. Examples of these are benign or malignant tumours, in particular tumours of epithelial and neuroepithelial origin, metastasis and abnormal proliferation of vascular endothelial cells (neoangiogenesis).

In addition, the compounds of the general formula I and their physiologically tolerated salts can be used to treat other disorders caused by aberrant activity of tyrosine kinases, such as, for example, epidermal hyperproliferation (psoriasis), inflammatory processes, disorders of the immune system, hyperproliferation of haemopoietic cells etc.

Because of their biological properties, the compounds according to the invention can be used alone or in combination with other pharmacologically active compounds, for example in tumour therapy as monotherapy or in combination with other antitumour therapeutics, for example in combination with topoisomerase inhibitors (for example etoposides), mitosis inhibitors (for example vinblastine), compounds which interact with nucleic acids (for example cis-platin, cyclophosphamide, adriamycin), hormone antagonists (for example tamoxifen), inhibitors of metabolic processes (for example 5-FU etc.), cytokines (for example interferons), antibodies etc. These combinations can be administered either simultaneously or sequentially.

For pharmaceutical use, the compounds according to the invention are, as a rule, used in dosages of 0.01–100 mg/kg of body weight, preferably 0.1–15 mg/kg, for warm-blooded vertebrates, in particular humans. For administration, they are incorporated with one or more conventional inert excipients and/or diluents, for example with maize starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances such as hard fat or suitable mixtures thereof in conventional pharmaceutical preparations such as tablets, coated tablets, capsules, powders, suspensions, solutions, sprays or suppositories.

The following examples are intended to illustrate the present invention in detail without restricting it:

EXAMPLE I

4-Hydroxy-6-methylsulphinylpyrimido[5,4-d]pyrimidine and 4-hydroxy-6-methylsulphonylpyrimido[5,4-d]pyrimidine 2.0 g of 4-hydroxy-6-methylthiopyrimido[5,4-d]pyrimidine and 8 g of 3-chloroperoxybenzoic acid (content: 50%) are stirred vigorously in 50 ml of methylene chloride for 3 hours. The precipitate is filtered off with suction, washed with ethyl acetate and dried.

Yield: 2.2 g, $R_f$: 0.27 and 0.50 (silica gel; methylene chloride/ethyl acetate/methanol=10:4:3).

EXAMPLE II

4-Hydroxy-6-(morpholino)pyrimido[5,4-d]pyrimidine 16 g of a mixture of 4-hydroxy-6-methylsulphinylpyrimido-[5,4-d]pyrimidine and 4-hydroxy-6-methylsulphonylpyrimido-[5,4-d]pyrimidine in 25 ml of morpholine are heated at 135° C (bath temperature) for 4 hours. After cooling and concentration, the residue is triturated with water, and the solid is filtered off with suction, washed with water and dried.

Yield: 7.8 g, Melting point: >240° C., $R_f$: 0.60 (silica gel; methylene chloride/ethyl acetate/methanol=10:4:3).

The following compound is obtained in analogy to Example II:

(1) 4-hydroxy-6-(cyclopropylamino)pyrimido[5,4-d]pyrimidine

Melting point: >240° C., $R_f$: 0.45 (silica gel; methylene chloride/ethyl acetate/methanol=10:4:3).

EXAMPLE III

4-Chloro-6-(morpholino)pyrimido[5,4-d]pyrimidine 7.8 g of 4-hydroxy-6-(morpholino)pyrimido[5,4-d]pyrimidine are heated under reflux with 100 ml of thionyl chloride with the addition of 4 drops of dimethylformamide for 1.5 hours. The reaction mixture is concentrated and, after addition of methylene chloride, concentrated once again. The residue is then partitioned between methylene chloride and an aqueous potassium carbonate solution. The aqueous phase is extracted twice more with methylene chloride, and the combined organic phases are dried over magnesium sulphate and concentrated. The residue is triturated with diethyl ether and filtered off with suction.

Yield: 8.0 g (90% of theory), Melting point: 238–240° C. (decomposition), $R_f$: 0.60 (silica gel; petroleum ether/ethyl acetate=2:1).

| Calculated: | C 63.49 | H 4.76 | N 27.28 |
|---|---|---|---|
| Found: | 63.39 | 4.80 | 27.00 |

The following compounds are obtained in analogy to Example III:

(1) 4-chloro-6-methylthiopyrimido[5,4-d]pyrimidine

Melting point: 90–92° C., $R_f$: 0.63 (silica gel; petroleum ether/ethyl acetate=7:3).

(2) 4-chloro-6-(cyclopropylamino)pyrimido[5,4-d]pyrimidine

Melting point: 135° C. (decomposition), $R_f$: 0.53 (silica gel; petroleum ether/ethyl acetate=2:1).

EXAMPLE IV

5-Amino-2-methylthiopyrimidine-4-carboxylic Acid 131.4 g of 5-bromo-2-methylthiopyrimidine-4-carboxylic acid, 860 ml of concentrated aqueous ammonia and 2.42 g of copper(II) sulphate dissolved in 34 ml of water are shaken in a pressure vessel at 95° C. for 4 hours. After cooling, the precipitate is filtered off with suction. The precipitate is dissolved in 600 ml of hot water, and the solution is filtered through active carbon. The filtrate is cooled in an icebath and adjusted to pH 3 with concentrated hydrochloric acid. The precipitate is filtered off with suction and purified by dissolving in dilute sodium hydroxide solution and precipitating with hydrochloric acid.

Yield: 54.6 g (56% of theory), Melting point: 187° C., $R_f$: 0.35 (silica gel; ethyl acetate/methanol=2:1).

EXAMPLE V

4-Hydroxy-6-methylthiopyrimido[5,4-d]pyrimidine 25 g of 5 amino-2-methylthiopyrimidine-4-carboxylic acid and 150 ml of formamide are stirred in an oil bath, with the temperature of the oil bath being increased to 180° C. over the course of half an hour. Stirring is continued at this temperature for 1.5 hours. The reaction mixture is then added hot to 750 ml of an ice/water mixture. After 2 hours, the product is filtered off with suction, washed with water and dried.

Melting point: >240° C., $R_f$: 0.63 (silica gel; methylene chloride/ethyl acetate/methanol=10:4:3).

EXAMPLE VI

4-Hydroxy-6-methylthiopyrimido[5,4-d]pyrimidine

A mixture of 69 g of 5-amino-2-methylthiopyrimidine-4-carboxylic acid, 155 g of formamidine acetate and 300 ml of ethoxyethanol is heated to boiling for 2 hours. The reaction mixture is then cooled to 10° C., 250 ml of water are added, and the mixture is left to stand at 10° C. for one hour. It is then filtered with suction, washed with water and dried.

Yield: 59 g (82% of theory), Melting point: >240° C., $R_f$: 0.63 (silica gel; methylene chloride/ethyl acetate/methanol=10:4:3).

The following compound is obtained in analogy to Example VI:

(1) 2-methyl-4-hydroxy-6-methylthio-pyrimido[5,4-d]pyrimidine Prepared using acetamidine hydrochloride and sodium acetate.

Melting point: >250° C., $R_f$: 0.24 (silica gel; methylene chloride/methanol=95:5).

EXAMPLE VII

4-[(3-Chloro-4-fluorophenyl)amino]-6-methylthiopyrimido-[5,4-d]pyrimidine 3.0 g of 4-chloro-6-methylthiopyrimido[5,4-d]pyrimidine, 3.8 g of 3-chloro-4-fluoroaniline and 10 ml of dioxane are heated at 80° C. for 2 hours. After cooling, the reaction mixture is concentrated and triturated first with water and then with diethyl ether, filtered off with suction and dried.

Yield: 4.0 g (91% of theory), Melting point: 144–148° C., $R_f$: 0.50 (silica gel; petroleum ether/ethyl acetate=1:1).

EXAMPLE VIII

4-[(3-Chloro-4-fluorophenyl)amino]-6-methylthiopyrimido-[5,4-d]pyrimidine 148 g of 4-hydroxy-6-methylthiopyrimido[5,4-d]pyrimidine, 286 ml of hexamethyldisilazane, 333 g of 3-chloro-4-fluoroaniline and 15 g of p-toluenesulphonic acid are heated at 140° C. for 23 hours. The reaction mixture is cooled and, after addition of 4 l of methanol, heated at 100° C. for one hour. The methanol is distilled off and the residue is triturated three times with diethyl ether and filtered off with suction.

Yield: 202 g (82% of theory), Melting point: 144–148° C., $R_f$: 0.50 (silica gel; petroleum ether/ethyl acetate=1:1).

The following compounds are obtained in analogy to Example VIII:

(1) 4-[(3-methylphenyl)amino]-6-methylthiopyrimido[5,4-d]-pyrimidine

Melting point: 118–120° C., $R_f$: 0.55 (silica gel; petroleum ether/ethyl acetate=2:1).

(2) 4-[2-fluorenylamino]-6-methylthiopyrimido[5,4-d]pyrimidine

Melting point: 212–214° C., $R_f$: 0.48 (silica gel; petroleum ether/ethyl acetate=2:1).

(3) 4-[(3-chloro-4-fluorophenyl)amino]-2-methyl-6-methylthiopyrimido[5,4-d]pyrimidine Melting point: 70–75° C., $R_f$: 0.33 (silica gel; methylene chloride/methanol=95:5).

(4) 4-(5-indolylamino)-6-methylthiopyrimido[5,4-d]pyrimidine

Melting point: 162–164° C., $R_f$: 0.40 (silica gel; petroleum ether/ethyl acetate=1:1).

(5) 4-[(4-amino-3,5-dibromophenyl)amino]-6-methylthiopyrimido-[5,4-d]pyrimidine

Prepared from the compound of Example XVIII.

Melting point: 245–247° C.

(6) 4-[4-phenoxyphenylamino]-6-methylthiopyrimido[5,4-d]-pyrimidine

Melting point: 191–192° C., $R_f$: 0.50 (silica gel; petroleum ether/ethyl acetate=10:5).

EXAMPLE IX

4-[(3-Chloro-4-fluorophenyl)amino]-6-methylsulphinylpyrimido-[5,4-d]pyrimidine and 4-[(3-chloro-4-fluorophenyl)amino]-6-methylsulphonylpyrimido[5,4-d]pyrimidine 4.0 g of 4-[(3-chloro-4-fluorophenyl)amino]-6-methylthiopyrimido[5,4-d]pyrimidine are dissolved in 100 ml of methylene chloride and 5 ml of methanol and, at room temperature, 8.0 g of 3-chloroperoxybenzoic acid (50% pure) are added in portions. After 2 hours, the mixture is washed twice with sodium bicarbonate solution, dried over magnesium sulphate and concentrated. The title compounds are obtained as a 1:1 mixture and employed further without further separation.

Yield: 4.2 g, Melting point of the mixture: 170° C. (decomposition), $R_f$ values: 0.10 and 0.28 (silica gel; petroleum ether/ethyl acetate=1:1).

EXAMPLE X

4-[(3-Chloro-4-fluorophenyl)amino]-6-methylsulphinylpyrimido-[5,4-d]pyrimidine and 4-[(3-chloro-4-fluorophenyl)amino]-6-methylsulphonylpyrimido[5,4-d]pyrimidine 39.2 g of 4-[(3-chloro-4-fluorophenyl)amino]-6-methylthiopyrimido[5,4-d]pyrimidine are dissolved in 350 ml of glacial acetic acid and, at room temperature, 37 g of sodium perborate are added in portions over the course of 4 hours. After 24 hours, the mixture is poured into 1 l of water, and the precipitate is filtered off with suction and washed twice with water, once with sodium bicarbonate solution and twice again with water and dried. The product is a 10:1 mixture of sulphoxide and sulphonyl compounds and is employed further without further purification.

Yield: 38 g, $R_f$: 0.10 and 0.28 (silica gel; petroleum ether/ethyl acetate=1:1), Melting point of the mixture: 140–145° C. (decomposition).

The following compounds are obtained in analogy to Examples IX and X:

(1) 4-[(3-methylphenyl)amino]-6-methylsulphinylpyrimido-[5,4-d]pyrimidine and 4-[(3-methylphenyl)amino]-6-methylsulphonylpyrimido[5,4-d]pyrimidine $R_f$: 0.38 and 0.54 (silica gel; petroleum ether/ethyl acetate/methanol=10:10:1).

(2) 4-[2-fluorenylamino]-6-methylsulphinylpyrimido[5,4-d]-pyrimidine and 4-[2-fluorenylamino]-6-methylsulphonylpyrimido[5,4-d]pyrimidine $R_f$: 0.50 (silica gel; petroleum ether/ethyl acetate/methanol=10:10:2).

(3) 4-[(3-chloro-4-fluorophenyl)amino]-2-methyl-6-methylsulphinylpyrimido[5,4-d]pyrimidine and 4-[(3-chloro-4-fluorophenyl)amino]-2-methyl-6-methylsulphonylpyrimido-[5,4-d]pyrimidine Melting point: 148° C., $R_f$: 0.41 and 0.48 (silica gel; methylene chloride/methanol=95:5).

(4) 4-(5-indolylamino)-6-methylsulphinylpyrimido[5,4-d]-pyrimidine and 4-(5-indolylamino)-6-methylsulphonylpyrimido-[5,4-d]pyrimidine $R_f$ values: 0.35 and 0.45 (silica gel; petroleum ether/ethyl acetate/methanol=10:10:3).

(5) 4-[(4-amino-3,5-dibromophenyl)amino]-6-methylsulphonylpyrimido[5,4-d]pyrimidine $R_f$: 0.53 (silica gel; petroleum ether/ethyl acetate/methanol=10:10:2).

(6) 4-[4-phenoxyphenylamino]-6-methylsulphinylpyrimido[5,4-d]-pyrimidine and 4-[4-phenoxyphenylamino]-6-methylsulphonylpyrimido[5,4-d]pyrimidine $R_f$: 0.28 and 0.41 (silica gel; petroleum ether/ethyl acetate/methanol=10:10:1).

EXAMPLE XI

4-Amino-1-tert-butyloxycarbonylpiperidine 22 g of di-tert-butyl dicarbonate and 14 ml of triethylamine are added to 10 g of 4-aminopiperidine in 120 ml of a dioxane/water (1:1) mixture at 0° C., and the mixture is stirred at room temperature for 12 hours. The dioxane is then distilled off in a rotary evaporator, and the aqueous phase is extracted six times with ethyl acetate. The combined organic phases are dried over magnesium sulphate, and the solvent is distilled off in a rotary evaporator. The residue slowly crystallizes.

Yield: 16 g (80% of theory), Melting point: 47–52° C., $R_f$: 0.69 (alumina; methylene chloride/methanol=9:1).

EXAMPLE XII trans-4-tert-Butyloxycarbonylaminomethylcyclohexanecarboxylic Acid 4.6 g of trans-4-aminomethylcyclohexanecarboxylic acid are dissolved in 65 ml of 1 N sodium hydroxide solution, and 6.6 g of di-tert-butyl dicarbonate in 50 ml of tetrahydrofuran are added. After 12 hours, the mixture is extracted six times with ethyl acetate. The combined organic phases are washed successively with a 2 N citric acid solution and saturated sodium chloride solution and dried over magnesium sulphate, and the solvent is distilled off in a rotary evaporator. The residue is dried under 0.1 torr.

Yield: 6.5 g (87% of theory), Melting point: 137–140° C.

EXAMPLE XIII trans-4-(tert-Butyloxycarbonylaminomethyl)benzyloxycarbonylaminocyclohexane 5.5 g of trans-4-tert-butyloxycarbonylaminomethylcyclohexanecarboxylic acid are dissolved in 250 ml of dioxane and, after addition of 6.5 ml of triethylamine and 5.6 ml of diphenylphosphoryl azide, heated at 130° C. for 1.5 hours. Then 8.7 ml of benzyl alcohol are added and the mixture is heated to boiling for a further 48 hours. After cooling, the dioxane is distilled off in a rotary evaporator, the residue is taken up in ethyl acetate and, after washing with saturated sodium chloride solution and drying over magnesium sulphate, the solvent is distilled off in a rotary evaporator. The residue is triturated with petroleum ether/ether (5:1), filtered off with suction and dried.

Yield: 6.6 g (86% of theory), Melting point: 117–122° C.

EXAMPLE XIV trans-4-Amino(tert-butyloxycarbonylaminomethyl)cyclohexane 1.4 g of trans-4-(tert-butyloxycarbonylaminomethyl)benzyloxycarbonylaminocyclohexane are dissolved in 30 ml of methanol and, after addition of 0.3 g of palladium/active carbon catalyst, hydrogenated under a pressure of 50 psi of hydrogen at room temperature for one hour. After filtration, the solvent is distilled off in a rotary evaporator. The residue is employed without further purification.

Yield: 1.02 g (100% of theory) of a colourless wax, $R_f$: 0.28 (alumina; methylene chloride/methanol 10:1).

EXAMPLE XV

2-Chloro-8-(3-chloro-4-fluorophenylamino)-4-methylpyrimido-[5,4-d]pyrimidine

A solution of 2.74 g of zinc bromide in 20 ml of tetrahydrofuran was added dropwise to a solution of 4.1 ml of 3 M methylmagnesium bromide in tetrahydrofuran at −78° C. This mixture was stirred at −78° C. for one hour and then added dropwise over the course of 20 minutes to a solution of 2.4 g of 2,4,8-trichloropyrimido[5,4-d]pyrimidine in 0.71 g of tetrakis(triphenylphosphine)palladium in 20 ml of tetrahydrofuran at −40° C. After one hour at −40° C., the mixture was allowed to reach room temperature and was then stirred for 12 hours. Then 100 ml of water were cautiously added, the mixture was extracted three times with 100 ml of ethyl acetate each time, the combined organic phases were dried over magnesium sulphate, and the solvent was distilled off in a rotary evaporator. The residue (dark viscous oil) was taken up without further purification in 20 ml of dioxane, 1.45 g of 3-chloro-4-fluoroaniline and 1.7 ml of N-ethyldiisopropylamine were added and this mixture was heated at 70° C. for four hours. The solvent was then distilled off in a rotary evaporator, and the residue was triturated with ether and filtered off with suction. The residue was triturated with water and again filtered off with suction, and the remaining residue was taken up in methylene chloride and filtered. The filtrate was evaporated and the residue (about 2 g of dark oil) was purified by column chromatography on silica gel with a petroleum ether/ethyl acetate mixture (4:1).

Yield: 194 mg (6% of theory),

Melting point: 172–174° C., $R_f$: 0.50 (silica gel; petroleum ether/ethyl acetate=4:1).

EXAMPLE VI

4-Tetrahydropyranone Oxime 5.0 g of 4-tetrahydropyranone are added dropwise to a stirred mixture of 5.2 g of hydroxylamine hydrochloride and 4.8 g of sodium acetate in 50 ml of water at 60° C. After a further hour at 60° C., the solution is allowed to cool and is extracted three times with 50 ml of ether each time. The combined organic phases are then dried over sodium sulphate, the solvent is distilled off in a rotary evaporator, and the residue is employed without further purification in the next reaction.

Yield: 4.2 g (74% of theory), Melting point: 50–52° C., $R_f$: 0.30 (silica gel; petroleum ether/ethyl acetate=1:1).

EXAMPLE XVII

4-Aminotetrahydropyran 4.2 g of 4-tetrahydropyranone oxime are dissolved in 100 ml of ethanol and, after addition of 0.5 g of palladium on carbon (10%), hydrogenated under a pressure of 5 bar of hydrogen in a Parr apparatus at 90° C. for 2.5 hours. After cooling, the solvent is distilled off in a rotary evaporator, and the residue is used further without further purification.

Yield: 0.7 g (19% of theory) of a colourless oil, $R_f$: 0.45 (silica gel; methylene chloride/ethyl acetate/methanol=10:4:2).

EXAMPLE XVIII 1,4-Diamino-2,6-dibromobenzene 3.0 g of 2,6-dibromo-4-nitroaniline are dissolved in 150 ml of ethanol, 150 ml of ethyl acetate and 30 ml of dimethylformamide and, after addition of 0.5 g of platinum on carbon (5%), hydrogenated under a pressure of 1.5 bar of hydrogen in a Parr apparatus at room temperature for 1 hour. Cooling is followed by filtration, the solvent is distilled off in a rotary evaporator, and the residue is purified by column chromatography.

Yield: 14 g of a colourless oil, $R_f$: 0.47 (silica gel; petroleum ether/ethyl acetate 2:1).

EXAMPLE 1

4-(5-Indolylamino)-6-morpholinopyrimido[5,4-d]pyrimidine

A mixture of 0.4 g of 4-chloro-6-morpholinopyrimido[5,4-d]-pyrimidine, 0.4 g of 5-aminoindole and 10 ml of n-butanol is heated at 120° C. for 1.5 hours. The solvent is distilled off in a rotary evaporator, and the residue is mixed with water, stirred and filtered. The residue is then mixed with ether, stirred and again filtered off.

Yield: 0.43 g (77% of theory), Melting point: 253–255° C., $R_f$: 0.31 (silica gel; petroleum ether/ethyl acetate=1:2).

| Calculated: | C 62.23 | H 4.93 | N 28.06 |
|---|---|---|---|
| Found: | 61.85 | 5.16 | 27.79 |

The following compounds can be obtained in analogy to Example 1:

(1) 4-(5-quinolylamino)-6-morpholinopyrimido[5,4-d]pyrimidine

Melting point: 185–187° C., $R_f$: 0.35 (alumina; petroleum ether/ethyl acetate=1:2).

| Calculated: | C 63.49 | H 4.76 | N 27.28 |
|---|---|---|---|
| Found: | 63.39 | 4.93 | 26.56 |

(2) 4-(6-quinolylamino)-6-morpholinopyrimido[5,4-d]pyrimidine

Melting point: 238–240° C., $R_f$: 0.20 (silica gel; petroleum ether/ethyl acetate/methanol=10:20:1).

| Calculated: | C 63.49 | H 4.76 | N 27.28 |
|---|---|---|---|
| Found: | 63.39 | 4.80 | 27.00 |

(3) 4-(8-quinolylamino)-6-morpholinopyrimido[5,4-d]pyrimidine

Melting point: 250–252° C., $R_f$: 0.25 (silica gel; petroleum ether/ethyl acetate=1:2).

| Calculated: | C 63.49 | H 4.76 | N 27.28 |
|---|---|---|---|
| Found: | 62.39 | 4.80 | 26.80 |

(4) 4-(5-indazolylamino)-6-morpholinopyrimido[5,4-d]pyrimidine

Melting point: 280–283° C., $R_f$: 0.33 (silica gel; petroleum ether/ethyl acetate/methanol=10:10:1).

(5) 4-[4-(2,1,3-benzothiadiazolyl)amino]-6-morpholinopyrimido[5,4-d]pyrimidine

Melting point: 255–257° C., $R_f$: 0.45 (silica gel; petroleum ether/ethyl acetate=1:2).

| Calculated: | C 52.44 | H 3.85 | N 30.58 |
|---|---|---|---|
| Found: | 52.32 | 4.03 | 30.25 |

(6) 4-(6-indazolylamino)-6-morpholinopyrimido[5,4-d]pyrimidine

Melting point: 279–281° C., $R_f$: 0.30 (silica gel; petroleum ether/ethyl acetate/methanol=10:10:1).

| Calculated: | C 58.61 | H 4.62 | N 32.16 |
|---|---|---|---|
| Found: | 58.15 | 4.83 | 31.88 |

(7) 4-(2-thiazolylamino)-6-morpholinopyrimido[5,4-d]pyrimidine

Melting point: 208–210° C., $R_f$: 0.45 (silica gel; petroleum ether/ethyl acetate=1:2).

| Calculated: | C 49.51 | H 4.15 | N 31.09 |
|---|---|---|---|
| Found: | 49.89 | 4.32 | 31.11 |

(8) 4-(2-methyl-5-benzothiazolylamino)-6-morpholinopyrimido-[5,4-d]pyrimidine

Melting point: 208–210° C., $R_f$: 0.31 (silica gel; petroleum ether/ethyl acetate=1:2).

| Calculated: | C 56.97 | H 4.51 | N 25.83 |
|---|---|---|---|
| Found: | 56.86 | 4.61 | 25.73 |

(9) 4-(3-pyridylamino)-6-morpholinopyrimido[5,4-d]pyrimidine

Melting point: 220–222° C., $R_f$: 0.20 (silica gel; petroleum ether/ethyl acetate=1:2).

(10) 4-(2-benzothiazolylamino)-6-morpholinopyrimido[5,4-d]-pyrimidine

Melting point: 221–223° C., $R_f$: 0.20 (silica gel; petroleum ether/ethyl acetate=1:2).

| Calculated: | C 55.87 | H 4.13 | N 26.83 |
|---|---|---|---|
| Found: | 55.78 | 4.25 | 26.98 |

(11) 4-(2-pyridylamino)-6-morpholinopyrimido[5,4-d]pyrimidine

Melting point: 192–194° C., $R_f$: 0.33 (alumina; petroleum ether/ethyl acetate=1:2).

(12) 4-(5-isoquinolylamino)-6-morpholinopyrimido[5,4-d]-pyrimidine

Melting point: 203–205° C., $R_f$: 0.29 (silica gel; petroleum ether/ethyl acetate=1:2).

(13) 4-(4-pyridylamino)-6-morpholinopyrimido[5,4-d]pyrimidine

Melting point: 215–218° C.

| Calculated: | C 58.24 | H 4.99 | N 31.69 |
|---|---|---|---|
| Found: | 58.36 | 4.99 | 31.76 |

(14) 4-(6-isoquinolylamino)-6-morpholinopyrimido[5,4-d]-pyrimidine

Melting point: 208–210° C., $R_f$: 0.33 (silica gel; methylene chloride/dioxane=10:2).

(15) 4-(3-chlorobenzylamino)-6-morpholinopyrimido[5,4-d]-pyrimidine

Melting point: 160–162° C., $R_f$: 0.35 (silica gel; petroleum ether/ethyl acetate=1:1).

(16) 4-(1,2,3,4-tetrahydro-2-naphthylamino)-6-cyclopropylaminopyrimido[5,4-d]pyrimidine Prepared from 4-chloro-6-(cyclopropylamino)pyrimido[5,4-d]-pyrimidine.

Melting point: 199–201° C., $R_f$: 0.20 (silica gel; petroleum ether/ethyl acetate=1:1).

EXAMPLE 2

4-[(3-Chloro-4-fluorophenyl)amino]-6-(4-picolylamino)pyrimido[5,4-d]pyrimidine 10 ml of 4-picolylamine are added to 0.5 g of a mixture of 4-[(3-chloro-4-fluorophenyl)amino]-6-methylsulphinylpyrimido-[5,4-d]pyrimidine and 4-[(3-chloro-4-fluorophenyl)amino]-6-methylsulphinylpyrimido[5,4-d]pyrimidine at room temperature. After 12 hours, water is added and the solid is filtered off with suction. The residue is washed with ethyl acetate, filtered off with suction and recrystallized from dioxane.

Melting point: 245–250° C., $R_f$: 0.60 (alumina; methylene chloride/ethyl acetate/methanol/concentrated ammonia=10:5:1:0.05).

The following compounds can be obtained in analogy to Example 2:

(1) 4-(5-indolylamino)-6-[trans-(4-hydroxycyclohexyl)amino]pyrimido[5,4-d]pyrimidine Melting point: 210–212° C.

(2) 4-[(3-methylphenyl)amino]-6-(1-imidazolyl)pyrimido-[5,4-d]pyrimidine

Melting point: 212–214° C., $R_f$: 0.45 (silica gel; petroleum ether/ethyl acetate/methanol=10:10:2), Mass spectrum: $M^+$=303.

(3) 4-[(3-chloro-4-fluorophenyl)amino]-6-(7-methyl-2,7-diazaspiro[3.5]-2-nonyl)pyrimido[5,4-d]pyrimidine Prepared from the compounds of Examples IX and X and 7-methyl-2,7-diazaspiro[3.5]nonane (see Example 72 of EP-A-0,417,631)

Melting point: 200–202° C., $R_f$: 0.60 (alumina; petroleum ether/ethyl acetate/methanol=10:10:1).

(4) 4-[(3-chloro-4-fluorophenyl)amino]-6-[4-(1-pyrrolidinylcarbonylmethyl)-1-piperazinyl]pyrimido[5,4-d]pyrimidine Melting point: 235–237° C., $R_f$: 0.35 (alumina; petroleum ether/ethyl acetate/methanol=10:10:1).

(5) 4-[(3-chloro-4-fluorophenyl)amino]-6-[4-(morpholinocarbonylmethyl)-1-piperazinyl]pyrimido[5,4-d]pyrimidine Melting point: 198–200° C., $R_f$: 0.45 (alumina; petroleum ether/ethyl acetate/methanol=10:10:1).

(6) 4-[(3-chloro-4-fluorophenyl)amino]-6-[(4-morpholinyl)amino]pyrimido[5,4-d]pyrimidine Melting point: 228–230° C., $R_f$: 0.23 (silica gel; petroleum ether/ethyl acetate/methanol=10:10:1).

(7) 4-[(3-chloro-4-fluorophenyl)amino]-6-(2-picolylamino)pyrimido[5,4-d]pyrimidine Melting point: 220–222° C., $R_f$: 0.38 (alumina; methylene chloride/ethyl acetate/methanol=10:10:1).

(8) 4-[(3-chloro-4-fluorophenyl)amino]-6-[1-trifluoroacetyl-4-piperidinylamino]pyrimido[5,4-d]pyrimidine Prepared by reacting the compounds of Examples IX or X and XI followed by reaction with trifluoroacetic acid and subsequent reaction with trifluoroacetic anhydride.

Melting point: 230–232° C., $R_f$: 0.30 (silica gel; petroleum ether/ethyl acetate/methanol=20:10:1).

(9) 4-[(3-chloro-4-fluorophenyl)amino]-6-[4-(4-pyridyl)-1-piperidinyl]pyrimido[5,4-d]pyrimidine Melting point: 227–229° C., $R_f$: 0.43 (silica gel; petroleum ether/ethyl acetate/methanol=10:10:2).

(10) 4-[(3-chloro-4-fluorophenyl)amino]-6-[4-(2-pyridyl)-1-piperazinyl]pyrimido[5,4-d]pyrimidine Melting point: 223–225° C., $R_f$: 0.63 (silica gel; petroleum ether/ethyl acetate/methanol=10:10:0.5).

(11) 4-[(3-chloro-4-fluorophenyl)amino]-6-[3-(aminomethyl)benzylamino]pyrimido[5,4-d]pyrimidine Melting point: 179–182° C., $R_f$: 0.50 (alumina; methylene chloride/methanol=8:1).

(12) 4-[(3-chloro-4-fluorophenyl)amino]-6-[4-(aminomethyl)benzylamino]pyrimido[5,4-d]pyrimidine Melting point: 211–213° C., $R_f$: 0.55 (alumina; methylene chloride/methanol=9:1).

(13) 4-[(3-chloro-4-fluorophenyl)amino]-6-acetylaminopyrimido[5,4-d]pyrimidine

Prepared by reacting the compounds of Examples IX or X with ammonia and subsequent reaction with acetyl chloride.

Melting point: 259–263° C., $R_f$: 0.54 (alumina; methylene chloride/methanol=20:1).

(14) 4-[(3-chloro-4-fluorophenyl)amino]-6-[trans-4-(tert-butyloxycarbonylaminomethyl)cyclohexylamino]-pyrimido[5,4-d]-pyrimidine Prepared by reacting the compounds of Examples IX or X with the compound of Example XIV.

Melting point: 202–206° C., $R_f$: 0.54 (silica gel; petroleum ether/ethyl acetate/methanol=10:8:2).

| Calculated: | C 57.42 | H 5.82 | N 19.53 | Cl 7.06 |
|---|---|---|---|---|
| Found: | 57.71 | 6.09 | 19.01 | 6.85 |

(15) 4-[2-fluorenylamino]-6-(trans-4-hydroxycyclohexylamino)pyrimido[5,4-d]pyrimidine Melting point: 296–298° C., $R_f$: 0.27 (silica gel; petroleum ether/ethyl acetate/methanol=10:10:1).

(16) 4-[(3-chloro-4-fluorophenyl)amino]-6-[2-((7-methyl-2,7-diazaspiro[4.4]-2-nonyl)ethylamino]pyrimido[5,4-d]pyrimidine Prepared from the compounds of Examples IX and X and 2-[7-methyl-2,7-diazaspiro[4.4]-2-nonyl]ethylamine.

$R_f$: 0.50 (alumina; methylene chloride/methanol=20:1), orange oil, Mass spectrum: $M^+$=456/458 (Cl).

(17) 4-[(3-chloro-4-fluorophenyl)amino]-6-[4-(trans-4-hydroxycyclohexylamino)cyclohexylamino]pyrimido[5,4-d]pyrimidine Prepared by reacting the compounds of Examples IX or X with 4-hydroxycyclohexylamine, oxidation with Dess-Martin reagent and subsequent reductive amination with sodium cyanoborohydride and trans-4-hydroxycyclohexylamine.

Melting point of the 1:1-cis/trans mixture: 245–255° C., $R_f$: 0.60 (alumina; petroleum ether/ethyl acetate/methanol/concentrated ammonia=10:10:3:0.05).

(18) 4-[(3-chloro-4-fluorophenyl)amino]-6-(endo-tropinylamino)pyrimido[5,4-d]pyrimidine Melting point: 168–170° C., $R_f$: 0.30 (alumina; petroleum ether/ethyl acetate/methanol=10:10:1).

| Calculated: | C 58.03 | H 5.11 | N 23.68 |
|---|---|---|---|
| Found: | 58.02 | 5.13 | 23.27 |

(19) 4-[(3-chloro-4-fluorophenyl)amino]-6-(exo-tropinylamino)pyrimido[5,4-d]pyrimidine Melting point: 209–211° C., $R_f$: 0.28 (alumina; petroleum ether/ethyl acetate/methanol=10:10:1).

(20) 4-[(3-chloro-4-fluorophenyl)amino]-6-(3-oxo-1-piperazinyl)pyrimido[5,4-d]pyrimidine Melting point: 244–246° C., $R_f$: 0.19 (silica gel; methylene chloride/methanol/concentrated ammonia=98:2:1).

(21) 4-[(3-chloro-4-fluorophenyl)amino]-2-methyl-6-[4-amino-1-piperidinyl]pyrimido[5,4-d]pyrimidine Melting point: 156–163° C., $R_f$: 0.19 (silica gel; methylene chloride/methanol/concentrated ammonia=95:5:2).

(22) 4-[(3-chloro-4-fluorophenyl)amino]-2-methyl-6-cyclopropylaminopyrimido[5,4-d]pyrimidine Melting point: 213–218° C., $R_f$: 0.75 (silica gel; petroleum ether/ethyl acetate/methanol=5:4:1.5).

(23) 4-[(3-chloro-4-fluorophenyl)amino]-6-[4-(trans-4-hydroxycyclohexylamino)-1-piperidinyl]pyrimido[5,4-d]pyrimidine

(24) 4-[(3-chloro-4-fluorophenyl)amino]-6-[4-(4-piperidinylamino)-1-piperidinyl]pyrimido[5,4-d]pyrimidine Prepared from the compounds of Example X by reacting with 4-aminopiperidine, subsequent reaction with N-tert-butoxycarbonyl-4-piperidone and sodium cyanoborohydride and subsequent elimination of the tert-butoxycarbonyl protective group with trifluoroacetic acid.

Melting point: 210–212° C., $R_f$: 0.40 (alumina; ethyl acetate/methanol/concentrated ammonia=10:5:0.1).

(25) 4-[(3-chloro-4-fluorophenyl)amino]-6-[4-(4-piperidinylmethyl)-1-piperidinyl]pyrimido[5,4-d]pyrimidine

(26) 4-[(3-chloro-4-fluorophenyl)amino]-6-[4-(morpholinocarbonylamino)-1-piperidinyl]pyrimido[5,4-d]pyrimidine Prepared from the compounds of Example X by reacting with 4-aminopiperidine and subsequent reaction with morpholine-N-carbonyl chloride.

Melting point: 248–252° C., $R_f$: 0.76 (alumina; methylene chloride/methanol=10:0.7).

(27) 4-[(3-chloro-4-fluorophenyl)amino]-6-[4-((trans-4-hydroxycyclohexylamino)methyl)-1-piperidinyl]pyrimido[5,4-d]pyrimidine

(28) 4-[(3-chloro-4-fluorophenyl)amino]-6-[4-(4-amino-1-piperidinylmethyl)-1-piperidinyl]pyrimido[5,4-d]pyrimidine

(29) 4-[(3-chloro-4-fluorophenyl)amino]-6-[4-(4-methylamino-1-piperidinylmethyl)-1-piperidinyl]pyrimido[5,4-d]pyrimidine

(30) 4-[(3-chloro-4-fluorophenyl)amino]-6-[4-(4-dimethylamino-1-piperidinylmethyl)-1-piperidinyl]pyrimido[5,4-d]pyrimidine

(31) 4-[(3-chloro-4-fluorophenyl)amino]-6-[4-(4-ethylamino-1-piperidinylmethyl)-1-piperidinyl]pyrimido[5,4-d]pyrimidine

(32) 4-[(3-chloro-4-fluorophenyl)amino]-6-[4-(3-oxo-1-piperazinylcarbonyl)-1-piperidinyl]pyrimido[5,4-d]pyrimidine

(33) 4-[(3-chloro-4-fluorophenyl)amino]-6-[4-(4-methyl-3-oxo-1-piperazinylcarbonyl)-1-piperidinyl]pyrimido[5,4-d]pyrimidine

(34) 4-[(3-chloro-4-fluorophenyl)amino]-6-[4-(1-acetyl-4-piperidinyl)-1-piperidinyl]pyrimido[5,4-d]pyrimidine Prepared from the compounds of Example 10 by reacting with 4,4'-bipiperidine and subsequent reaction with acetic anhydride.

Melting point: 208–209° C., $R_f$: 0.50 (alumina; petroleum ether/ethyl acetate/methanol=10:10:1).

(35) 4-[(3-chloro-4-fluorophenyl)amino]-6-[4-(1-methoxycarbonyl-4-piperidinyl)-1-piperidinyl]pyrimido[5,4-d]pyrimidine Prepared from the compounds of Example X by reacting with 4,4'-bipiperidine and subsequent reaction with methyl chloroformate.

Melting point: 155–157° C., $R_f$: 0.45 (alumina; petroleum ether/ethyl acetate=1:1).

(36) 4-[(3-chloro-4-fluorophenyl)amino]-6-[4-(1-methylsulphonyl-4-piperidinyl)-1-piperidinyl]pyrimido[5,4-d]pyrimidine

(37) 4-[(3-chloro-4-fluorophenyl)amino]-6-[4-(1-(morpholinocarbonyl)-4-piperidinyl)-1-piperidinyl]pyrimido[5,4-d]pyrimidine

(38) 4-[(3-chloro-4-fluorophenyl)amino]-6-[4-(1-dimethylaminocarbonyl-4-piperidinyl)-1-piperidinyl]pyrimido[5,4-d]pyrimidine

(39) 4-[(3-chloro-4-fluorophenyl)amino]-6-[3-(morpholinocarbonylamino)-1-pyrrolidinyl]pyrimido[5,4-d]pyrimidine Prepared from the compounds of Example X by reacting with 3-aminopyrrolidine and subsequent reaction with morpholine-N-carbonyl chloride.

Melting point: 179–184° C., $R_f$: 0.72 (silica gel; methylene chloride/methanol=10:2).

(40) 4-[(3-chloro-4-fluorophenyl)amino]-6-[4-methyl-3-oxo-1-piperazinyl]pyrimido[5,4-d]pyrimidine

(41) 4-[(3-chloro-4-fluorophenyl)amino]-6-[4-(4-piperidinyl)-1-piperazinyl]pyrimido[5,4-d]pyrimidine Prepared from the compounds of Example X by reacting with piperazine and subsequent reaction with N-tert-butoxycarbonyl-4-piperidone and sodium cyanoborohydride and subsequent elimination of the tert-butoxycarbonyl protective group with trifluoroacetic acid.

Melting point: 205–207° C., $R_f$: 0.58 (alumina; petroleum ether/ethyl acetate/methanol=10:10:2).

(42) 4-[(3-chloro-4-fluorophenyl)amino]-6-[4-(1-methyl-4-piperidinyl)-1-piperazinyl]pyrimido[5,4-d]pyrimidine Prepared from the compounds of Example X by reacting with piperazine and subsequent reaction with N-methyl-4-piperidone and sodium cyanoborohydride.

Melting point: 191–193° C., $R_f$: 0.25 (alumina; petroleum ether/ethyl acetate/methanol=10:10:1).

(43) 4-[(3-chloro-4-fluorophenyl)amino]-6-[4-(1-acetyl-4-piperidinyl)-1-piperazinyl]pyrimido[5,4-d]pyrimidine Prepared from the compounds of Example X by reacting with piperazine and subsequent reaction with N-acetyl-4-piperidone and sodium cyanoborohydride.

Melting point: 230–233° C., $R_f$: 0.58 (alumina; petroleum ether/ethyl acetate/methanol=10:10:2).

(44) 4-[(3-chloro-4-fluorophenyl)amino]-6-[4-(1-methoxycarbonyl-4-piperidinyl)-1-piperazinyl]pyrimido[5,4-d]pyrimidine

(45) 4-[(3-chloro-4-fluorophenyl)amino]-6-[4-(morpholinocarbonyl)phenylamino]pyrimido[5,4-d]pyrimidine

(46) 4-[(3-chloro-4-fluorophenyl)amino]-6-[4-(1-pyrrolidinylcarbonyl)phenylamino]pyrimido[5,4-d]pyrimidine

(47) 4-[(3-chloro-4-fluorophenyl)amino]-6-[4-(3-oxo-1-piperazinyl)phenylamino]pyrimido[5,4-d]pyrimidine

(48) 4-[(3-chloro-4-fluorophenyl)amino]-6-[4-(4-methyl-3-oxo-1-piperazinyl)phenylamino]pyrimido[5,4-d]pyrimidine

(49) 4-[(3-chloro-4-fluorophenyl)amino]-6-[4-(3-carboxypropylamino)cyclohexylamino]pyrimido[5,4-d]pyrimidine

(50) 4-[(3-chloro-4-fluorophenyl)amino]-6-[4-(morpholinocarbonylamino)cyclohexylamino]pyrimido[5,4-d]pyrimidine

(51) 4-[(3-chloro-4-fluorophenyl)amino]-6-[4-((4-tetrahydropyranylamino)carbonyl)cyclohexylamino]pyrimido[5,4-d]pyrimidine Prepared from the compounds of Example X and methyl trans-4-aminocyclohexanecarboxylate, subsequent hydrolysis with sodium hydroxide solution and subsequent reaction with N-dimethylaminopropyl-N'-ethylcarbodiimide, 3-hydroxy-1,2,3-benzotriazin-4(3H)-one, triethylamine and the compound of Example XVII.

Melting point: 307–313° C., $R_f$: 0.45 (silica gel; petroleum ether/ethyl acetate/methanol=10:8:3).

(52) 4-[(3-chloro-4-fluorophenyl)amino]-6-[4-(2-hydroxyethylaminocarbonyl)cyclohexylamino]pyrimido[S,4-d]pyrimidine

(53) 4-[(3-chloro-4-fluorophenyl)amino]-6-[4-(2-methoxyethylaminocarbonyl)cyclohexylamino]pyrimido[5,4-d]pyrimidine Prepared from the compounds of Example X and methyl trans-4-aminocyclohexanecarboxylate, subsequent hydrolysis with sodium hydroxide solution and subsequent reaction with N-dimethylaminopropyl-N'-ethylcarbodiimide, 3-hydroxy-1,2,3-benzotriazin-4(3H)-one, triethylamine and 2-methoxyethylamine. Melting point: 243–246° C., $R_f$: 0.46 (silica gel; petroleum ether/ethyl acetate/methanol=10:8:3).

(54) 4-[(3-chloro-4-fluorophenyl)amino]-6-[4-(trans-4-hydroxycyclohexylaminocarbonyl)cyclohexylamino]pyrimido[5,4-d]pyrimidine Prepared from the compounds of Example X and methyl trans-4-aminocyclohexanecarboxylate, subsequent hydrolysis with sodium hydroxide solution and subsequent reaction with N-dimethylaminopropyl-N'-ethylcarbodiimide, trans-4-aminocyclohexanol, 3-hydroxy-1,2,3-benzotriazin-4(3H)-one and triethylamine.

Melting point: 301–305° C., $R_f$: 0.46 (alumina; methylene chloride/methanol=10:0.8).

(55) 4-[(3-chloro-4-fluorophenyl)amino]-6-[4-((4-amino-1-piperidinyl)carbonyl)cyclohexylamino]pyrimido[5,4-d]pyrimidine

(56) 4-[(3-chloro-4-fluorophenyl)amino]-6-[4-((4-dimethylamino-1-piperidinyl)carbonyl)cyclohexylamino]pyrimido[5,4-d]pyrimidine

(57) 4-[(3-chloro-4-fluorophenyl)amino]-6-[4-((4-piperidinylamino)carbonyl)cyclohexylamino]pyrimido[5,4-d]pyrimidine

(58) 4-[(3-chloro-4-fluorophenyl)amino]-6-[4-(N-(1-methyl-4-piperidinyl)-N-methyl-amino)carbonyl)cyclohexylamino]pyrimido[5,4-d]pyrimidine

(59) 4-[(3-chloro-4-fluorophenyl)amino]-6-[4-((1-methyl-4-piperidinylamino)carbonyl)cyclohexylamino]pyrimido[5,4-d]pyrimidine

(60) 4-[(3-chloro-4-fluorophenyl)amino]-6-[4-((4-dimethylamino-1-piperidinyl)methyl)cyclohexylamino]pyrimido[5,4-d]pyrimidine

(61) 4-[(3-chloro-4-fluorophenyl)amino]-6-[4-((4-amino-1-piperidinyl)methyl)cyclohexylamino]pyrimido[5,4-d]pyrimidine

(62) 4-[(3-chloro-4-fluorophenyl)amino]-6-[4-((4-hydroxycyclohexylamino)methyl)cyclohexylamino]pyrimido[5,4-d]pyrimidine

(63) 4-[(3-chloro-4-fluorophenyl)amino]-6-[3-(morpholinocarbonylamino)cyclohexylamino]pyrimido[5,4-d]pyrimidine

(64) 4-[(3-chloro-4-fluorophenyl)amino]-6-[3-(morpholinocarbonylamino)cyclopentylamino]pyrimido[5,4-d]pyrimidine

(65) 4-[(3-chloro-4-fluorophenyl)amino]-6-[1-(4-aminocyclohexyl)-4-piperidinylamino]pyrimido[5,4-d]pyrimidine

(66) 4-[(3-chloro-4-fluorophenyl)amino]-6-[2-(4-amino-1-piperidinyl)ethylamino]pyrimido[5,4-d]pyrimidine

(67) 4-[(3-chloro-4-fluorophenyl)amino]-6-(4-formyl-1-piperazinylcarbonylmethylamino)pyrimido[5,4-d]pyrimidine

(68) 4-[(3-chloro-4-fluorophenyl)amino]-6-[4-methoxycarbonyl-1-piperazinylcarbonylmethylamino]pyrimido[5,4-d]pyrimidine

(69) 4-[(3-chloro-4-fluorophenyl)amino]-6-[1-(4-formyl-1-piperazinylcarbonyl)ethylamino]pyrimido[5,4-d]pyrimidine

(70) 4-[(3-chloro-4-fluorophenyl)amino]-6-[1-(4-methoxycarbonyl-1-piperazinylcarbonyl)ethylamino]pyrimido[5,4-d]pyrimidine

(71) 4-[(3-chloro-4-fluorophenyl)amino]-6-[1,8-diazaspiro-[4.5]-8-decyl]pyrimido[5,4-d]pyrimidine

(72) 4-[(3-chloro-4-fluorophenyl)amino]-6-[3,9-diazaspiro-[5.5]-3-undecyl]pyrimido[5,4-d]pyrimidine

(73) 4-[(3-chloro-4-fluorophenyl)amino]-6-[2,7-diazaspiro-[3.5]-2-nonyl]pyrimido[5,4-d]pyrimidine

(74) 4-[(3-chloro-4-fluorophenyl)amino]-6-[2,7-diazaspiro-[3.5]-7-nonyl]pyrimido[5,4-d]pyrimidine

(75) 8-[(3-chloro-4-fluorophenyl)amino]-2-(4-amino-1-piperidinyl)-4-methylpyrimido[5,4-d]pyrimidine

(76) 8-[(3-chloro-4-fluorophenyl)amino]-2-[4-(4-piperidinyl)-1-piperidinyl]-4-methylpyrimido[5,4-d]pyrimidine

(77) 8-[(3-chloro-4-fluorophenyl)amino]-2-[4-(1-methyl-4-piperidinyl)-1-piperidinyl]-4-methylpyrimido[5,4-d]pyrimidine

(78) 8-[(3-chloro-4-fluorophenyl)amino]-2-[2-amino-2-methyl-1-propylamino]-4-methylpyrimido[5,4-d]pyrimidine

(79) 8-[(3-chloro-4-fluorophenyl)amino]-2-(4-piperidinylamino)-4-methylpyrimido[5,4-d]pyrimidine

(80) 8-[(3-chloro-4-fluorophenyl)amino]-2-(1-methyl-4-piperidinylamino)-4-methylpyrimido[5,4-d]pyrimidine Prepared from the compounds of Examples X and XV.

Melting point: 215–217° C., $R_f$: 0.42 (silica gel; methylene chloride/methanol/concentrated ammonia=10:1.5:0.1).

(81) 8-[(3-chloro-4-fluorophenyl)amino]-2-[N-methyl-N-(1-methyl-4-piperidinyl)amino]-4-methylpyrimido[5,4-d]pyrimidine

(82) 8-[(3-chloro-4-fluorophenyl)amino]-2-(trans-4-hydroxycyclohexylamino)-4-methylpyrimido[5,4-d]pyrimidine

(83) 8-[(3-chloro-4-fluorophenyl)amino]-2-[trans-4-(morpholinocarbonyl)cyclohexylamino]-4-methylpyrimido[5,4-d]pyrimidine

(84) 4-[(3-chloro-4-fluorophenyl)amino]-6-(trans-4-hydroxycyclohexylamino)-2-methylpyrimido[5,4-d]pyrimidine

(85) 4-[(3-chloro-4-fluorophenyl)amino]-6-[2-methyl-2,7-diazaspiro[4.4]-7-nonyl]pyrimido[5,4-d]pyrimidine Melting point: 148–153° C., $R_f$: 0.51 (alumina; methylene chloride/methanol=10:0.3).

(86) 4-[(3-chloro-4-fluorophenyl)amino]-6-[6-methyl-2,6-diazaspiro[3.4]-2-octyl]pyrimido[5,4-d]pyrimidine Melting point: 136–139° C., $R_f$: 0.51 (alumina; methylene chloride/methanol=10:0.3).

(87) 4-[(3-chloro-4-fluorophenyl)amino]-6-[2-methyl-2,6-diazaspiro[3.4]-6-octyl]pyrimido[5,4-d]pyrimidine Melting point: 115–120° C., $R_f$: 0.55 (alumina; methylene chloride/methanol=10:0.3).

(88) 4-[(3-chloro-4-fluorophenyl)amino]-6-[9-amino-3-azaspiro[5.5]-3-undecyl]pyrimido[5,4-d]pyrimidine

(89) 4-[(3-chloro-4-fluorophenyl)amino]-6-[8-amino-2-azaspiro[4.5]-2-decyl]pyrimido[5,4-d]pyrimidine

(90) 4-[(3-chloro-4-fluorophenyl)amino]-6-[4-(trans-4-((3-methoxycarbonyl-1-propyl)amino)cyclohexylamino]pyrimido-[5,4-d]pyrimidine Prepared from the compounds of Example X and trans-4-aminocyclohexanol, oxidation with Dess-Martin reagent and subsequent reductive amination with methyl 4-aminobutyrate and sodium cyanoborohydride.

Melting point: 80–85° C., $R_f$: 0.45 (alumina; petroleum ether/ethyl acetate/methanol=10:10:2).

(91) 4-[(4-amino-3,5-dibromophenyl)amino]-6-(exo-tropinylamino)pyrimido[5,4-d]pyrimidine Melting point: 204–206° C., $R_f$: 0.33 (alumina; petroleum ether/ethyl acetate/methanol=10:10:2).

(92) 4-[(3-chloro-4-fluorophenyl)amino]-6-[4-(2-(4-piperidinyl)-1-ethyl)-1-piperidinyl]pyrimido[5,4-d]pyrimidine Melting point: 112–114° C., $R_f$: 0.20 (alumina; methylene chloride/ethyl acetate/methanol=10:5:1).

(93) 4-[(3-chloro-4-fluorophenyl)amino]-6-[4-(3-(4-piperidinyl)-1-propyl)-1-piperidinyl]pyrimido[5,4-d]pyrimidine Melting point: 128–130° C., $R_f$: 0.25 (alumina; methylene chloride/ethyl acetate/methanol=10:5:5).

(94) 4-[(3-chloro-4-fluorophenyl)amino]-6-[4-(4-aminocyclohexylmethyl)cyclohexylamino]pyrimido[5,4-d]pyrimidine Melting point: 164–166° C., $R_f$: 0.25 (alumina; methylene chloride/ethyl acetate/methanol=10:10:2).

(95) 4-[(3-chloro-4-fluorophenyl)amino]-6-[4-(1-methyl-4-piperidinylamino)-1-piperidinyl]pyrimido[5,4-d]pyrimidine Prepared from the compounds of Example X and 4-hydroxypiperidine, oxidation with Dess-Martin reagent and subsequent reductive amination with 4-amino-1-methylpiperidine and sodium cyanoborohydride.

Melting point: 155–156° C., $R_f$: 0.25 (alumina; petroleum ether/ethyl acetate/methanol=10:10:2).

(96) 4-[(3-chloro-4-fluorophenyl)amino]-6-[1-(1-methyl-4-piperidinyl)-4-piperidinylamino]pyrimido[5,4-d]pyrimidine Prepared from the compounds of Example X and 4-amino-1-tert-butyloxycarbonylpiperidine, elimination of the tert-butyloxycarbonyl protective group with trifluoroacetic acid and subsequent reductive amination with N-methyl-4-piperidone and sodium triacetoxyborohydride.

Melting point: 184–188° C., $R_f$: 0.47 (alumina; methylene chloride/methanol/concentrated ammonia—30:1:0.1).

(97) 4-[(4-phenoxyphenyl)amino]-6-(exo-tropinylamino)pyrimido[5,4-d]pyrimidine

Melting point: 163–165° C., $R_f$: 0.51 (alumina; methylene chloride/ethyl acetate/methanol=10:3:1).

(98) 4-[(3-chloro-4-fluorophenyl)amino]-6-[4-(4-pyridyl)-1-piperazinyl]pyrimido[5,4-d]pyrimidine Melting point: 248–250° C., $R_f$: 0.69 (alumina; methylene chloride/methanol=10:0.3).

(99) 4-[(3-chloro-4-fluorophenyl)amino]-6-[4-(2-(1-methyl-4-piperidinyl)-1-ethyl)-1-piperidinyl]pyrimido[5,4-d]pyrimidine Prepared from compound 92 of Example 2 by reductive amination with formaldehyde and sodium cyanoborohydride.

Melting point: 159–163° C., $R_f$: 0.50 (alumina; methylene chloride/methanol=80:1).

(100) 4-[(3-chloro-4-fluorophenyl)amino]-6-[4-(3-(1-methyl-4-piperidinyl)-1-propyl)-1-piperidinyl]pyrimido[5,4-d]pyrimidine Prepared from compound 93 of Example 2 by reductive amination with formaldehyde and sodium cyanoborohydride.

Melting point: 142–145° C., $R_f$: 0.51 (alumina; methylene chloride/methanol=80:1).

EXAMPLE 3

| Coated tablets with 75 mg of active substance | |
|---|---|
| 1 Tablet core contains: | |
| Active substance | 75.0 mg |
| Calcium phosphate | 93.0 mg |
| Maize starch | 35.5 mg |
| Polyvinylpyrrolidone | 10.0 mg |
| Hydroxypropylmethylcellulose | 15.0 mg |
| Magnesium stearate | 1.5 mg |
| | 230.0 mg |

Production

The active substance is mixed with calcium phosphate, maize starch, polyvinylpyrrolidone, hydroxypropylmethylcellulose and half of the stated amount of magnesium stearate. Slugs with a diameter of about 13 mm are produced in a tabletting machine and are rubbed through a screen with a mesh width of 1.5 mm in a suitable machine and are mixed with the remaining amount of magnesium stearate. These granules are compressed to tablets of the required shape in a tabletting machine.

Core weight: 230 mg

Punch: 9 mm, convex

The tablet cores produced in this way are coated with a film essentially consisting of hydroxypropylmethylcellulose. The finished film-coated tablets are polished with beeswax.

Coated tablet weight: 245 mg

EXAMPLE 4

| Tablets with 100 mg of active substance | |
| --- | --- |
| Composition: 1 Tablet contains: | |
| Active substance | 100.0 mg |
| Lactose | 80.0 mg |
| Maize starch | 34.0 mg |
| Polyvinylpyrrolidone | 4.0 mg |
| Magnesium stearate | 2.0 mg |
| | 220.0 mg |

Production process

Active substance, lactose and starch are mixed and moistened uniformly with an aqueous solution of polyvinylpyrrolidone. After the moist composition has been screened (mesh width 2.0 mm) and dried on trays in an oven at 50° C., it is screened again (mesh width 1.5 mm) and the lubricant is mixed in. The mixture ready for compression is converted into tablets.

Tablet weight: 220 mg

Diameter: 10 mm, biplanar with bevel on both sides and score on one side.

EXAMPLE 5

| Tablets with 150 mg of active substance | |
| --- | --- |
| Composition: 1 Tablet contains: | |
| Active substance | 150.0 mg |
| Lactose powder | 89.0 mg |
| Maize starch | 40.0 mg |
| Colloidal silica | 10.0 mg |
| Polyvinylpyrrolidone | 10.0 mg |
| Magnesium stearate | 1.0 mg |
| | 300.0 mg |

Production

The active substance is mixed with lactose, maize starch and silica, moistened with a 20% strength aqueous polyvinylpyrrolidone solution and forced through a screen with a mesh width of 1.5 mm.

The granules are dried at 45° C. and again rubbed through the same screen and mixed with the stated amount of magnesium stearate. Tablets are compressed from the mixture.

Tablet weight: 300 mg

Punch: 10 mm, planar

EXAMPLE 6

| Hard gelatin capsules with 150 mg of active substance | | |
| --- | --- | --- |
| 1 Capsule contains: | | |
| Active substance | | 150.0 mg |
| Maize starch, dry | ca. | 180.0 mg |
| Lactose powder | ca. | 87.0 mg |
| Magnesium stearate | | 3.0 mg |
| | ca. | 420.0 mg |

Production

The active substance is mixed with the ancillary substances, passed through a screen with a mesh width of 0.75 mm and mixed homogeneously in a suitable apparatus.

The final mixture is packed into hard gelatin capsules of size 1.

Capsule contents: about 320 mg

Capsule shell: Hard gelatin capsule size 1.

EXAMPLE 7

| Suppositories with 150 mg of active substance | |
| --- | --- |
| 1 Suppository contains: | |
| Active substance | 150.0 mg |
| Polyethylene glycol 1500 | 550.0 mg |
| Polyethylene glycol 6000 | 460.0 mg |
| Polyoxyethylene sorbitan monostearate | 840.0 mg |
| | 2,000.0 mg |

Production

After the suppository base has been melted, the active substance is homogeneously dispersed therein and the melt is poured into precooled moulds.

EXAMPLE 8

| Suspension with 50 mg of active substance | |
| --- | --- |
| 100 ml of suspension contains: | |
| Active substance | 1.00 g |
| carboxymethylcellulose Na salt | 0.10 g |
| Methyl p-hydroxybenzoate | 0.05 g |
| Propyl p-hydroxybenzoate | 0.01 g |
| Sucrose | 10.00 g |
| Glycerol | 5.00 g |
| Sorbitol solution, 70% strength | 20.00 g |
| Flavouring | 0.30 g |
| Distilled water ad | 100 ml |

Production

Distilled water is heated to 70° C. Methyl and propyl p-hydroxybenzoates, and glycerol and carboxymethylcellulose sodium salt are dissolved therein with stirring. The solution is cooled to room temperature and, while stirring, the active substance is added and homogeneously dispersed. After the sugar, the sorbitol solution and the flavouring have been added and dissolved, the suspension is evacuated with stirring for deaeration.

5 ml of suspension contain 50 mg of active substance.

EXAMPLE 9

| Ampoules with 10 mg of active substance | |
|---|---|
| Composition: | |
| Active substance | 10.0 mg |
| 0.01 N hydrochloric acid q.s. | |
| Doubled-distilled water ad | 2.0 ml |

Production

The active substance is dissolved in the required amount of 0.01 N HCl, made isotonic with sodium chloride, sterilized by filtration and dispensed into 2 ml ampoules.

EXAMPLE 10

| Ampoules with 50 mg of active substance | |
|---|---|
| Composition: | |
| Active substance | 50.0 mg |
| 0.01 N hydrochloric acid q.s. | |
| Doubled-distilled water ad | 10.0 ml |

Production

The active substance is dissolved in the required amount of 0.01 N HCl, made isotonic with sodium chloride, sterilized by filtration and dispensed into 10 ml ampoules.

What is claimed is:

1. A compound of the formula

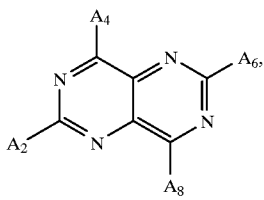

(I)

in which, with the proviso that at least
  (i) $A_2$ represents an alkyl group,
  (ii) $A_8$ represents an alkyl group,
  (iii) $A_4$ represents an $R_dNR_e$ group or
  (iv) $A_6$ represents an $R_g$ group,
$A_2$ and $A_8$, which can be identical or different, each denote a hydrogen atom or an alkyl group,
$A_4$ denotes an $R_aNR_b$ group or an $R_dNR_e$ group and
$A_6$ denotes an $R_c$ group or an $R_g$ group in which
  $R_a$ denotes a hydrogen atom or an alkyl group,
  $R_b$ denotes a phenyl group substituted by the radicals $R_1$ to $R_3$, where
    $R_1$ denotes a hydrogen, fluorine, chlorine, bromine or iodine atom,
      an alkyl, hydroxyl, alkoxy or $C_{3-6}$-cycloalkyl group,
      a $C_{2-5}$-alkenyl or $C_{2-5}$-alkynyl group,
      a phenyl, phenoxy, phenylalkyl, phenylalkoxy, alkoxyalkyl, phenoxyalkyl, carboxyalkyl, cyanoalkyl, alkylsulphenyl, alkylsulphinyl, nitro, 1-pyrrolidinyl, 1-piperidinyl, morpholino, alkylcarbonylamino, N-alkyl-alkylcarbonylamino, alkylsulphonylamino, N-alkyl-alkylsulphonylamino, trifluoromethylsulphonylamino, N-alkyl-trifluoromethylsulphonylamino or cyano group,
      a methyl or methoxy group which is substituted by 1 to 3 fluorine atoms,
      an ethyl or ethoxy group which is substituted by 1 to 5 fluorine atoms,
    $R_2$ denotes a hydrogen, fluorine, chlorine or bromine atom, an alkyl, trifluoromethyl, amino, alkylamino, dialkylamino, alkylcarbonylamino, alkylsulphonylamino, trifluoromethylsulphonylamino, hydroxyl or alkoxy group,
    $R_3$ denotes a hydrogen, fluorine, chlorine or bromine atom or an alkyl group, or
    $R_2$ together with $R_3$, when these are bonded to adjacent carbon atoms, also represent a methylenedioxy or n-$C_{3-6}$-alkylene group or a 1,3-butadiene-1,4-diyl group which is optionally substituted by a fluorine, chlorine or bromine atom, by an alkyl, alkoxy or trifluoromethyl group, and
  $R_c$ denotes a 1-azetidinyl group,
    a 1-pyrrolidinyl group which can be substituted by 1 to 2 alkyl groups, by one phenyl, carboxyl, hydroxyalkyl, aminoalkyl, alkylaminoalkyl, dialkylaminoalkyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinyl-carbonyl group or in position 3 also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group,
    a 1-piperidinyl group which can be substituted by 1 to 2 alkyl groups, by one phenyl, hydroxyalkyl, aminoalkyl, alkylaminoalkyl, dialkylaminoalkyl, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 or 4 also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group,
    a group of the formula

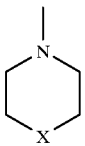

which is optionally substituted by 1 or 2 alkyl groups and wherein X is an oxygen or sulphur atom, a carbonyl, sulphinyl, sulphonyl, imino, alkylimino, hydroxy-$C_{2-4}$-alkyl-imino, alkoxy-$C_{2-4}$-alkylimino, aminocarbonylalkylimino, alkylaminocarbonylalkylimino, dialkylaminocarbonylalkylimino, amino-$C_{2-4}$-alkylimino, alkylamino-$C_{2-4}$-alkylimino, dialkylamino-$C_{2-4}$-alkylimino, phenylimino, phenylalkylimino, alkylcarbonylimino, alkylsulphonylimino, phenylcarbonylimino or a phenylsulphonylimino group,
    a 1-azacyclohept-1-yl group, or an analog thereof having in position 4, instead of a methylene group, an oxygen atom, an imino, N-alkylimino, N-phenylimino, N-phenylalkylimino, N-alkylcarbonylimino, N-alkylsulphonylimino, N-phenylcarbonylimino or a N-phenylsulphonylimino group, wherein said 1-azacyclohept-1-yl group or analog thereof is optionally substituted by 1 or 2 alkyl groups, or a 5- to 7-membered alkyleneimino group which is optionally substituted by 1 or 2 alkyl groups and which is linked via a carbon atom to a carbon atom of a 5- to 7-membered alkyleneimino group in which the nitrogen atom can be substituted by an alkyl group, an ($R_4NR_5$) group in which $R_4$ denotes a hydrogen atom or a $C_{1-6}$-alkyl group which can be substituted by a hydroxyl or alkoxy group, and $R_5$ denotes a hydrogen atom, a $C_{1-8}$-alkyl group which can be substituted by a phenyl, $C_{3-6}$-cycloalkyl, hydroxyl, alkoxy, cyano, carboxyl, alkoxycarbonyl, aminocarbonyl, alkylaminocarbonyl, dialkylaminocarbonyl, (2-hydroxyethyl)aminocarbonyl, 1-pyrrolidinylcarbonyl, 1-piperidinylcarbonyl, morpholinocarbonyl, 1-piperazinylcarbonyl, 4-alkyl-1-piperazinylcarbonyl, amino, formylamino, alkylamino, dialkylamino, alkylcarbonylamino, N-alkyl-alkylcarbonylamino, alkoxycarbonylamino, N-alkylalkoxycarbonylamino, alkylsulphonylamino, N-alkyl-alkylsulphonylamino, phenylcarbonylamino, N-alkyl-phenylcarbonylamino, phenylsulphonylamino, N-alkyl-phenylsulphonylamino, alkylsulphenyl, alkylsulphinyl, alkylsulphonyl, 1-pyrrolidinyl, 2-oxo-1-pyrrolidinyl, 1-piperidinyl, 2-oxo-1-piperidinyl, morpholino, 1-piperazinyl, 4-alkyl-1-piperazinyl, 4-alkylcarbonyl-1-piperazinyl, 4-alkylsulphonyl-1-piperazinyl, 4-alkoxycarbonyl-1-piperazinyl, 4-cyano-1-piperazinyl, 4-formyl-1-piperazinyl, 4-aminocarbonyl-1-piperazinyl, 4-alkylaminocarbonyl-1-piperazinyl or 4-dialkylaminocarbonyl-1-piperazinyl or an ($R_8NR_7$)—CO—$NR_6$ group, where $R_6$, $R_7$ and $R_8$, which can be identical or different, each represent a hydrogen atom or an alkyl group or $R_6$ and $R_7$ together represent an n-$C_{2-4}$-alkylene group and $R_8$ represents a hydrogen atom or an alkyl group, or R5 denotes a 2,2,2-trifluoroethyl group, or R5 denotes a $C_{3-10}$-alkyl group substituted by 2 to 5 hydroxyl groups, or R5 denotes a $C_{3-5}$-alkyl group substituted by one hydroxyl and additionally by one amino group, or R5 denotes an alkenyl or alkynyl group which is optionally substituted by a phenyl group and has in each case 3 to 6 carbon atoms, it not being possible for the vinyl or ethynyl moiety to be linked to the nitrogen atom, or R5 denotes a $C_{2-4}$-alkyl group which is substituted by a $C_{2-4}$-alkoxy group which is substituted in the ω position by a hydroxyl or alkoxy group, or R5 denotes a phenyl group, or R5 denotes a phenyl group which is substituted by an alkylcarbonylamino, N-alkylalkylcarbonylamino, (2-hydroxyethyl)amino, di-(2-hydroxyethyl)amino, N-alkyl-(2-hydroxyethyl)amino, amino, alkylamino or dialkylamino group or by an ($R_8NR_7$)—CO—$NR_6$ group, where $R_6$ to $R_8$ are defined as mentioned above in this claim, or R5 denotes a phenyl group which is substituted by a 1-pyrrolidinyl, 1-piperidinyl, 2-oxo-1-pyrrolidinyl, 2-oxo-1-piperidinyl, morpholino, 1-piperazinyl or 4-alkyl-1-piperazinyl group, where the abovementioned heterocyclic moieties can be substituted on the carbon framework in each case by 1 or 2 alkyl groups or by one hydroxyalkyl group, or R5 denotes a $C_{3-7}$-cycloalkyl group which can be substituted by 1 or 2 alkyl groups, by one phenyl, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, or R5 denotes a $C_{5-7}$-cycloalkyl group which is optionally substituted by 1 or 2 methyl groups and which is substituted by a hydroxymethyl, cyano, hydroxyl, alkoxy, amino, alkylamino, dialkylamino, 2-hydroxyethylamino, di-(2-hydroxyethyl)amino, N-alkyl-2-hydroxyethylamino, alkoxycarbonylamino, N-alkyl-alkoxycarbonylamino, alkylcarbonylamino, N-alkyl-alkylcarbonylamino, alkylsulphonylamino, N-alkylalkylsulphonylamino, phenylcarbonylamino, N-alkyl-phenylcarbonylamino, phenylsulphonylamino, N-alkylphenylsulphonylamino or by an ($R_8NR_7$)—CO—$NR_6$ group, where $R_6$ to $R_8$ are defined as mentioned above in this claim, or R5 denotes a $C_{5-7}$-cycloalkyl group which is optionally substituted by 1 or 2 methyl groups and which is substituted by a 1-pyrrolidinyl, 1-piperidinyl, 2-oxo-1-pyrrolidinyl, 2-oxo-1-piperidinyl, morpholino, 1-piperazinyl, 4-alkyl-1-piperazinyl or 4-alkylcarbonyl-1-piperazinyl group, it being possible for the abovementioned heterocyclic moieties to be substituted on the carbon framework in each case by 1 or 2 alkyl groups, or R5 denotes a $C_{5-7}$-cycloalkenyl group which is optionally substituted by 1 or 2 alkyl groups, where the vinyl moiety cannot be bonded to the nitrogen atom of the ($R_4NR_5$) group, or R5 denotes a tetrahydrofurfuryl group, or R5 denotes a cyclopentyl group in which the methylene group in position 3 is replaced by an oxygen atom, an imino, alkylimino, alkylcarbonylimino, formylimino, aminocarbonylimino, alkylaminocarbonylimino, alkoxycarbonylimino, alkylsulphonylimino, dialkylaminocarbonylimino or cyanoimino group, a cyclohexyl group in which the methylene group in position 3 is replaced by an imino, alkylimino, alkylcarbonylimino, alkoxycarbonylimino or alkylsulphonylimino group, or R5 denotes a cyclohexyl group in which the methylene group in position 4 is replaced by an oxygen atom, an imino, N-alkylimino-, N-phenylimino, N-phenylalkylimino, N-formylimino, N-alkylcarbonylimino, N-phenylcarbonylimino, N-alkoxycarbonylimino, N-cyanoimino-, N-aminocarbonylimino-, N-alkylaminocarbonyl-imino, N,N-dialkylaminocarbonylimino, N-alkylsulphonylimino or N-phenylsulphonylimino group, or R5 denotes a cyclohexyl group in which one methylene group is replaced by a carbonyl group, or R5 denotes a cyclopentyl or cyclohexyl group which is optionally substituted by 1 to 2 methyl groups and which is substituted by a carboxyalkoxy, alkoxycarbonylalkoxy, aminocarbonylalkoxy, alkylaminocarbonylalkoxy, dialkylaminocarbonylalkoxy, 1-pyrrolidinylcarbonylalkoxy, 1-piperidinylcarbonylalkoxy, morpholinocarbonylalkoxy, carboxyalkyl, alkoxycarbonylalkyl, aminocarbonylalkyl, alkylaminocarbonylalkyl, dialkylaminocarbonylalkyl, 1-pyrrolidinylcarbonylalkyl, 1-piperidinylcarbonylalkyl or morpholinocarbonylalkyl group, or R5 denotes a cyclohexylmethyl group, where the cyclohexyl moiety is substituted by a carboxyl, aminocarbonyl, alkylaminocarbonyl, dialkylaminocarbonyl, 1-pyrrolidinylcarbonyl, 1-piperidinylcarbonyl, morpholinocarbonyl, alkoxycarbonyl or hydroxymethyl group, or R5 denotes a 3- or 4-quinuclidinyl group, $R_d$ denotes a hydrogen atom or an alkyl group, $R_e$ represents a group of the formulae

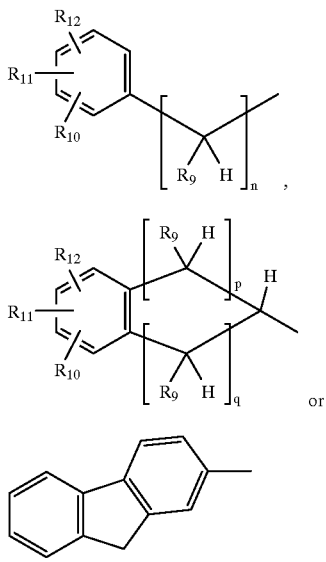

in which n represents the number 1, 2, 3 or 4, p represents the number 0, 1 or 2 q represents the number 0, 1 or 2, but where p and q must together result in at least the number 2, $R_9$ represents a hydrogen atom or a methyl group, it being possible for a plurality of $R_9$ radicals in a formula to be identical or different, $R_{10}$ represents a hydrogen, fluorine, chlorine, bromine or iodine atom, an alkyl, trifluoromethyl, ethynyl, alkoxy, cyclopropyl, trifluoromethoxy, cyano, alkoxycarbonyl or nitro group, $R_{11}$ represents a hydrogen, fluorine or chlorine atom, an amino, methyl or trifluoromethyl group and $R_{12}$ represents a hydrogen, chlorine or bromine atom, or $R_e$ denotes a 5-membered heteroaromatic ring which contains an imino group, an oxygen or sulphur atom or a nitrogen atom and an oxygen or sulphur atom or a nitrogen atom and an imino group or a sulphur atom and two nitrogen atoms, or a 6-membered heteroaromatic ring which contains 1, 2 or 3 nitrogen atoms, where the abovementioned 5- or 6-membered heteroaromatic rings can be substituted in the carbon framework by an alkyl group and, in addition, an n-butylene or 1,3-butadiene-1,4-diyl group can be attached both to the 5-membered and to the 6-membered abovementioned heteroaromatic rings via two adjacent carbon atoms, it additionally being possible for the abovementioned fused-on rings to be monosubstituted in the carbon framework by a fluorine, chlorine or bromine atom, by an alkyl, alkoxy, hydroxyl, phenyl, nitro, amino, alkylamino, dialkylamino, alkylcarbonylamino, cyano, carboxyl, alkoxycarbonyl, aminocarbonyl, alkylaminocarbonyl, dialkylaminocarbonyl, fluoromethyl, difluoromethyl, trifluoromethyl, alkylcarbonyl, aminosulphonyl, alkylaminosulphonyl or dialkylaminosulphonyl group or disubstituted by fluorine or chlorine atoms, by methyl, methoxy or hydroxyl groups, and it being possible for the abovementioned fused heterocyclic systems to be bonded both via a carbon atom or via an imino group of the heterocyclic moiety and via a carbon atom of the alicyclic aromatic moiety to the nitrogen atom of the $R_dNR_e$ group, $R_g$ denotes a 1-azetidinyl group which is optionally substituted by an alkyl group and in which the two hydrogen atoms of a methylene group are replaced by a straight-chain $C_{4-6}$-alkylene bridge, with in each case a methylene group in the $C_{4-6}$-alkylene bridge being replaced by an $R_{13}N$ group, where $R_{13}$ represents a hydrogen atom, an alkyl, hydroxy-$C_{2-4}$-alkyl, alkoxy-$C_{2-4}$-alkyl, amino-$C_{2-4}$-alkyl, alkylamino-$C_{2-4}$-alkyl, dialkylamino-$C_{2-4}$-alkyl, aminocarbonylalkyl, alkylaminocarbonylalkyl, dialkylaminocarbonylalkyl, aryl, aralkyl, formyl, alkylcarbonyl, alkylsulphonyl, arylcarbonyl, arylsulphonyl, aralkylcarbonyl, aralkylsulphonyl, alkoxycarbonyl, cyano, aminocarbonyl, alkylaminocarbonyl or dialkylaminocarbonyl group or an (alkyleneimino)carbonyl group with, in each case, 4 to 7 ring atoms in the alkyleneimino moiety, it being possible for a methylene group in position 4 in a 6- to 7-membered alkyleneimino moiety to be replaced by an oxygen or sulphur atom, by a sulphinyl, sulphonyl, imino or N-alkylimino group, or the bicyclic ring formed in this way is substituted by the radical $R_{14}$, where $R_{14}$ represents a hydroxyl, alkoxy, amino, alkylamino, dialkylamino, cyano, alkylcarbonylamino, alkylsulphonylamino, alkoxycarbonylamino, arylcarbonyl, carboxyl, alkoxycarbonyl, aminocarbonyl, alkylaminocarbonyl or dialkylaminocarbonyl group, or $R_g$ denotes a 1-pyrrolidinyl, 1-piperidinyl or 1-azacyclohept-1-yl group which is optionally substituted by 1 to 2 alkyl groups and in which the two hydrogen atoms of a methylene group are replaced by a straight-chain $C_{3-6}$-alkylene bridge where, in each case, a methylene group in the $C_{3-6}$-alkylene bridge is replaced by an $R_{13}N$ group where $R_{13}$ is defined as mentioned above in this claim, or the bicyclic ring formed in this way is substituted by the radical $R_{14}$ where $R_{14}$ is defined as mentioned above in this claim, or $R_g$ denotes a 5- to 7-membered alkyleneimino group (or, if such group has 6 or 7 members, an analog thereof having in the 4 position, instead of a methylene group, an oxygen or sulphur atom or by an imino or N-alkylimino group) which is optionally substituted by 1 to 2 alkyl groups and which is linked via a carbon atom to a carbon atom of a 5- to 7-membered alkyleneimino group (or, if such group has 6 or 7 members, an analog thereof having in the 4 position, instead of a methylene group, an oxygen or sulphur atom or by an imino or N-alkylimino group) in which the nitrogen atom is substituted by an alkylcarbonyl, arylcarbonyl, alkylsulphonyl, alkoxycarbonyl, aminocarbonyl, alkylaminocarbonyl, dialkylaminocarbonyl or (alkyleneimino)carbonyl group with 5 to 7 ring atoms in the alkyleneimino moiety (or, if such alkyleneimino moiety has 6 or 7 members, an analog thereof having in the 4 position, instead of a methylene group, an oxygen or sulphur atom or an imino or N-alkylimino group), a 5- to 7-membered alkyleneimino group which is optionally substituted by 1 to 2 alkyl groups and is substituted by a 3-oxo-1-piperazinylcarbonyl group which is optionally substituted in position 4 by an alkyl group, a 5- to 7-membered alkyleneimino group which is substituted by a pyridyl group and optionally in addition by 1 to 2 alkyl groups, an $(R_8NR_7)$—CO—$NR_6$ group where $R_6$ to $R_8$ are defined as mentioned above in this claim, a 3-oxo-1-piperazinyl group which is optionally substituted in position 1 by an alkyl group and optionally in addition by 1 to 2 alkyl groups, a 1-imidazolyl group which is optionally substituted by 1 to 2 alkyl groups, a 1-piperazinyl or 1-homopiperazinyl group which is optionally substituted by 1 to 2 alkyl groups and is in each case substituted in position 4 by an (alkyleneimino)carbonylalkyl group with, in each case, 5 to 7 ring atoms in the alkyleneimino moiety, it being possible for a methylene group in position 4 in a 6- to 7-membered alkyleneimino moiety to be replaced by an oxygen or sulphur atom or by an imino, N-alkylimino, N-arylimino, N-aralkylimino, N-formylimino, N-alkylcarbonylimino, N-alkylsulphonylimino, N-arylcarbonylimino, N-arylsulphonylimino, N-aralkylcarbonylimino, N-alkoxycarbonylimino, N-cyanoimino, N-aminocarbonylimino, N-alkylaminocarbonylimino or N-dialkylaminocarbonylimino group, a 1-piperazinyl group which is optionally substituted by 1 to 2 alkyl groups and is substituted in position 4 by a pyridyl group, a 1-piperazinyl or 1-homopiperazinyl group which is optionally substituted by 1 to 2 alkyl groups and is in each case substituted on the 4-nitrogen atom by a $B_1$, $B_2$, $B_1$-alkyl, $B_2$-alkyl, $B_3$-alkyl, $B_4$-alkyl, $B_1$-carbonyl, $B_2$-carbonyl, $B_4$-carbonyl, $B_1$-aminocarbonyl, $B_2$-aminocarbonyl, N-($B_1$)-N-alkylaminocarbonyl, N-($B_2$)-N-alkylaminocarbonyl group in which $B_1$ represents a 5–7-membered cyclic group consisting of 4–6 methylenes and an oxygen or sulphur atom, a sulphinyl, sulphonyl, imino, N-alkylimino, N-arylimino, N-alkylcarbonylimino, N-alkylsulphonylimino, N-arylcarbonylimino, N-formylimino, N-alkoxycarbonylimino or N-cyanoimino group, $B_2$ represents a $C_{5-7}$-cycloalkyl group which is substituted by the radical $R_{14}$ where $R_{14}$ is defined as mentioned above in this claim, $B_3$ is a group of the formula

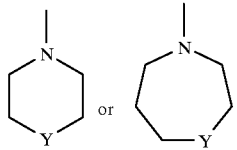

in which Y is an oxygen or sulphur atom, a sulphinyl, sulphonyl, imino, N-alkylimino, N-arylimino, N-alkylcarbonylimino, N-alkylsulphonylimino, N-arylcarbonylimino, N-formylimino, N-alkoxycarbonylimino or N-cyanoimino group, and $B_4$ represents a 5–7-membered 1-alkyleneimino group which is substituted by the radical $R_{14}$ where $R_{14}$ is defined as mentioned above in this claim, or $R_g$ denotes a 1-pyrrolidinyl group which is optionally substituted by 1 to 2 alkyl groups and is substituted in position 3 by a $B_1$-alkyl, $B_2$-alkyl, $B_4$-alkyl, $B_1$-oxy, $B_2$-oxy, $B_1$-amino, $B_2$-amino, N-($B_1$)-N-alkylamino, N-($B_2$)-N-alkylamino, $B_4$-carbonyl, $B_1$-aminocarbonyl, $B_2$-aminocarbonyl, N-($B_1$)-N-alkylaminocarbonyl, N-($B_2$)-N-alkylaminocarbonyl, $B_1$-carbonylamino, $B_2$-carbonylamino, $B_3$-carbonylamino, $B_4$-carbonylamino, N-($B_1$-carbonyl)-N-alkylamino, N-($B_2$-carbonyl)-N-alkylamino, N-($B_3$-carbonyl)-N-alkylamino, N-($B_4$-carbonyl)-N-alkylamino, $B_2$-aminoalkyl, N-($B_2$)-N-alkylaminoalkyl group, where $B_1$ to $B_4$ are defined as mentioned above in this claim, a 1-piperidinyl or 1-azacycloheptyl group which is optionally substituted by 1 to 2 alkyl groups and is substituted in position 3 or 4 by a $B_1$-alkyl, $B_2$-alkyl, $B_4$-alkyl, $B_1$-oxy, $B_2$-oxy, $B_1$-amino, $B_2$-amino, N-($B_1$)-N-alkylamino, N-($B_2$)-N-alkylamino, $B_4$-carbonyl, $B_1$-aminocarbonyl, $B_2$-aminocarbonyl, N-($B_1$)-N-alkylaminocarbonyl, N-($B_2$)-N-alkylaminocarbonyl, $B_1$-carbonylamino, $B_2$-carbonylamino, $B_3$-carbonylamino, $B_4$-carbonylamino, N-($B_1$-carbonyl)-N-alkylamino, N-($B_2$-carbonyl)-N-alkylamino, N-($B_3$-carbonyl)-N-alkylamino, N-($B_4$-carbonyl)-N-alkylamino, $B_2$-aminoalkyl, N-($B_2$)-N-alkylaminoalkyl group, where $B_1$ to $B_4$ are defined as mentioned above in this claim, an ($R_{15}NR_{16}$) group in which $R_{15}$ denotes a hydrogen atom or an alkyl group, $R_{16}$ denotes a 3-pyrrolidinyl, 3- or 4-piperidinyl or 3- or 4-azacycloheptyl group which is optionally substituted by 1 to 2 alkyl groups and is substituted in position 1 by a $B_1$, $B_2$, $B_1$-alkyl, $B_2$-alkyl, $B_3$-alkyl, $B_4$-alkyl, $B_1$-carbonyl, $B_2$-carbonyl, $B_4$-carbonyl, $B_1$-aminocarbonyl, $B_2$-aminocarbonyl, N-($B_1$)-N-alkylaminocarbonyl, N-($B_2$)-N-alkylaminocarbonyl group, where $B_1$ to $B_4$ are defined as mentioned above in this claim, a $C_{5-7}$-cycloalkyl group which is optionally substituted by 1 to 2 methyl groups and is substituted by a $B_1$-alkyl, $B_2$-alkyl, $B_4$-alkyl, $B_1$-oxy, $B_2$-oxy, $B_1$-amino, $B_2$-amino, N-($B_1$)-N-alkylamino, N-($B_2$)-N-alkylamino, $B_4$-carbonyl, $B_1$-aminocarbonyl, $B_2$-aminocarbonyl, N-($B_1$)-N-alkylaminocarbonyl, N-($B_2$)-N-alkylaminocarbonyl, $B_1$-carbonylamino, $B_2$-carbonylamino, $B_3$-carbonylamino, $B_4$-carbonylamino, N-($B_1$-carbonyl)-N-alkylamino, N-($B_2$-carbonyl)-N-alkylamino, N-($B_3$-carbonyl)-N-alkylamino, N-($B_4$-carbonyl)-N-alkyl amino, $B_2$-aminoalkyl, N-($B_2$)-N-alkyl-aminoalkyl group, where $B_1$ to $B_4$ are defined as mentioned above in this claim, a $C_{2-4}$-alkyl group which is substituted by a bicyclic group of the formula

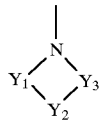

wherein two of the moieties $Y_1$, $Y_2$ and $Y_3$ are methylene groups (one of which is optionally substituted with an alkyl group) and one of moieties $Y_1$, $Y_2$ and $Y_3$ is a carbon atom substituted with a straight-chain, 4–6-membered bridge comprising 3–5 methylene groups and one group of the formula $R_{13}N$, wherein $R_{13}$ is defined as mentioned above in this claim or wherein one of the moieties $Y_1$, $Y_2$ and $Y_3$ is a methylene group (optionally substituted with an alkyl group), another of the moieties $Y_1$, $Y_2$ and $Y_3$ is a carbon atom substituted with a straight chain, 4–6-membered bridge comprising 4–6 methylene groups, and the third of the moieties $Y_1$, $Y_2$ and $Y_3$ is a group of the formula $R_{13}N$, wherein $R_{13}$ is defined as mentioned above in this claim, the bicyclic group formed in this way is substituted by the radical $R_{14}$ where $R_{14}$ is defined as mentioned above in this claim, a $C_{2-4}$-alkyl group which is substituted by a bicylcic group of the formula

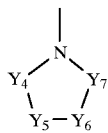

wherein three of the moieties $Y_4$–$Y_7$ are methylene groups (optionally substituted with 1 to 2 alkyl groups) one of moieties $Y_4$–$Y_7$ is a carbon atom substituted with a straight-chain, 3–6-membered bridge comprising 2–5 methylene groups and one group of the formula $R_{13}N$, wherein $R_{13}$ is defined as mentioned above in this claim, or wherein two of the moieties $Y_4$–$Y_7$ are methylene groups (both optionally substituted with an alkyl group), another of the moieties $Y_1$–$Y_7$ is a carbon atom substituted with a straight chain, 3–6-membered bridge comprising 3–6 methylene groups, and the fourth of the moieties $Y_4$–$Y_7$ is a group of the formula $R_{13}N$, wherein $R_{13}$ is defined as mentioned above in this claim, or a bicyclic group of the formula

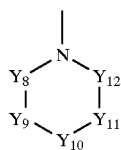

wherein four of the moieties $Y_8$–$Y_{12}$ are methylene groups (optionally substituted with 1 to 2 alkyl groups) and one of moieties $Y_8$–$Y_{12}$ is a carbon atom substituted with a straight-chain, 3–6-membered bridge comprising 2–5 methylene groups and one group of the formula $R_{13}N$, wherein $R_{13}$ is defined as mentioned above in this claim, or wherein three of the moieties $Y_8$–$Y_{12}$ are methylene groups (two of which are optionally substituted with an alkyl group), another of the moieties $Y_8$–$Y_{12}$ is a carbon atom substituted with a straight-chain, 3–6-membered bridge comprising 3–6 methylene groups, and the fifth of the moieties $Y_8$–$Y_{12}$ is a group of the formula $R_{13}N$, wherein $R_{13}$ is defined as mentioned above in this claim, or a bicyclic group of the formula

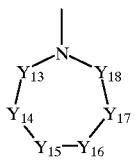

wherein five of the moieties $Y_{13}$–$Y_{18}$ are methylene groups (optionally substituted with 1 to 2 alkyl groups) and one of moieties $Y_{13}$–$Y_{18}$ is a carbon atom substituted with a straight-chain, 3–6-membered bridge comprising 2–5 methylene groups and one group of the formula $R_{13}N$, wherein $R_{13}$ is defined as mentioned above in this claim, or wherein four of the moieties $Y_{13}$–$Y_{18}$ are methylene groups (two of which are optionally substituted with an alkyl group), another of the moieties $Y_{13}$–$Y_{18}$ is a carbon atom substituted with a straight-chain, 3–6-membered bridge comprising 3–6 methylene groups, and the sixth of the moieties $Y_{12}$–$Y_{18}$ is a group of the formula $R_{13}N$, wherein $R_{13}$ is defined as mentioned above in this claim, or the bicyclic groups formed in this way are substituted by the radical $R_{14}$ where $R_{14}$ is defined as mentioned above in this claim, an alkylamino group whose alkyl moiety can optionally be substituted by a hydroxyl group, a 1-piperidinyl group whose 4-methylene group is replaced by an oxygen atom or by an imino or N-alkylimino group, an alkyl group which is substituted by a pyridyl group or a phenyl group which is substituted by an aminomethyl group, a $C_{2-4}$-alkyl group which is substituted by a 5- to 7-membered 1-alkyleneimino group which is substituted by the radical $R_{14}$, a 1-piperazinylcarbonylalkyl group which is substituted in position 4 of the piperazinyl moiety by a formyl or alkoxycarbonyl group, an alkylcarbonyl, alkoxycarbonyl or arylcarbonyl group, an (alkyleneimino)carbonyl group with, in each case, 5 to 7 ring atoms in the alkyleneimino moiety, or an analog thereof having 6 or 7 ring atoms and wherein there is, in position 4, instead of a methylene group, an oxygen or sulphur atom, a sulphinyl, sulphonyl, imino, N-alkylimino, N-alkylcarbonylimino, N-formylimino, N-alkoxycarbonylimino, N-alkylsulphonylimino, N-arylimino or N-aralkylimino group, a 3-pyrrolidinyl, 3- or 4-piperidinyl or 3- or 4-azacycloheptyl group which is substituted in position 1 by a trifluoroacetyl group, a $C_{5-7}$-cycloalkyl group which is optionally substituted by 1 to 2 methyl groups and is substituted by an alkoxycarbonylaminoalkyl, N-(alkoxycarbonyl)-N-alkylaminoalkyl, (2-hydroxyethyl)aminocarbonyl, (2-alkoxyethyl)aminocarbonyl, (2-aminoethyl)aminocarbonyl, carboxyalkylamino or alkoxycarbonylalkylamino group, a $C_{5-7}$-cycloalkyl group which is optionally substituted by 1 to 2 methyl groups and in which one methylene group is replaced by an imino, N-alkylimino, N-arylimino, N-alkylcarbonylimino, N-alkylsulphonylimino, N-arylcarbonylimino or N-alkoxycarbonylimino group, and where in each case two hydrogen atoms in the cycloalkyl moiety are replaced by a straight-chain alkylene bridge, where this bridge contains 2 to 6 carbon atoms when the two hydrogen atoms are located on the same carbon atom, or contains 1 to 5 carbon atoms when the two hydrogen atoms are located on adjacent carbon atoms, or contains 2 to 4 carbon atoms when the two hydrogen atoms are located on carbon atoms separated by one atom, a phenyl group which is substituted by an (alkyleneimino)carbonyl group with, in each case, 5 to 7 ring atoms in the alkyleneimino moiety, or an analog thereof having 6 or 7 ring atoms and wherein there is, in position 4, instead of a methylene group, an oxygen or sulphur atom, a sulphinyl, sulphonyl, imino, N-alkylimino, N-alkylcarbonylimino, N-formylimino, N-alkoxycarbonylimino, N-alkylsulphonylimino, N-arylimino or N-aralkylimino group, a phenyl group which is substituted by a 3-oxo-1-piperazinyl group which is optionally substituted in position 1 by an alkyl group and optionally in addition substituted by 1 to 2 alkyl groups, where the abovementioned phenyl radicals can in each case be substituted by a fluorine, chlorine or bromine atom, by a nitro, alkyl, alkoxy, trifluoromethyl or hydroxyl group and, unless otherwise mentioned, the abovementioned alkyl, alkylene and alkoxy moieties each contain 1 to 4 carbon atoms, and, unless otherwise mentioned, each carbon atom in the abovementioned alkyleneimino, alkylene or cycloalkylene moieties which is bonded to a nitrogen, oxygen or sulphur atom cannot be bonded to another halogen, nitrogen, oxygen or sulphur atom, or a tautomer or pharmaceutically acceptable salt thereof.

2. A compound of the formula I, in accordance with claim 1, in which, with the proviso that at least (i) $A_2$ represents a methyl group,
(ii) $A_8$ represents a methyl group,
(iii) $A_4$ represents an $R_dNR_e$ group or
(iv) $A_6$ represents an $R_g$ group, $A_2$ and $A_8$, which can be identical or different, each denote a hydrogen atom or an alkyl group,
$A_4$ denotes an $R_aNR_b$ group or an $R_dNR_e$ group and
$A_6$ denotes an $R_c$ group or an $R_g$ group in which
  $R_a$ denotes a hydrogen atom,
  $R_b$ denotes a phenyl group which is substituted by the radicals $R_1$ to $R_3$ where
    $R_1$ denotes a hydrogen, fluorine, chlorine, bromine or iodine atom,
    an ethynyl, alkyl, hydroxyl or methoxy group,
    a phenyl, phenoxy, phenylalkyl, phenylalkoxy, nitro or cyano group,
    a methyl or methoxy group which is substituted by 1 to 3 fluorine atoms,
    an ethyl or ethoxy group which is substituted by 1 to 5 fluorine atoms,
    $R_2$ denotes a hydrogen, fluorine, chlorine or bromine atom, a methyl, trifluoromethyl, amino, methylamino, dimethylamino, acetylamino or methoxy group,
    $R_3$ denotes a hydrogen, fluorine, chlorine or bromine atom, and
  $R_c$ denotes a 1-pyrrolidinyl group which can be substituted by 1 to 2 methyl groups, by one carboxyl, hydroxyalkyl, aminoalkyl, alkylaminoalkyl, dialkylaminoalkyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group,
  a 1-piperidinyl group which can be substituted by 1 to 2 methyl groups, by one hydroxyalkyl, aminoalkyl, alkylaminoalkyl, dialkylaminoalkyl, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group or in position 3 or 4 also by a hydroxyl, alkoxy, amino, alkylamino, dialkylamino, alkylcarbonylamino, alkoxycarbonylamino, formylamino, cyanoamino, alkylsulphonylamino, dialkylaminocarbonylamino, N-alkyl-dialkylaminocarbonylamino or cyano group,
  a group of the formula

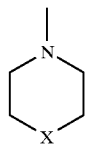

which is optionally substituted by 1 or 2 alkyl groups and wherein X is an oxygen or sulphur atom, a carbonyl, sulphinyl, sulphonyl, imino, alkylimino, amino-$C_{2-4}$-alkylimino, alkylamino-$C_{2-4}$alkylimino, dialkylamino-$C_{2-4}$-alkylimino, alkylcarbonylimino or alkylsulphonylimino group, a 1-azacyclohept-1-yl group, or an analog thereof having in position 4, instead of a methylene group, an oxygen atom, an imino, N-alkylimino, N-alkylcarbonylimino or N-alkylsulphonylimino group, wherein said 1-azacyclohept-1-yl group or analog thereof is optionally substituted by 1 or 2 methyl groups, or a 5- to 7-membered alkyleneimino group which is optionally substituted by 1 or 2 methyl groups and is linked via a carbon atom to a carbon atom of a 5- to 7-membered alkyleneimino group in which the nitrogen atom can be substituted by a methyl group, an ($R_4NR_5$) group, in which
  $R_4$ denotes a hydrogen atom or an alkyl group and
  $R_5$ denotes a hydrogen atom, a $C_{1-6}$-alkyl group which can be substituted by a hydroxyl, alkoxy, cyano, carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl, 4-alkyl-1-piperazinylcarbonyl, amino, formylamino, alkylamino, dialkylamino, alkylcarbonylamino, N-alkyl-alkylcarbonylamino, alkoxycarbonylamino, N-alkyl-alkoxycarbonylamino, alkylsulphonylamino, N-alkylalkylsulphonylamino, 1-pyrrolidinyl, 2-oxo-1-pyrrolidinyl, 1-piperidinyl, 2-oxo-1-piperidinyl, morpholino, 1-piperazinyl, 4-alkyl-1-piperazinyl, 4-alkylcarbonyl-1-piperazinyl, 4-alkylsulphonyl-1-piperazinyl, 4-alkoxycarbonyl-1-piperazinyl, 4-cyano-1-piperazinyl, 4-formyl-1-piperazinyl, 4-aminocarbonyl-1-piperazinyl, 4-alkylaminocarbonyl-1-piperazinyl or 4-dialkylaminocarbonyl-1-piperazinyl or an ($R_8NR_7$)—CO—$NR_6$ group where
  $R_6$, $R_7$ and $R_8$, which can be identical or different, each represent a hydrogen atom or an alkyl group or
  $R_6$ and $R_7$ together represent an n-$C_{2-4}$-alkylene group and
  $R_8$ represents a hydrogen atom or an alkyl group, a $C_{3-6}$-alkyl group which is substituted by 2 to 5 hydroxyl groups, a phenyl group which is substituted in position 4 by an alkylcarbonylamino, N-alkylalkylcarbonylamino or by an ($R_6NR_7$)—CO—$NR_6$— group where $R_6$ to $R_8$ are defined as mentioned above in this claim, a phenyl group which is substituted in position 4 by a 1-pyrrolidinyl, 1-piperidinyl, 2-oxo-1-pyrrolidinyl, 2-oxo-1-piperidinyl, morpholino, 1-piperazinyl or 4-alkyl-1-piperazinyl group, a $C_{3-7}$-cycloalkyl group which can be substituted by a carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, a $C_{5-7}$-cycloalkyl group which is optionally substituted by 1 or 2 methyl groups and is substituted by one hydroxymethyl, cyano, hydroxyl, alkoxy, amino, alkylamino, dialkylamino, alkoxycarbonylamino, N-alkyl-alkoxycarbonylamino, alkylcarbonylamino, N-alkyl-alkylcarbonylamino, alkylsulphonylamino, N-alkylalkylsulphonylamino or by an ($R_8NR_7$)—CO—$NR_6$— group where $R_6$ to $R_8$ are defined as mentioned above in this claim, a $C_{5-7}$-cycloalkyl group which is optionally substituted by 1 or 2 methyl groups and is substituted by a 1-pyrrolidinyl, 1-piperidinyl, 2-oxo- 1-pyrrolidinyl, 2-oxo-1-piperidinyl, morpholino, 1-piperazinyl, 4-alkyl-1-piperazinyl or 4-alkylcarbonyl-1-piperazinyl group, a tetrahydrofurfuryl group,
   a cyclopentyl group in which the methylene group in position 3 is replaced by an oxygen atom, an imino, alkylimino, alkylcarbonylimino, formylimino, aminocarbonylimino, alkylaminocarbonylimino, alkoxycarbonylimino, alkylsulphonylimino, dialkylaminocarbonylimino or cyanoimino group,
a cyclohexyl group in which the methylene group in position 3 is replaced by an imino, alkylimino, alkylcarbonylimino, alkoxycarbonylimino or alkylsulphonylimino group,
a cyclohexyl group in which the methylene group in position 4 is replaced by an oxygen atom, an imino, N-alkylimino, N-formylimino, N-alkylcarbonylimino, N-alkoxycarbonylimino, N-cyanoimino, N-aminocarbonylimino, N-alkylaminocarbonylimino, N,N-dialkylaminocarbonylimino or N-alkylsulphonylimino group,
a cyclohexyl group which is optionally substituted by 1 to 2 methyl groups and is substituted in position 4 by a carboxymethoxy, methoxycarbonylmethoxy, aminocarbonylmethoxy, alkylaminocarbonylmethoxy, dialkylaminocarbonylmethoxy, 1-pyrrolidinylcarbonylmethoxy, 1-piperidinylcarbonylmethoxy, morpholinocarbonylmethoxy, carboxyalkyl, alkoxycarbonylalkyl, aminocarbonylalkyl, alkylaminocarbonylalkyl, dialkylaminocarbonylalkyl, 1-pyrrolidinylcarbonylalkyl, 1-piperidinylcarbonylalkyl or morpholinocarbonylalkyl group,
a cyclohexylmethyl group where the cyclohexyl moiety is substituted by a carboxyl, aminocarbonyl, alkylaminocarbonyl, dialkylaminocarbonyl, 1-pyrrolidinylcarbonyl, 1-piperidinylcarbonyl, morpholinocarbonyl or alkoxycarbonyl group,
a 3- or 4-quinuclidinyl group,
$R_d$ denotes a hydrogen atom,
$R_e$ denotes a fluorenyl group,
a phenyl-$C_{1-4}$-alkyl, 1,2,3,4-tetrahydro-1-naphthyl or 1,2,3,4-tetrahydro-2-naphthyl group in which the aromatic moieties can each be monosubstituted by a fluorine, chlorine, bromine or iodine atom or an amino, alkyl, trifluoromethyl, ethynyl, methoxy, cyclopropyl, trifluoromethoxy, cyano, methoxycarbonyl or nitro group or disubstituted by fluorine, chlorine or bromine atoms,
an indolyl, indazolyl, quinolyl, isoquinolyl, 2,1,3-benzothiadiazolyl, thiazolyl, benzothiazolyl or pyridyl group which can be substituted in the carbon framework by an alkyl group and additionally by a fluorine, chlorine or bromine atom, by a methyl, methoxy, hydroxyl, phenyl, nitro, amino, alkylamino, dialkylamino, alkylcarbonylamino, cyano, carboxyl, alkoxycarbonyl, aminocarbonyl, alkylaminocarbonyl, dialkylaminocarbonyl, trifluoromethyl, alkylcarbonyl, aminosulphonyl, alkylaminosulphonyl or dialkylaminosulphonyl group and where the abovementioned heterocyclic systems are bonded via a carbon atom to the nitrogen atom of the $R_dNR_e$ group,
$R_g$ denotes a 1-azetidinyl group which is optionally substituted by a methyl group and in which the two hydrogen atoms of a methylene group are replaced by a straight-chain $C_{4-6}$-alkylene bridge, where in each case one methylene group in this $C_{4-6}$-alkylene bridge is replaced by an $R_{13}N$ group, where
   $R_{13}$ is a hydrogen atom or an alkyl, formyl, alkylcarbonyl, alkylsulphonyl, alkoxycarbonyl, cyano, aminocarbonyl, alkylaminocarbonyl or dialkylaminocarbonyl group,
or where this $C_{4-6}$-alkylene bridge is substituted by a hydroxyl, alkoxy, amino, alkylamino or dialkylamino group, $R_g$ denotes a 1-pyrrolidinyl, 1-piperidinyl or 1-azacyclohept-1-yl group which is optionally substituted by 1 to 2 methyl groups and in which the two hydrogen atoms of a methylene group are replaced by a straight-chain $C_{3-6}$-alkylene bridge, where in each case one methylene group in this $C_{3-6}$-alkylene bridge is replaced by an $R_{13}N$ group, where $R_{13}$ is defined as mentioned above in this claim, or this $C_{3-6}$-alkylene bridge is substituted by a hydroxyl, alkoxy, amino, alkylamino or dialkylamino group,
a 5- to 7-membered alkyleneimino group which is optionally substituted by 1 to 2 methyl groups and is linked via a carbon atom to a carbon atom of a 5- to 7-membered alkyleneimino group in which the nitrogen atom is substituted by an alkylcarbonyl, alkylsulphonyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group,
a 1-piperidinyl group which is linked in position 4 via a straight-chain $C_{2-4}$-alkylene bridge to a 4-piperidinyl or 1-methyl-4-piperidinyl group,
a 1-piperidinyl group which is optionally substituted by 1 to 2 methyl groups and is substituted by a 3-oxo-1-piperazinylcarbonyl group which is optionally substituted in position 4 by an alkyl group,
a 5- to 7-membered alkyleneimino group which is substituted by a pyridyl group and optionally in addition by 1 to 2 methyl groups,
a 3-oxo-1-piperazinyl group which is optionally substituted in position 1 by an alkyl group and optionally in addition by 1 to 2 methyl groups,
a 1-imidazolyl group which is optionally substituted by 1 to 2 methyl groups,
a 1-piperazinyl group which is optionally substituted by 1 to 2 methyl groups and is substituted in position 4 by a pyridyl group,
a 1-piperazinyl or 1-homopiperazinyl group which is optionally substituted by 1 to 2 methyl groups and is in each case substituted in position 4 by an (alkyleneimino)carbonylalkyl group with, in each case, 5 to 7 ring atoms in the alkyleneimino moiety, it being possible for a methylene group in position 4 in a 6- to 7-membered alkyleneimino moiety to be replaced by an oxygen atom or by an imino, N-alkylimino, N-formylimino, N-alkylcarbonylimino, N-alkylsulphonylimino, N-alkoxycarbonylimino, N-cyanoimino, N-aminocarbonylimino, N-alkylaminocarbonylimino or N-dialkylaminocarbonylimino group,
a 1-piperazinyl or 1-homopiperazinyl group which is optionally substituted by 1 to 2 methyl groups and is substituted in each case on the 4-nitrogen atom by a cyclopentyl group in which the 3-methylene group is replaced by an oxygen atom or an $R_{13}N$ group where $R_{13}$ is defined as mentioned above in this claim,
a 1-piperazinyl or 1-homopiperazinyl group which is optionally substituted by 1 to 2 methyl groups and is in each case substituted on the 4-nitrogen atom by a cyclohexyl group in which the 4-methylene group is replaced by an oxygen atom or an $R_{13}N$ group where $R_{13}$ is defined as mentioned above in this claim,
a 1-piperazinyl or 1-homopiperazinyl group which is optionally substituted by 1 to 2 methyl groups and is in each case substituted on the 4-nitrogen atom by a cyclohexyl group which is substituted in position 4 by the radical $R_{14}$ where
   $R_{14}$ represents a hydroxyl, alkoxy, amino, alkylamino, dialkylamino, alkylcarbonylamino, alkylsulphonylamino, alkoxycarbonylamino, carboxyl, alkoxycarbonyl, aminocarbonyl, alkylaminocarbonyl or dialkylaminocarbonyl group, a 1-pyrrolidinyl group which is optionally substituted by 1 to 2 methyl groups and is substituted in position 3 by a cyclohexylamino group whose 4-methylene group is replaced by an oxygen atom or an $R_{13}N$ group where $R_{13}$ is defined as mentioned above in this claim, or which is substituted in position 4 by the radical $R_{14}$ where $R_{14}$ is defined as mentioned above in this claim, a 1-pyrrolidinyl group which is optionally substituted by 1 to 2 methyl groups and is substituted in position 3 by a 1-piperidinylcarbonylamino group whose 4-methylene group is replaced by an oxygen atom or an $R_{13}N$ group where $R_{13}$ is defined as mentioned above in this claim, a 1-piperidinyl group which is optionally substituted by 1 to 2 methyl groups and is substituted in position 4 by a cyclohexylmethyl group whose 4-methylene group is replaced by an oxygen atom or an $R_{13}N$ group where $R_{13}$ is defined as mentioned above in this claim, or by a cyclohexylamino group whose 4-methylene group is replaced by an oxygen atom or an $R_{13}N$ group where $R_{13}$ is defined as mentioned above in this claim, or by a cyclohexylamino or cyclohexylaminomethyl group which is substituted in position 4 by the radical $R_{14}$ where $R_{14}$ is defined as mentioned above in this claim, a 1-piperidinyl group which is optionally substituted by 1 to 2 methyl groups and is substituted in position 4 by a 1-piperidinylcarbonylamino group whose 4-methylene group is replaced by an oxygen atom or an $R_{13}N$ group where $R_{13}$ is defined as mentioned above in this claim, a 1-piperidinyl group which is optionally substituted by 1 to 2 methyl groups and is substituted in position 4 by a 1-piperidinylmethyl or 1-piperidinylcarbonyl group which is substituted in position 4 by the radical $R_{14}$ where $R_{14}$ is defined as mentioned above in this claim, an $(R_{15}NR_{16})$ group in which $R_{15}$ denotes a hydrogen atom or an alkyl group, $R_{16}$ denotes a 3-pyrrolidinyl or 4-piperidinyl group which is optionally substituted by 1 to 2 methyl groups and is substituted in position 1 by a cyclopentyl group whose 3-methylene group is replaced by an oxygen atom or an $R_{13}N$ group or by a cyclohexyl group whose 4-methylene group is replaced by an oxygen atom or an $R_{13}N$ group, or which is substituted in position 4 by the radical $R_{14}$ where $R_{13}$ and $R_{14}$ are defined as mentioned above in this claim, a cyclopentyl group which is optionally substituted by 1 to 2 methyl groups and is substituted in position 3 by a 1-piperidinylcarbonylamino group whose 4-methylene group is replaced by an oxygen atom or an $R_{13}N$ group where $R_{13}$ is defined as mentioned above in this claim, a cyclohexyl group which is optionally substituted by 1 to 2 methyl groups and is substituted in position 3 or 4 by a 1-piperidinylcarbonylamino group whose 4-methylene group is replaced by an oxygen atom or an $R_{13}N$ group where $R_{13}$ is defined as mentioned above in this claim, a cyclohexyl group which is optionally substituted by 1 to 2 methyl groups and is substituted in position 4 by a cyclohexylmethyl, cyclohexylamino, cyclohexylaminocarbonyl or N-(cyclohexyl)-N-alkylaminocarbonyl group whose 4-methylene group is replaced by an oxygen atom or an $R_{13}N$ group where $R_{13}$ is defined as mentioned above in this claim, a cyclohexyl group which is optionally substituted by 1 to 2 methyl groups and is substituted in position 4 by a cyclohexylmethyl, cyclohexylamino or cyclohexylaminocarbonyl group which is substituted in position 4 by the radical $R_{14}$ where $R_{14}$ is defined as mentioned above in this claim, a cyclohexyl group which is optionally substituted by 1 to 2 methyl groups and is substituted in position 4 by a 1-piperidinylmethyl or 1-piperidinylcarbonyl group which is substituted in position 4 by the radical $R_{14}$ where $R_{14}$ is defined as mentioned above in this claim, a cyclohexyl group which is optionally substituted by 1 to 2 methyl groups and is substituted in position 4 by a cyclohexylaminomethyl group which is substituted in position 4 by the radical $R_{14}$ where $R_{14}$ is defined as mentioned above in this claim, an ethyl group which is substituted in position 2 by a 1-azetidinyl group which is optionally substituted by an alkyl group and in which two hydrogen atoms of a methylene group are replaced by a straight-chain $C_{4-6}$-alkylene bridge, where in each case a methylene group in this $C_{4-6}$-alkylene bridge is replaced by an $R_{13}N$ group where $R_{13}$ is defined as mentioned above in this claim, an ethyl group which is substituted in position 2 by a 1-pyrrolidinyl, 1-piperidinyl or 1-azacyclohept-1-yl group which is optionally substituted by 1 to 2 alkyl groups and in which two hydrogen atoms of a methylene group are replaced by a straight-chain $C_{3-6}$-alkylene bridge, where in each case a methylene group in this $C_{3-6}$-alkylene bridge is replaced by an $R_{13}N$ group where $R_{13}$ is defined as mentioned above in this claim, a 4-morpholinyl group, an alkyl group which is substituted by a pyridyl group or by a phenyl group which is substituted by an aminomethyl group, a $C_{2-4}$-alkyl group which is substituted by a 1-piperidinyl group which is substituted by the radical $R_{14}$, a 1-piperazinylcarbonylalkyl group which is substituted in position 4 of the piperazinyl moiety by a formyl or alkoxycarbonyl group, an alkylcarbonyl group, an (alkyleneimino)carbonyl group with, in each case, 5 to 7 ring atoms in the alkyleneimino moiety, it being possible for the methylene group in position 4 in each of the abovementioned 1-piperidinyl moieties to be replaced by an oxygen atom or by an imino or N-alkylimino group, a 3-pyrrolidinyl, 3- or 4-piperidinyl or 3- or 4-azacycloheptyl group which is substituted in position 1 by a trifluoroacetyl group, a cyclohexyl group which is optionally substituted by 1 to 2 methyl groups and is substituted by a $C_{1-4}$-alkoxycarbonylaminoalkyl,, N-($C_1$ 4-alkoxycarbonyl)-N-alkylaminoalkyl, (2-hydroxyethyl)aminocarbonyl, (2-alkoxyethyl)aminocarbonyl, (2-aminoethyl)aminocarbonyl, carboxy-$C_{1-4}$-alkylamino or alkoxycarbonyl-$C_{1-4}$-alkylamino group, a cyclohexyl group which is optionally substituted by 1 to 2 methyl groups and in which one methylene group is replaced by an imino, N-alkylimino, N-arylimino, N-alkylcarbonylimino, N-alkylsulphonylimino, N-arylcarbonylimino or N-alkoxycarbonylimino group and where in each case two hydrogen atoms in the cycloalkyl moiety are replaced by a straight-chain alkylene bridge, where this bridge contains 2 to 4 carbon atoms and the two hydrogen atoms are located on carbon atoms separated by one atom, a phenyl group which is substituted by an (alkyleneimino) carbonyl group with in each case 5 to 7 ring atoms in the alkyleneimino moiety, it being possible for the methylene group in position 4 of each of the abovementioned 1-piperidinyl moieties to be replaced by an oxygen atom or by an imino or N-alkylimino group, a phenyl group which is substituted in position 4 by a 3-oxo-1-piperazinyl group which is optionally substituted in position 4 by a methyl group and optionally additionally by 1 to 2 methyl groups, their tautomers, their stereoisomers and their salts, where, unless otherwise mentioned, the abovementioned alkyl, alkylene and alkoxy moieties each contain 1 to 2 carbon atoms, and, unless otherwise mentioned, each carbon atom in the abovementioned alkylene or cycloalkylene moieties which is bonded to a nitrogen, oxygen or sulphur atom cannot be bonded to another halogen, nitrogen, oxygen or sulphur atom, or a tautomer or pharmaceutically acceptable salt thereof.

3. A compound of the formula I, in accordance with claim 1, in which, with the proviso that at least (i) $A_2$ represents a methyl group, (ii) $A_8$ represents a methyl group, (iii) $A_4$ represents an $R_dNR_e$ group or (iv) $A_6$ represents an $R_g$ group, those in which $A_2$ and $A_8$, which can be identical or different, each denote a hydrogen atom or an alkyl group, $A_4$ denotes an $R_aNR_b$ group or an $R_dNR_e$ group and $A_6$ denotes an $R_c$ group or an $R_g$ group in which $R_a$ denotes a hydrogen atom, $R_b$ denotes a phenyl group substituted by the radicals $R_1$ to $R_3$, where $R_1$ denotes a hydrogen, fluorine, chlorine, bromine or iodine atom, an ethynyl, alkyl, phenoxy or methoxy group, a nitro or cyano group, a methyl or methoxy group which is substituted by 1 to 3 fluorine atoms, $R_2$ denotes a hydrogen, fluorine, chlorine or bromine atom or an amino group, $R_3$ denotes a hydrogen, fluorine, chlorine or bromine atom, and $R_c$ denotes a 1-pyrrolidinyl group which can be substituted in position 3 by an aminomethyl, methylaminomethyl, dimethylaminomethyl, hydroxyl, methoxy, amino, methylamino, dimethylamino, methylcarbonylamino, methoxycarbonylamino, formylamino, cyanoamino, methylsulphonylamino, dimethylaminocarbonylamino, N-methyl-dimethylaminocarbonylamino or cyano group, a 1-piperidinyl group which can be substituted in position 3 or 4 by an aminomethyl, methylaminomethyl, dimethylaminomethyl, carboxyl, methoxycarbonyl, aminocarbonyl, methylaminocarbonyl, dimethylaminocarbonyl, 1-pyrrolidinylcarbonyl, 1-piperidinylcarbonyl, morpholinocarbonyl, 1-piperazinylcarbonyl, 4-methyl-1-piperazinylcarbonyl, hydroxyl, methoxy, amino, methylamino, dimethylamino, alkylcarbonylamino, methoxycarbonylamino, formylamino, cyanoamino, methylsulphonylamino, dimethylaminocarbonylamino, N-methyl-dimethylaminocarbonylamino or cyano group, a 1-piperidinyl group in which the methylene group in position 4 is replaced by an oxygen or sulphur atom, by an imino, N-alkylimino, N-amino-$C_{2-4}$-alkylimino, alkylamino-$C_{2-4}$-alkyl-imino, dialkylamino-$C_{2-4}$-alkylimino, alkylcarbonylimino or alkylsulphonylimino group, a 1-piperidinyl group which is linked via a carbon atom to a carbon atom of a 5- to 7-membered alkyleneimino group in which the nitrogen atom can be substituted by a methyl group, an $(R_4NR_5)$ group in which $R_4$ denotes a hydrogen atom or an alkyl group, and $R_5$ denotes a hydrogen atom, a $C_{1-4}$-alkyl group, which can be substituted by a hydroxyl, methoxy, cyano, carboxyl, methoxycarbonyl, aminocarbonyl, methylaminocarbonyl, dimethylaminocarbonyl, 1-pyrrolidinylcarbonyl, 1-piperidinylcarbonyl, morpholinocarbonyl, 1-piperazinylcarbonyl, 4-methyl-1-piperazinylcarbonyl, amino, formylamino, methylamino, dimethylamino, acetylamino, methoxycarbonylamino, methylsulphonylamino, 1-pyrrolidinyl, 2-oxo-1-pyrrolidinyl, 1-piperidinyl, 2-oxo-1-piperidinyl, morpholino, 1-piperazinyl or 4-methyl-1-piperazinyl group, a phenyl group which is substituted in position 4 by an acetylamino or by an $(R_8NR_7)$—CO—$NR_6$ group where $R_6$ to $R_8$ are defined as mentioned above in this claim, a cyclopropyl group, a cyclohexyl group which is substituted by a carboxyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl, 4-alkyl-1-piperazinylcarbonyl, hydroxyl, alkoxy, amino, alkylamino, dialkylamino, alkoxycarbonylamino, alkylcarbonylamino, N-alkyl-alkylcarbonylamino, alkylsulphonylamino, 1-pyrrolidinyl, 1-piperidinyl, 2-oxo-1-pyrrolidinyl, 2-oxo-1-piperidinyl, morpholino, 1-piperazinyl, 4-methyl-1-piperazinyl or 4-acetyl-1-piperazinyl group, a cyclopentyl group in which the methylene group in position 3 is replaced by an imino or N-alkylimino group, a cyclohexyl group in which the methylene group in position 3 or 4 is replaced by an imino or N-alkylimino group, a 3-quinuclidinyl group, $R_d$ denotes a hydrogen atom,, $R_e$ denotes a fluorenyl group, a phenyl-$C_{1-2}$-alkyl or 1,2,3,4-tetrahydro-2-naphthyl group in which the aromatic moieties can each be monosubstituted by a fluorine, chlorine, bromine or iodine atom or an amino, methyl, trifluoromethyl, methoxy, trifluoromethoxy, cyano, methoxycarbonyl or nitro group, an indolyl, indazolyl, quinolyl, isoquinolyl, 2,1,3-benzothiadiazolyl, thiazolyl, benzothiazolyl or pyridyl group which can be substituted in the carbon framework by a fluorine, chlorine or bromine atom, by a methyl, methoxy, hydroxyl, nitro, amino, methylamino, dimethylamino, cyano or trifluoromethyl group, and where the abovementioned heterocyclic systems are bonded via a carbon atom to the nitrogen atom of the $R_dNR_e$ group, $R_g$ denotes a 1-azetidinyl group which is optionally substituted by a methyl group and in which the two hydrogen atoms of the 3-methylene group are replaced by a straight-chain $C_{4-5}$-alkylene bridge, where, in each case, a methylene group in this $C_{4-5}$-alkylene bridge is replaced by an $R_{13}N$ group, where $R_{13}$ represents a hydrogen atom or an alkyl, acetyl or methoxycarbonyl group, or where this $C_{4-5}$-alkylene bridge is substituted by a hydroxyl or amino group, $R_g$ denotes a 1-pyrrolidinyl or 1-piperidinyl group which is optionally substituted by 1 to 2 methyl groups and in which the two hydrogen atoms of a methylene group are replaced by a straight-chain $C_{3-6}$-alkylene bridge, where, in each case, a methylene group in this $C_{3-6}$-alkylene bridge is replaced by an $R_{13}N$ group where $R_{13}$ is defined as mentioned above in this claim, or where this $C_{3-6}$-alkylene bridge is substituted by a hydroxyl or amino group, a 1-piperidinyl group which is linked via a carbon atom to a carbon atom of a piperidinyl group in which the nitrogen atom is substituted by an alkylcarbonyl, alkylsulphonyl, alkoxycarbonyl, aminocarbonyl, alkylaminocarbonyl, dialkylaminocarbonyl, 1-pyrrolidinylcarbonyl, 1-piperidinylcarbonyl, morpholinocarbonyl, 1-piperazinylcarbonyl or 4-alkyl-1-piperazinylcarbonyl group, a 1-piperidinyl group which is linked in position 4 via a straight-chain $C_{2-3}$-alkylene bridge to a 4-piperidinyl or 1-methyl-4-piperidinyl group, a 1-piperidinyl group which is substituted by a 3-oxo-1-piperazinylcarbonyl group which is optionally substituted in position 4 by an alkyl group, a 1-piperidinyl group which is substituted in position 4 by a pyridyl group a 3-oxo-1-piperazinyl group which is optionally substituted in position 1 by an alkyl group, a 1-imidazolyl group, a 1-piperazinyl group which is substituted in position 4 by a pyridyl group, a 1-piperazinyl or 1-homopiperazinyl group which is substituted in each case in position 4 by an (alkyleneimino) carbonylalkyl group with, in each case, 5 to 7 ring atoms in the alkyleneimino moiety, it being possible for a methylene group in position 4 of a 6- to 7-membered alkyleneimino moiety to be replaced by an oxygen atom or by an imino, N-alkylimino, N-alkylcarbonylimino or N-alkoxycarbonylimino group, a 1-piperazinyl or 1-homopiperazinyl group which is substituted in each case on the 4-nitrogen atom by a cyclopentyl group in which the 3-methylene group is replaced by an oxygen atom or an $R_{13}N$ group where $R_{13}$ is defined as mentioned above in this claim, a 1-piperazinyl or 1-homopiperazinyl group which is substituted in each case on the 4-nitrogen atom by a cyclohexyl group in which the 4-methylene group is replaced by an oxygen atom or an $R_{13}N$ group where $R_{13}$ is defined as mentioned above in this claim, a 1-piperazinyl or 1-homopiperazinyl group which is substituted in each case on the 4-nitrogen atom by a cyclohexyl group which is substituted in position 4 by the radical $R_{14}$, where $R_{14}$ represents a hydroxyl, alkoxy, amino, alkylamino, dialkylamino, alkylcarbonylamino, alkylsulphonylamino or alkoxycarbonylamino group, a 1-pyrrolidinyl group which is substituted in position 3 by a cyclohexylamino group whose 4-methylene group is replaced by an oxygen atom or an $R_{13}N$ group where $R_{13}$ is defined as mentioned above in this claim, or in position 4 by the radical $R_{14}$ where $R_{14}$ is defined as mentioned above in this claim, a 1-pyrrolidinyl group which is substituted in position 3 by a 1-piperidinylcarbonylamino group whose 4-methylene group is replaced by an oxygen atom or an $R_{13}N$ group where $R_{13}$ is defined as mentioned above in this claim, a 1-piperidinyl group which is substituted in position 4 by a cyclohexylmethyl group whose 4-methylene group is replaced by an oxygen atom or an $R_{13}N$ group, or by a cyclohexylamino group whose 4-methylene group is replaced by an oxygen atom or an $R_{13}N$ group, or by a cyclohexylamino or cyclohexylaminomethyl group which is substituted in position 4 by the radical $R_{14}$ where $R_{13}$ and $R_{14}$ are defined as mentioned above in this claim, a 1-piperidinyl group which is substituted in position 4 by a 1-piperidinylcarbonylamino group whose 4-methylene group is replaced by an oxygen atom or an $R_{13}N$ group where $R_{13}$ is defined as mentioned above in this claim, a 1-piperidinyl group which is substituted in position 4 by a 1-piperidinylmethyl or 1-piperidinylcarbonyl group which is substituted in position 4 by the radical $R_{14}$ where $R_{14}$ is defined as mentioned above in this claim, an $(R_{15}NR_{16})$ group in which $R_{15}$ denotes a hydrogen atom, $R_{16}$ denotes a 3-pyrrolidinyl or 4-piperidinyl group which is substituted in position 1 by a cyclopentyl group whose 3-methylene group is replaced by an oxygen atom or an $R_{13}N$ group, or by a cyclohexyl group whose 4-methylene group is replaced by an oxygen atom or an $R_{13}N$ group, or which is substituted in position 4 by the radical $R_{14}$, where $R_{13}$ and $R_{14}$ are defined as mentioned above in this claim, a cyclopentyl group which is substituted in position 3 by a 1-piperidinylcarbonylamino group whose 4-methylene group is replaced by an oxygen atom or an $R_{13}N$ group where $R_{13}$ is defined as mentioned above in this claim, a cyclohexyl group which is substituted in position 3 or 4 by a 1-piperidinylcarbonylamino group whose 4-methylene group is replaced by an oxygen atom or an $R_{13}N$ group where $R_{13}$ is defined as mentioned above in this claim, a cyclohexyl group which is substituted in position 4 by a cyclohexylmethyl, cyclohexylamino, cyclohexylaminocarbonyl or N-(cyclohexyl)-N-methylaminocarbonyl group whose 4-methylene group is replaced by an oxygen atom or an $R_{13}N$ group where $R_{13}$ is defined as mentioned above in this claim, a cyclohexyl group which is substituted in position 4 by a cyclohexylmethyl, cyclohexylamino or cyclohexylaminocarbonyl group which is substituted in position 4 by the radical $R_{14}$ where $R_{14}$ is defined as mentioned above in this claim, a cyclohexyl group which is substituted in position 4 by a 1-piperidinylmethyl or 1-piperidinylcarbonyl group which is substituted in position 4 by the radical $R_{14}$ where $R_{14}$ is defined as mentioned above in this claim, a cyclohexyl group which is substituted in position 4 by a cyclohexylaminomethyl group which is substituted in position 4 by the radical $R_{14}$ where $R_{14}$ is defined as mentioned above in this claim, an ethyl group which is substituted in position 2 by a 1-azetidinyl group in which two hydrogen atoms of a methylene group are replaced by a straight-chain $C_{4-6}$-alkylene bridge, where one methylene group in this $C_{4-6}$-alkylene bridge is replaced by an $R_{13}N$ group where $R_{13}$ is defined as mentioned above in this claim, an ethyl group which is substituted in position 2 by a 1-pyrrolidinyl or 1-piperidinyl group in which two hydrogen atoms of a methylene group are replaced by a straight-chain $C_{3-6}$-alkylene bridge, where in each case a methylene group in this $C_{3-6}$-alkylene bridge is replaced by an $R_{13}N$ group where $R_{13}$ is defined as mentioned above in this claim, a 4-morpholinyl group, an alkyl group which is substituted by a pyridyl group or by a phenyl group which is substituted by an aminomethyl group, an ethyl group which is substituted by a 1-piperidinyl group which is substituted by the radical $R_{14}$, a 1-piperazinylcarbonylalkyl group which is substituted in position 4 of the piperazinyl moiety by a formyl or methoxycarbonyl group, an alkylcarbonyl group, a 3-pyrrolidinyl or 3- or 4-piperidinyl group which is substituted in position 1 by a trifluoroacetyl group, or a cyclohexyl group which is substituted by a $C_{1-4}$-alkoxycarbonylaminoalkyl, (2-hydroxyethyl)

aminocarbonyl, (2-methoxyethyl)aminocarbonyl, carboxy-$C_{1-4}$-alkylamino or alkoxycarbonyl-$C_{1-4}$-alkylamino group,
a cyclohexyl group in which a methylene group is replaced by an imino, N-alkylimino, N-alkylcarbonylimino or N-alkoxycarbonylimino group and where two hydrogen atoms in positions 3 and 5 of the cycloalkyl moiety are replaced by an ethylene bridge,
a phenyl group which is substituted in position 4 by a 1-pyrrolidinylcarbonyl, 1-piperidinylcarbonyl or morpholinocarbonyl group,
a phenyl group which is substituted in position 4 by a 3-oxo-1-piperazinyl group which is optionally substituted in position 4 by a methyl group,
their tautomers, their stereoisomers and their salts,
where, unless otherwise mentioned, the abovementioned alkyl, alkylene and alkoxy moieties each contain 1 to 2 carbon atoms,
and, unless otherwise mentioned, each carbon atom in the abovementioned alkylene or cycloalkylene moieties which is bonded to a nitrogen, oxygen or sulphur atom cannot be bonded to another halogen, nitrogen, oxygen or sulphur atom,
or a tautomer or pharmaceutically acceptable salt thereof.

4. A compound of the formula I

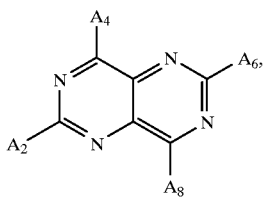

(I)

in which, with the proviso that at least
(i) $A_2$ represents a methyl group,
(ii) $A_8$ represents a methyl group,
(iii) $A_4$ represents an $R_dNR_e$ group or
(iv) $A_6$ represents an $R_g$ group,
those in which
$A_2$ and $A_8$, which can be identical or different, each denote a hydrogen atom or a methyl group,
$A_4$ denotes an $R_aNR_b$ group or an $R_dNR_e$ group and
$A_6$ denotes an $R_c$ group or an $R_g$ group in which
$R_a$ denotes a hydrogen atom
$R_b$ denotes a 3-methylphenyl, 4-amino-3,5-dibromophenyl, 4-phenoxyphenyl or 3-chloro-4-fluorophenyl group,
$R_c$ denotes a morpholino, cyclopropylamino, trans-(4-hydroxy-cyclohexyl)amino, 4-amino-1-piperidinyl, 4-(4-piperidinyl)-1-piperidinyl, 4-(1-methyl-4-piperidinyl)-1 -piperidinyl, 2-amino-2-methyl-1-propylamino, 4-piperidinylamino, 1-methyl-4-piperidinylamino, N-methyl-N-(1-methyl-4-piperidinyl)amino or trans-4-(morpholinocarbonyl)cyclohexylamino group,
$R_d$ denotes a hydrogen atom,
$R_e$ denotes a 5-indolyl, 5-quinolyl, 6-quinolyl, 8-quinolyl, 5-indazolyl, 6-indazolyl, 4-(2,1,3-benzothiadiazolyl), 2-thiazolyl, 2-methyl-5-benzothiazolyl, 2-pyridyl, 3-pyridyl, 4-pyridyl, 2-benzothiazolyl, 5-isoquinolyl, 6-isoquinolyl, 3-chlorobenzyl, 1,2,3,4-tetrahydro-2-naphthyl or 2-fluorenyl group,
$R_g$ denotes 7-methyl-2,7-diazaspiro[3.5]-1-nonyl, 1,8-diazaspiro[4.5]-8-decyl, 3,9-diazaspiro[5.5]-3-undecyl, 2,7-diazaspiro[3.5]-2-nonyl, 2,7-diazaspiro[3.5]-7-nonyl, 2-methyl-2,7-diazaspiro[4.4]-7-nonyl, 6-methyl-2,6-diazaspiro[3.4]-2-octyl or 2-methyl-2,6-diazaspiro[3.4]-6-octyl group,
a 1-imidazolyl, 3-oxo-1-piperazinyl or 4-methyl-3-oxo-1-piperazinyl group,
a 1-piperazinyl group which is substituted in position 4 by a 2-pyridyl, 4-pyridyl, 1-pyrrolidinylcarbonylmethyl, morpholinocarbonylmethyl, 4-piperidinyl, 1-methyl-4-piperidinyl, 1-acetyl-4-piperidinyl or 1-methoxycarbonyl-4-piperidinyl group,
a 3-(morpholinocarbonylamino)-1-pyrrolidinyl group,
a 1-piperidinyl group which is substituted in position 4 by a 1-acetyl-4-piperidinyl, 1-methoxycarbonyl-4-piperidinyl, 1-methylsulphonyl-4-piperidinyl, 1-(morpholinocarbonyl)-4-piperidinyl, 1-dimethylaminocarbonyl-4-piperidinyl, 3-oxo-1-piperazinylcarbonyl, 4-methyl-3-oxo-1-piperazinylcarbonyl, 4-pyridyl, trans-4-hydroxycyclohexylamino, 4-piperidinylamino, 4-piperidinylmethyl, morpholinocarbonylamino, (trans-4-hydroxycyclohexylamino)methyl, 4-amino-1-piperidinylmethyl, 4-methylamino-1-piperidinylmethyl, 4-dimethylamino-1-piperidinylmethyl or 4-ethylamino-1-piperidinylmethyl group,
a 1-piperidinyl group which is linked in position 4 via a straight-chain $C_{2-3}$-alkylene bridge to a 4-piperidinyl or 1-methyl-4-piperidinyl group,
a 1-piperidinyl group which is substituted in position 4 by a 1-methyl-4-piperidinylamino group,
a 1-(4-aminocyclohexyl)-4-piperidinylamino group,
a cyclopentylamino group which is substituted in position 3 by a morpholinocarbonylamino group,
a cyclohexylamino group which is substituted in position 3 by a morpholinocarbonylamino group,
a cyclohexylamino group which is substituted in position 4 by a 3-methoxycarbonyl-1-propylamino, trans-4-hydroxycyclohexylamino, 4-aminocyclohexylmethyl, morpholinocarbonylamino, (4-tetrahydropyranylamino)carbonyl, trans-4-hydroxycyclohexylaminocarbonyl, (4-amino-1-piperidinyl)carbonyl, (4-dimethylamino-1-piperidinyl)carbonyl, (4-piperidinylamino)carbonyl, N-(1-methyl-4-piperidinyl)-N-methylamino)carbonyl, (1-methyl-4-piperidinylamino)carbonyl, (4-dimethylamino-1-piperidinyl)-methyl, (4-amino-1-piperidinyl)methyl, tert-butyloxycarbonyl-aminomethyl, (4-hydroxycyclohexylamino)methyl, 3-carboxypropylamino, 2-hydroxyethylaminocarbonyl or 2-methoxyethylaminocarbonyl group,
a 4-piperidinylamino group which is substituted in position 1 by a 1-methyl-4-piperidinyl group,
a (4-morpholinyl)amino group,
a 2-(7-methyl-2,7-diazaspiro[4.4]-2-nonyl)ethylamino, 2-picolylamino, 4-picolylamino, 3-(aminomethyl)benzylamino or 4-(aminomethyl)benzylamino group,
a 2-(4-amino-1-piperidinyl)ethylamino, 4-formyl-1-piperazinylcarbonylmethylamino, 4-methoxycarbonyl-1-piperazinylcarbonylmethylamino, 1-(4-formyl-1-piperazinylcarbonyl)ethylamino or 1-(4-methoxycarbonyl-1-piperazinylcarbonyl)ethylamino group,
an acetylamino, 1-trifluoroacetyl-4-piperidinylamino or tropinylamino group,
a 9-amino-3-azaspiro[5.5]-3-undecyl or 8-amino-2-azaspiro[4.5]-2-decyl group,
a phenylamino group which is substituted in position 4 by a morpholinocarbonyl, 1-pyrrolidinylcarbonyl, 3-oxo-1-piperazinyl- or 4-methyl-3-oxo-1-piperazinyl group,
or a tautomer or pharmaceutically acceptable salt thereof.

5. A compound of the formula I

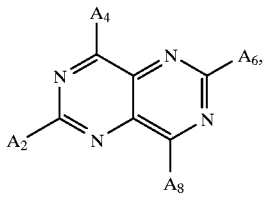
(I)

in which, with the proviso that at least
(i) $A_2$ represents a methyl group,
(ii) $A_8$ represents a methyl group,
(iii) $A_4$ represents an $R_aNR_e$ group or
(iv) $A_6$ represents an $R_g$ group,
$A_2$ and $A_8$, which can be identical or different, each denote a hydrogen atom or a methyl group,
$A_4$ denotes an $R_aNR_b$ group or an $R_dNR_e$ group and
$A_6$ denotes an $R_c$ group or an $R_g$ group, in which
$R_a$ denotes a hydrogen atom
$R_b$ denotes a 3-methylphenyl, 4-amino-3,5-dibromophenyl, 4-phenoxyphenyl or 3-chloro-4-fluorophenyl group,
$R_c$ denotes a morpholino, cyclopropylamino, trans-(4-hydroxy-cyclohexyl)amino or 4-amino-1-piperidinyl group,
$R_d$ denotes a hydrogen atom,
$R_e$ denotes a 5-indolyl, 5-quinolyl, 6-quinolyl, 8-quinolyl, 5-indazolyl, 6-indazolyl, 4-(2,1,3-benzothiadiazolyl), 2-thiazolyl, 2-methyl-5-benzothiazolyl, 2-pyridyl, 3-pyridyl, 4-pyridyl, 2-benzothiazolyl, 5-isoquinolyl, 6-isoquinolyl, 3-chlorobenzyl, 1,2,3,4-tetrahydro-2-naphthyl or 2-fluorenyl group,
$R_g$ denotes a 7-methyl-2,7-diazaspiro[3,5]-1-nonyl, 2-methyl-2,7-diazaspiro[4.4]-7-nonyl, 6-methyl-2,6-diazaspiro[3.4]-2-octyl or 2-methyl-2,6-diazaspiro[3.4]-6-octyl group,
a 4-(2-pyridyl)-1-piperazinyl, 4-(4-pyridyl)-1-piperazinyl, 3-oxo-1-piperazinyl, 1-imidazolyl, 4-(1-pyrrolidinylcarbonylmethyl)-1-piperazinyl, 4-(morpholinocarbonylmethyl)-1-piperazinyl, 4-(trans-4-hydroxycyclohexylamino)cyclohexylamino, 4-(4-aminocyclohexylmethyl)cyclohexylamino, 2-(7-methyl-2,7-diazaspiro[4.4]-2-nonyl)ethylamino, (4-morpholinyl)amino, 2-picolylamino, 4-picolylamino, 3-(aminomethyl)benzylamino, 4-(aminomethyl)benzylamino, acetylamino, 1-trifluoroacetyl-4-piperidinylamino or tropinylamino group,
a 1-pyrrolidinyl group which is substituted in position 3 by a morpholinocarbonylamino group,
a 4-piperidinylamino group which is substituted in position 1 by a 1-methyl-4-piperidinyl group,
a 1-piperidinyl group which is substituted in position 4 by a 4-pyridyl, morpholinocarbonylamino, 1-methyl-4-piperidinylamino, 4-piperidinylamino, 1-acetyl-4-piperidinyl or 1-methoxycarbonyl-4-piperidinyl group,
a 1-piperidinyl group which is linked in position 4 via a straight-chain $C_{2-3}$-alkylene bridge to a 4-piperidinyl or 1-methyl-4-piperidinyl group,
a cyclohexylamino group which is substituted in position 4 by a 2-methoxyethylaminocarbonyl, (4-tetrahydropyranylamino)carbonyl, trans-4-hydroxycyclohexylaminocarbonyl, tert-butyloxycarbonylaminomethyl or 3-methoxycarbonyl-1-propylamino group,
or a 1-piperazinyl group which is substituted in position 4 by a 4-piperidinyl, 1-methyl-4-piperidinyl or 1-acetyl-4-piperidinyl group,
or a tautomer or pharmaceutically acceptable salt thereof.

6. A compound selected from the group consisting of:
(a) 4-(5-indolylamino)-6-morpholinopyrimido[5,4-d]pyrimidine,
(b) 4-(5-indolylamino)-6-[trans-(4-hydroxycyclohexyl)amino]pyrimido[5,4-d]pyrimidine,
(c) 4-[(3-chloro-4-fluorophenyl)amino]-6-[4-(morpholinocarbonylmethyl)-1-piperazinyl]pyrimido[5,4-d]pyrimidine,
(d) 4-[(3-chloro-4-fluorophenyl)amino]-6-[(4-morpholinyl)amino]pyrimido[5,4-d]pyrimidine,
(e) 4-[(3-chloro-4-fluorophenyl)amino]-6-(4-picolylamino)pyrimido[5,4-d]pyrimidine,
(f) 4-[(3-chloro-4-fluorophenyl)amino]-6-[1-trifluoroacetyl-4-piperidinylamino]pyrimido[5,4-d]pyrimidine,
(g) 4-[(3-chloro-4-fluorophenyl)amino]-6-(endo-tropinylamino)pyrimido[5,4-d]pyrimidine,
(h) 4-[(3-chloro-4-fluorophenyl)amino]-6-(exo-tropinylamino)pyrimido[5,4-d]pyrimidine,
and the pharmaceutically acceptable salts thereof.

7. 4-[(3-Chloro-4-fluorophenyl)amino]-6-[2-methyl-2,7-diaza-spiro[4,4]-7-nonyl]-pyrimido [5,4-d]-pyrimidine.

8. 4-[(3-Chloro-4-fluorophenyl)amino]-6-[6-methyl-2,6-diaza-spiro[3,4]-2-octyl]-pyrimido[5,4-d]-pyrimidine.

9. 4-[(3-Chloro-4-fluorophenyl)-amino]-6-[4-(4-aminocyclohexylmethyl)cyclohexylamino]-pyrimido[5,4-d]-pyrimidine.

10. A pharmaceutical composition comprising a compound of the formula I, in accordance with claim 1, and a pharmaceutically acceptable carrier.

11. A method for the treatment of a benign or malignant tumour which method comprises administering, to a host in need of such treatment, a therapeutic amount of a compound of the formula I in accordance with claim 1, 2, 3, 4, 5, 6, 7, 8 or 9.

12. The method of claim 11 wherein the tumour to be treated is a tumour of epithelial and neuroepithelial origin.

13. A method for treating abnormal proliferation of vascular endothelial cells (neoangiogenesis) which comprises administering, to a host in need of such treatment, a therapeutic amount of a compound of the formula I in accordance with claim 1, 2, 3, 4, 5, 6, 7, 8 or 9.

* * * * *